(12) United States Patent
Asher et al.

(10) Patent No.: US 11,076,881 B2
(45) Date of Patent: Aug. 3, 2021

(54) ELECTRICAL LOCKOUT FOR ULTRASONIC SURGICAL INSTRUMENT

(71) Applicant: ETHICON LLC, Guaynabo, PR (US)

(72) Inventors: Ryan M. Asher, Cincinnati, OH (US); Brian D. Black, Loveland, OH (US); John E. Brady, Liberty Township, OH (US); Alexander R. Cuti, Cincinnati, OH (US); Demetrius N. Harris, Cincinnati, OH (US); Carl J. Draginoff, Jr., Mason, OH (US); Ellen Burkart, Cincinnati, OH (US); Geni M. Giannotti, Cincinnati, OH (US); Andrew Kolpitcke, Centerville, OH (US); Amy M. Krumm, Cincinnati, OH (US); Matthew T. Kuhn, Houston, TX (US); Stephen M. Leuck, Cincinnati, OH (US); Cameron D. McLain, Cincinnati, OH (US); Ion V. Nicolaescu, Carpentersville, IL (US); Candice Otrembiak, Loveland, OH (US); Amrita S. Sawhney, Cincinnati, OH (US); Aaron C. Voegele, Loveland, OH (US); Grace E. Waters, Cincinnati, OH (US); Fajian Zhang, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 433 days.

(21) Appl. No.: 15/951,747

(22) Filed: Apr. 12, 2018

(65) Prior Publication Data
US 2019/0314054 A1 Oct. 17, 2019

(51) Int. Cl.
*A61B 17/32* (2006.01)
*A61B 18/14* (2006.01)
(Continued)

(52) U.S. Cl.
CPC ........... *A61B 17/320092* (2013.01); *A61B 17/320068* (2013.01); *A61B 18/1445* (2013.01);
(Continued)

(58) Field of Classification Search
CPC ........ A61B 17/2804; A61B 17/320068; A61B 17/320092; A61B 18/1445;
(Continued)

(56) References Cited

U.S. PATENT DOCUMENTS

| 5,322,055 A | 6/1994 | Davison et al. |
| 5,873,873 A | 2/1999 | Smith et al. |

(Continued)

FOREIGN PATENT DOCUMENTS

| EP | 1 199 040 A2 | 4/2002 |
| EP | 2 870 938 A1 | 5/2015 |

(Continued)

OTHER PUBLICATIONS

European Search Report, Extended, and Written Opinion dated Jul. 17, 2019 for Application No. 19168695.5, 8 pgs.
(Continued)

*Primary Examiner* — Mohamed G Gabr
(74) *Attorney, Agent, or Firm* — Frost Brown Todd LLC

(57) ABSTRACT

An ultrasonic surgical instrument and method of assembly with a predetermined alignment includes first and second modular assemblies and an electrical lockout. The first modular assembly includes at least a portion of an end effector configured to manipulate a tissue. The second modular assembly includes a transducer power circuit and an activation switch electrically connected to the transducer power circuit. The electrical lockout is electrically connected to the transducer power circuit and configured to inhibit the activation switch from powering the ultrasonic
(Continued)

transducer with the first and second modular assemblies misaligned from the predetermined alignment such that the first and second modular assemblies are in a locked-out state. The electrical lockout is further configured to allow the activation switch to power the ultrasonic transducer with the first and second modular assemblies in the predetermined alignment such that the first and second modular assemblies are in an operational state.

20 Claims, 41 Drawing Sheets

(51) Int. Cl.
    *A61B 17/00*     (2006.01)
    *A61B 18/00*     (2006.01)

(52) U.S. Cl.
    CPC .............. *A61B 2017/00039* (2013.01); *A61B 2017/00061* (2013.01); *A61B 2017/00137* (2013.01); *A61B 2017/00199* (2013.01); *A61B 2017/00402* (2013.01); *A61B 2017/00424* (2013.01); *A61B 2017/00477* (2013.01); *A61B 2017/320074* (2017.08); *A61B 2017/320095* (2017.08); *A61B 2018/0063* (2013.01); *A61B 2018/00994* (2013.01)

(58) Field of Classification Search
    CPC ........... A61B 2017/00039; A61B 2017/00061;
                  A61B 2017/00137; A61B 2017/00199;
                  A61B 2017/00402; A61B 2017/00424;
                  A61B 2017/0046; A61B 2017/00477;
             A61B 2017/320074; A61B 2017/320094;
              A61B 2017/320095; A61B 2018/0063;
               A61B 2018/00994; A61B 2090/0808
    See application file for complete search history.

(56) References Cited

U.S. PATENT DOCUMENTS

| | | | |
|---|---|---|---|
| 5,980,510 | A | 11/1999 | Tsonton et al. |
| 6,325,811 | B1 | 12/2001 | Messerly |
| 6,623,500 | B1 * | 9/2003 | Cook ................ A61B 18/1402 606/170 |
| 6,773,444 | B2 | 8/2004 | Messerly |
| 6,783,524 | B2 | 8/2004 | Anderson et al. |
| 8,663,220 | B2 | 3/2014 | Wiener et al. |
| 9,681,884 | B2 | 6/2017 | Clem et al. |
| 10,368,892 | B2 | 8/2019 | Stulen et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2009/0105750 | A1 | 4/2009 | Price et al. |
| 2010/0069940 | A1 | 3/2010 | Miller et al. |
| 2011/0015660 | A1 | 1/2011 | Wiener et al. |
| 2011/0087212 | A1 | 4/2011 | Aldridge et al. |
| 2012/0029546 | A1 | 2/2012 | Robertson |
| 2012/0112687 | A1 | 5/2012 | Houser et al. |
| 2012/0116265 | A1 | 5/2012 | Houser et al. |
| 2014/0005701 | A1 | 1/2014 | Olson et al. |
| 2014/0114334 | A1 | 4/2014 | Olson et al. |
| 2014/0330298 | A1 | 11/2014 | Arshonsky et al. |
| 2015/0080924 | A1 | 3/2015 | Stulen et al. |
| 2015/0080925 | A1 | 3/2015 | Schulte et al. |
| 2015/0141981 | A1 | 5/2015 | Price et al. |
| 2017/0000541 | A1 | 1/2017 | Yates et al. |
| 2017/0105754 | A1 * | 4/2017 | Boudreaux ............ A61B 90/04 |
| 2017/0105755 | A1 | 4/2017 | Boudreaux et al. |
| 2017/0105788 | A1 | 4/2017 | Boudreaux |
| 2018/0132926 | A1 | 5/2018 | Asher et al. |

FOREIGN PATENT DOCUMENTS

| | | |
|---|---|---|
| EP | 3 225 176 A1 | 10/2017 |
| WO | WO 2017/100412 A1 | 6/2017 |

OTHER PUBLICATIONS

European Search Report, Extended, and Written Opinion dated Jul. 5, 2019 for Application No. EP 19168712.8, 8 pgs.
European Search Report, Extended, and Written Opinion dated Jul. 3, 2019 for Application No. EP 19168735.9, 8 pgs.
European Search Report, Extended, and Written Opinion dated Jul. 11, 2019 for Application No. EP 19168796.1, 8 pgs.
International Search Report and Written Opinion dated Jul. 3, 2019 for Application No. PCT/IB2019/053002, 15 pgs.
International Search Report and Written Opinion dated Jul. 11, 2019 for Application No. PCT/IB2019/053004, 12 pgs.
International Search Report and Written Opinion dated Jul. 11, 2019 for Application No. PCT/IB2019/053008, 12 pgs.
International Search Report and Written Opinion dated Jul. 17, 2019 for Application No. PCT/IB2019/053009, 11 pgs.
U.S. Appl. No. 61/410,603, entitled "Energy-Based Surgical Instruments," filed Nov. 5, 2010.
U.S. Appl. No. 62/363,411, entitled "Surgical Instrument with Dual Mode End Effector," filed Jul. 18, 2016.
U.S. Appl. No. 15/644,930, entitled "Acoustic Drivetrain with External Collar at Nodal Position," filed Jul. 10, 2017.
U.S. Appl. No. 15/644,944, entitled "Features to Couple Acoustic Drivetrain Components in Ultrasonic Surgical Instrument," filed Jul. 10, 2017.
U.S. Appl. No. 15/951,773, entitled "Mechanical Lockout for Ultrasonic Surgical Instrument," filed Apr. 12, 2018.
U.S. Appl. No. 15/951,788, entitled "Mechanical Lockout for Ultrasonic Surgical Instrument," filed Apr. 12, 2018.
U.S. Appl. No. 15/951,811, entitled "Mechanical Lockout for Ultrasonic Surgical Instrument," filed Apr. 12, 2018.
U.S. Appl. No. 15/951,773.
U.S. Appl. No. 15/951,788.
U.S. Appl. No. 15/951,811.

* cited by examiner

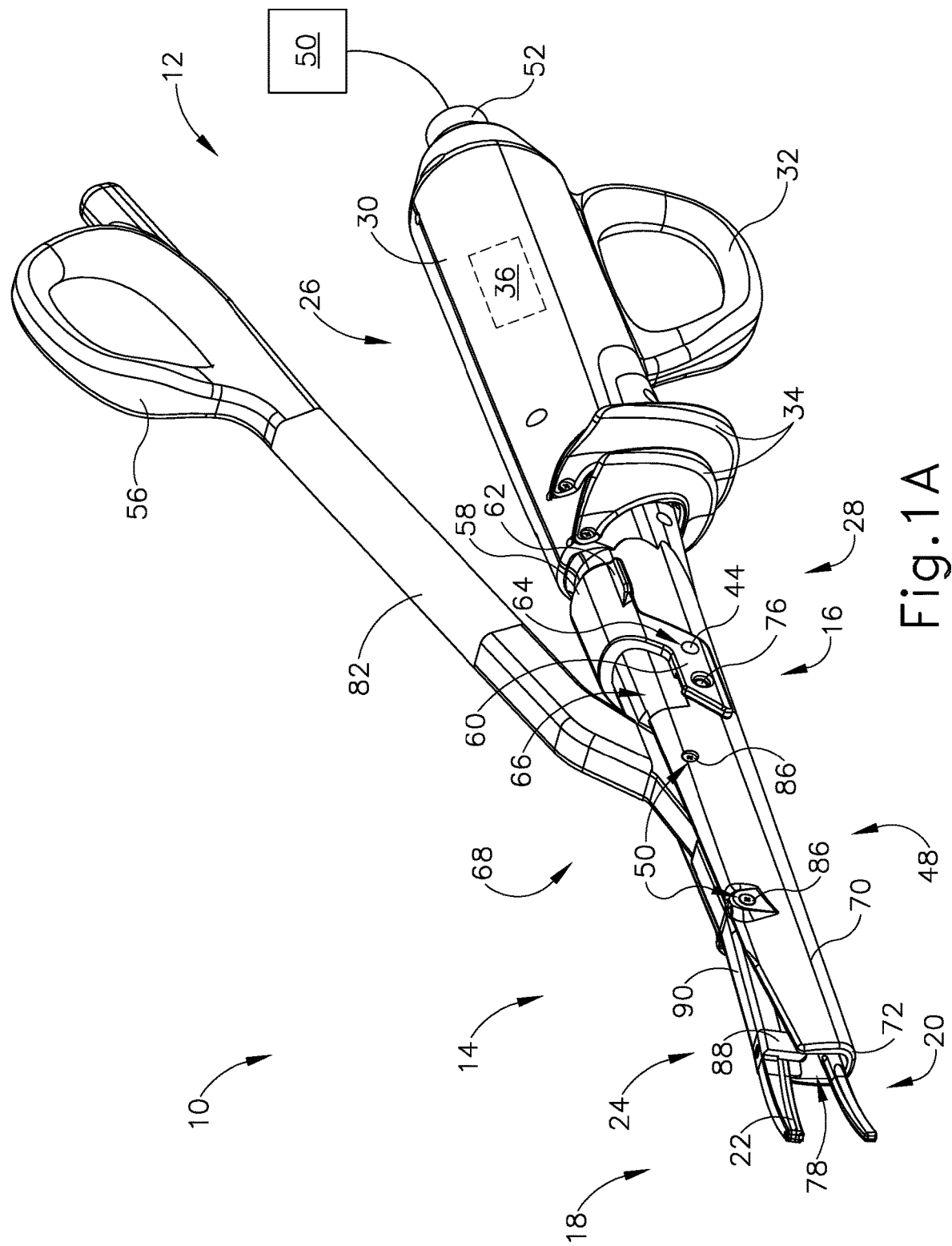

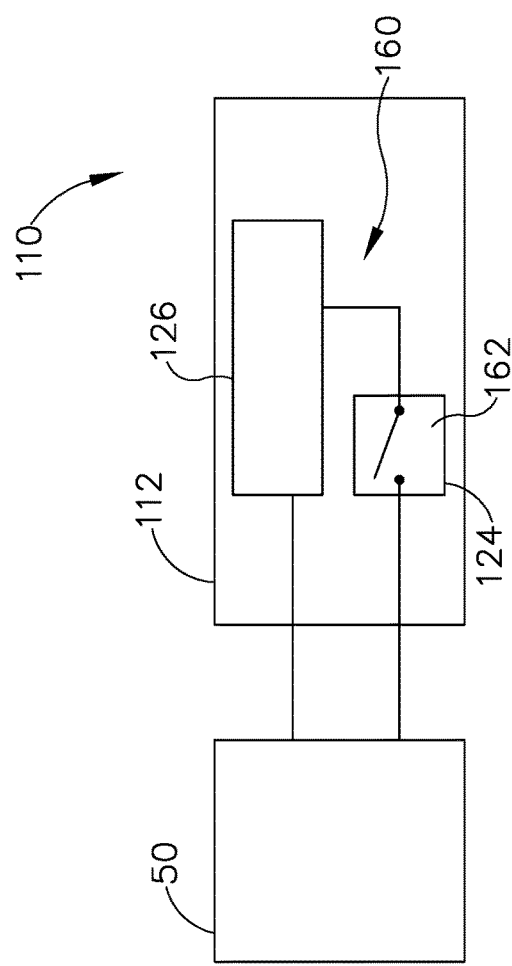
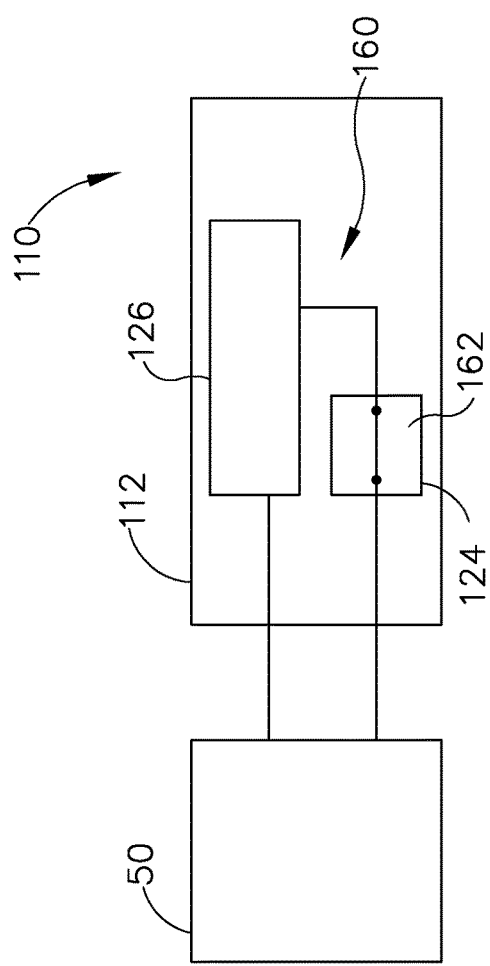

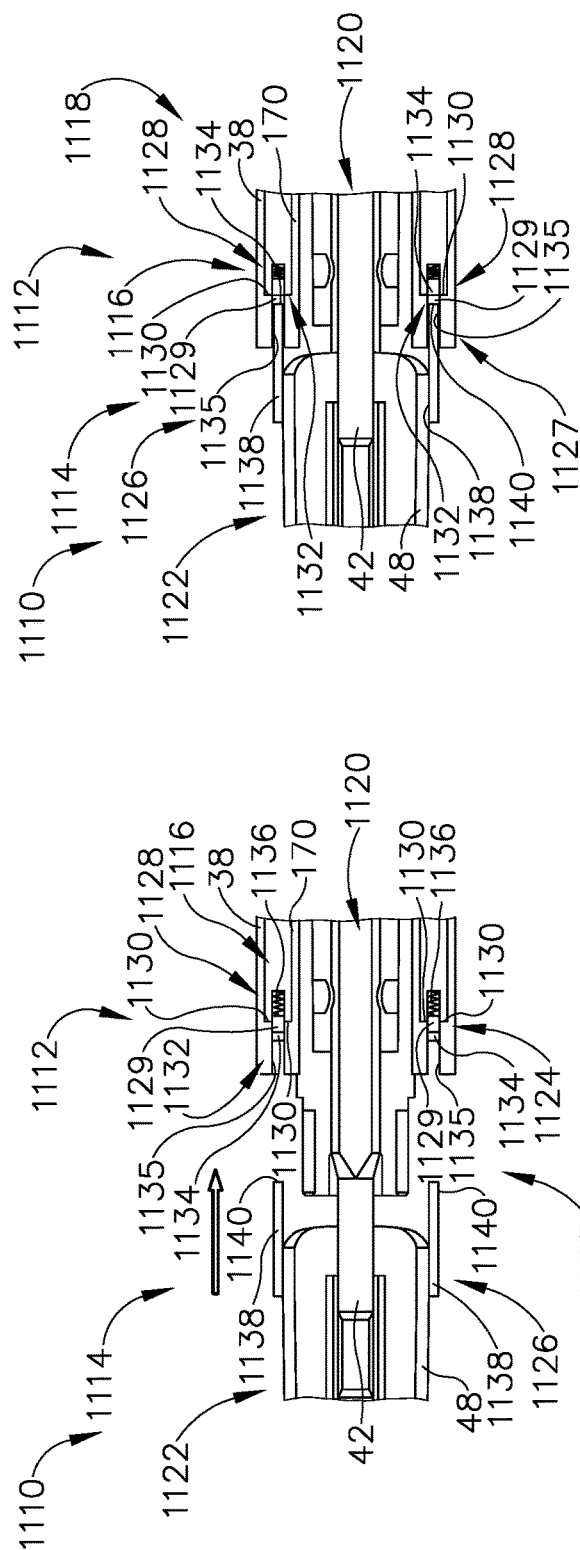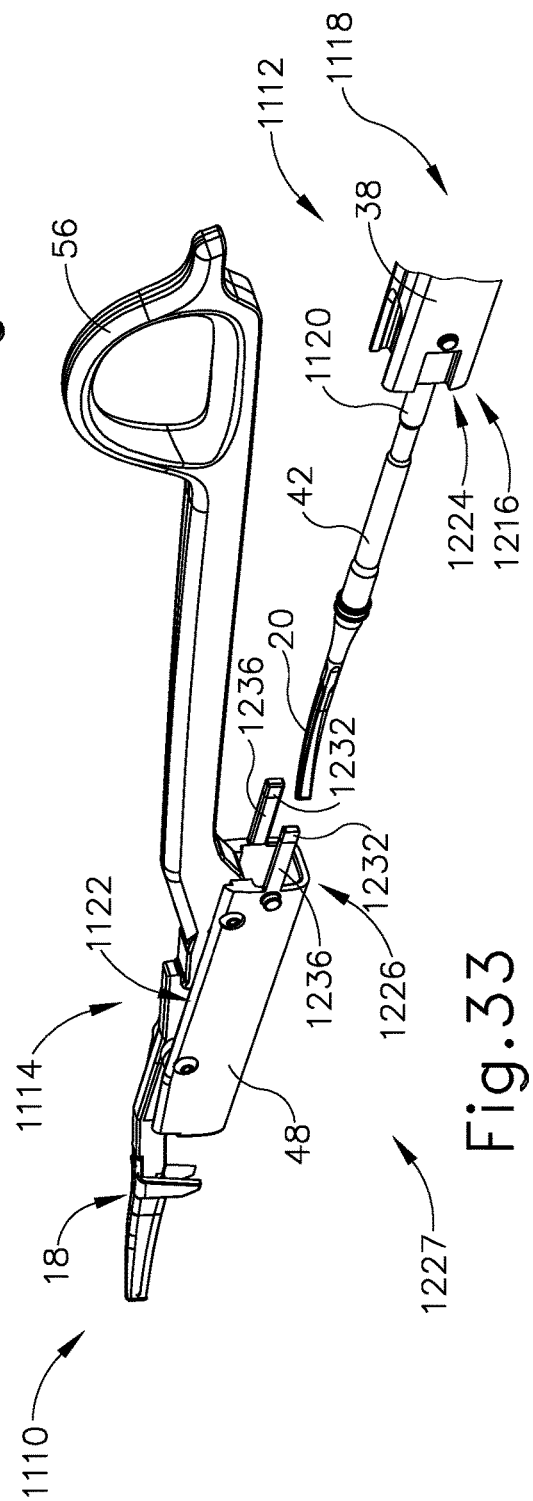

ELECTRICAL LOCKOUT FOR ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, issued as U.S. Pat. No. 9,393,037 on Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1A depicts a perspective view of a first exemplary surgical instrument, with an end effector of the instrument in an open configuration;

FIG. 8A depicts a diagrammatic view of an example of a transducer power circuit of the first or second ultrasonic surgical instruments of FIG. 1A and FIG. 3 in a selectively opened position such that the ultrasonic surgical instrument is powered off;

FIG. 8B depicts the diagrammatic view of the transducer power circuit similar to FIG. 8A, but in a selectively closed position such that the ultrasonic surgical instrument is powered on;

FIG. 32A depicts a schematic, enlarged, top sectional view of the surgical instrument of FIG. 30 with the clamp arm assembly being connected to the remainder of the surgical instrument;

FIG. 32B depicts the schematic, enlarged, top sectional view of the surgical instrument similar to FIG. 32A, but showing the clamp arm assembly connected to shaft assembly and the handle assembly such that the electrical lockout and the modular electrical coupling are in electrical connection and the surgical instrument is in an operational state;

FIG. 33 depicts a schematic, enlarged, proximal perspective view of the surgical instrument of FIG. 30 having a tenth example of an electrical lockout with a tenth modular electrical coupling and a clamp arm assembly removed from a remainder of the surgical instrument such that the surgical instrument is in a locked-out state;

Figure 1B:
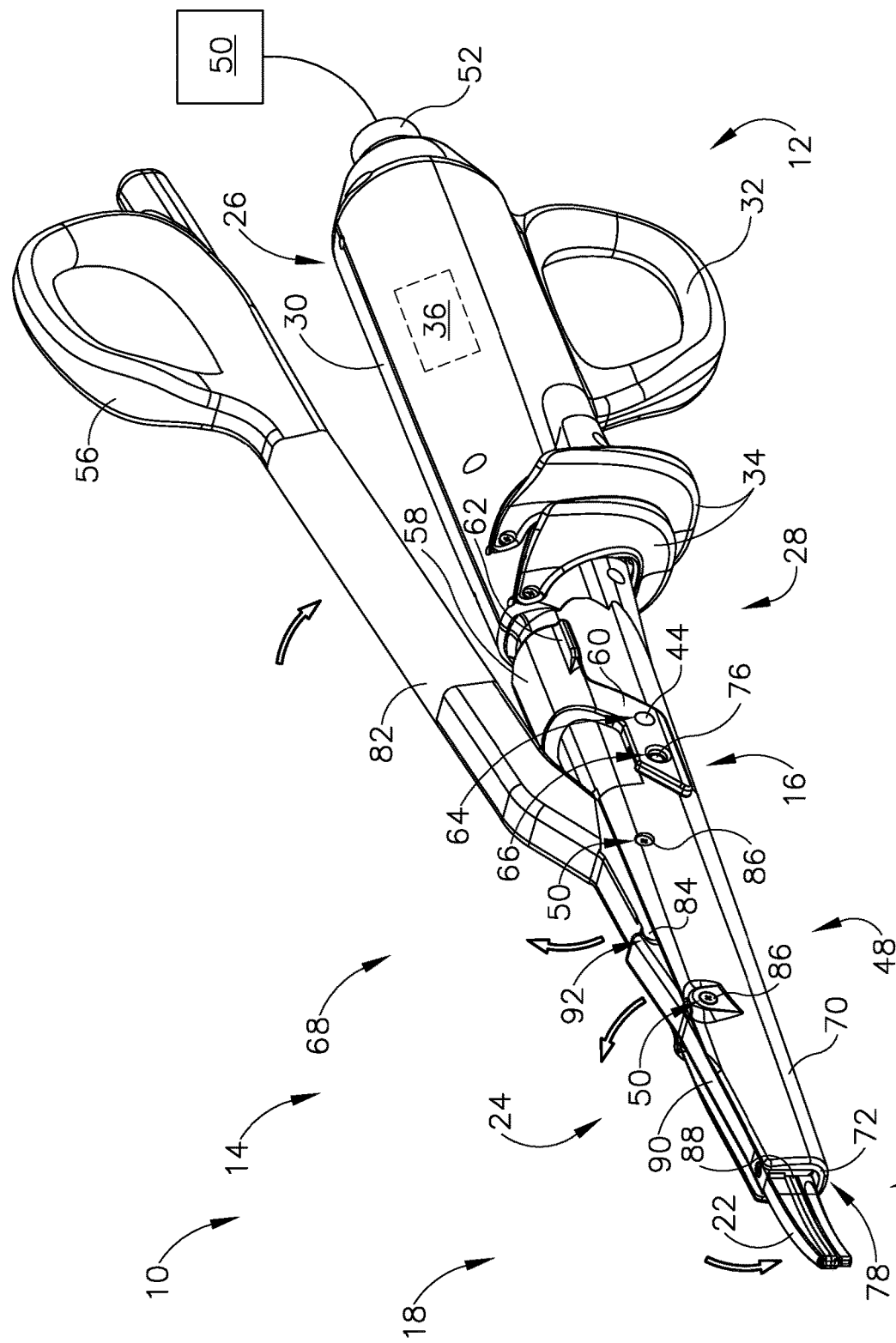
FIG. 1B depicts a perspective view of the instrument of FIG. 1A, with the end effector in a closed configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," "upper," and "lower" are relative terms to provide additional clarity to the figure descriptions provided below. The terms "upper," "lower," "lateral," "transverse," "bottom," "top," "upper," and "lower" are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. First Exemplary Ultrasonic Surgical Instrument for Surgical Procedures

Figure 2:
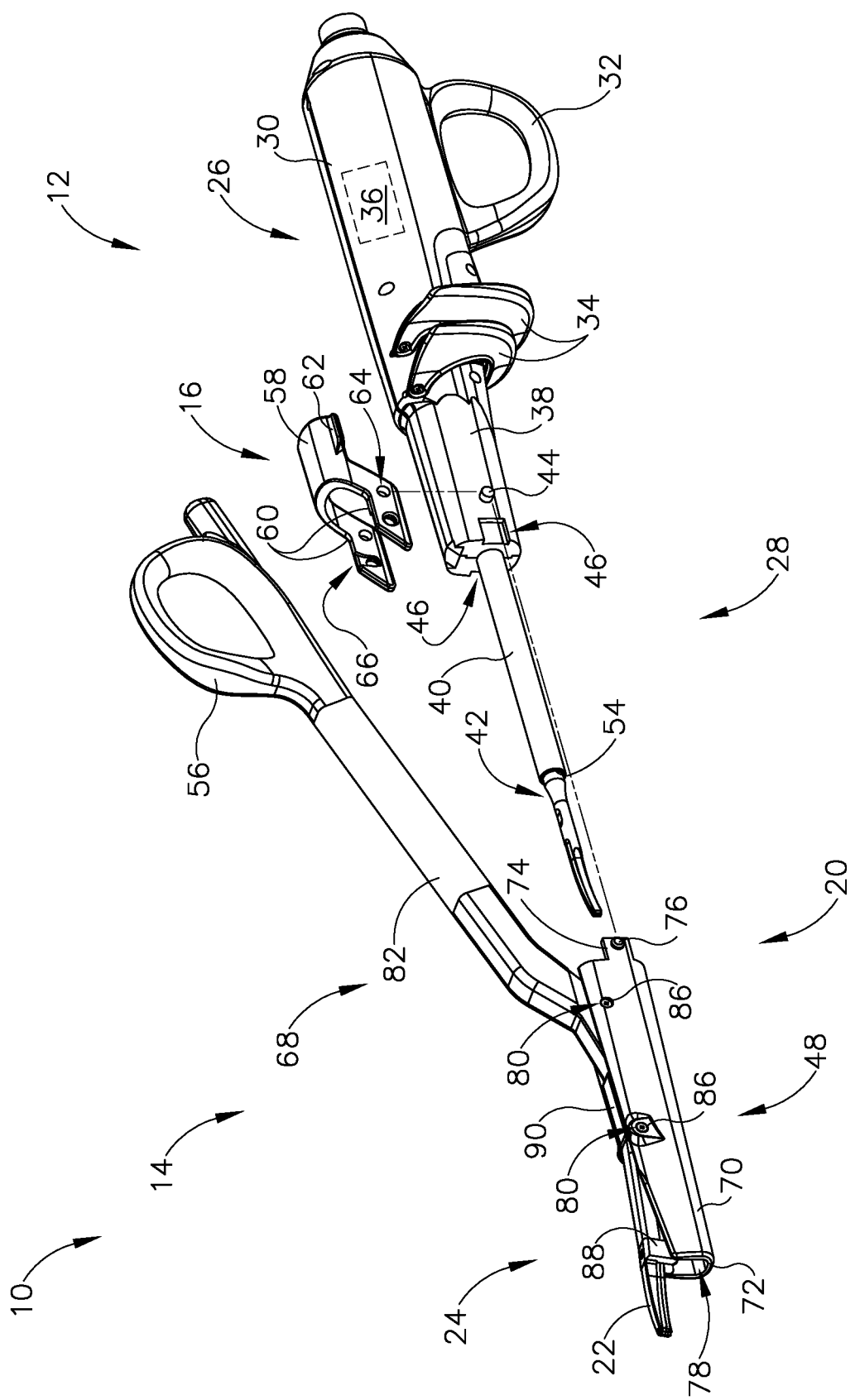
FIG. 2 depicts an exploded perspective view of the instrument of FIG. 1A.

FIGS. 1A-2 illustrate a first exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. In addition, or in the alternative, at least part of instrument (10) may be constructed and operable in accordance with at least some of the teachings of U.S. patent application Ser. No. 15/284,837, entitled "Surgical Instrument with Dual Mode End Effector and Compound Lever with Detents," filed Oct. 4, 2016, published as U.S. Pub. No. 2017/0105755 on Apr. 20, 2017, the disclosure of which is incorporated by reference herein; and/or U.S. Pat. App. No. 62/363,411, entitled "Surgical Instrument with Dual Mode End Effector," filed Jul. 18, 2016, the disclosure of which is incorporated by reference herein.

As described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

Instrument (10) in the present example includes a first modular assembly (12), a second modular assembly (14), and a coupling member (16). As will be described in greater detail below, coupling member (16) may selectively attach first modular assembly (12) with second modular assembly (14) in order to form instrument (10) with an end effector (18). As best seen in FIGS. 1A-1B, end effector (18) comprises an ultrasonic blade (20) and a clamp pad (22) of a clamp pad assembly (24).

Additionally, as will be described in greater detail below, selected portions of second modular assembly (14) may actuate relative to first modular assembly (12), when properly attached with each other, in order to actuate end effector (18) from an open configuration (FIG. 1A), to a closed configuration (FIG. 1B). The ability to selectively attach and detach second modular assembly (14) with first modular assembly (12) may provide additional benefits of reusability of either modular assembly (12, 14). For instance, different kinds of first modular assemblies (12) may be used with second modular assembly (14) to provide different kinds of surgical instruments. Similarly, different kinds of second modular assemblies (14) may be used with first modular assembly (12) to provide different kinds of surgical instruments. Additionally, moving components of second modular assembly (14) may be housed within static components of second modular assembly (14), which may provide additional advantages, some of which are described below while others will be apparent to one having ordinary skill in the art in view of the teachings herein.

First modular assembly (12) includes a handle assembly (26), a shaft assembly (28) extending distally from handle assembly (26), and ultrasonic blade (20) extending distally from shaft assembly (28). Handle assembly (26) includes a body (30), a finger grip ring (32), a pair of buttons (34) distal to finger grip ring (32), and an ultrasonic transducer assembly (36) housed within body (30).

Shaft assembly (28) includes a proximal outer sheath (38) extending distally from body (30), a tube (40) extending distally from proximal outer sheath (38), and a waveguide (42) extending within and through both proximal outer sheath (38) and tube (40). Proximal outer sheath (38) includes a pair of protrusions (44). Additionally, proximal outer sheath (38) defines a pair of recesses (46). As will be described in greater detail below, recesses (46) are dimensioned to mate with a portion of distal outer sheath (48) while protrusions (44) are configured to pivotally couple proximal outer sheath (38) with coupling member (16). Both protrusions (44) and recesses (46) may help couple first modular assembly (12) with second modular assembly (14).

Proximal outer sheath (38) may be fixed relative to body (30), while tube (40) may be fixed relative to proximal outer sheath (38). As will be described in greater detail below, waveguide (42) may attach to transducer assembly (36) and be supported by portions of proximal outer sheath (38) and tube (40). Ultrasonic blade (20) may be unitarily connected to waveguide (42), and also extend distally from waveguide (42). As will be described in greater detail below, waveguide (42) is operable to connect to ultrasonic transducer assembly (36) in order to provide acoustic communication between ultrasonic blade (20) and transducer assembly (36).

Transducer assembly (36) is housed within body (30) of handle assembly (26). As seen in FIGS. 1A-1B, transducer assembly (36) is coupled with a generator (50) via a plug (52). Transducer assembly (36) receives electrical power from generator (50) and converts that power into ultrasonic vibrations through piezoelectric principles. Generator (50) may include a power source and control module that is configured to provide a power profile to transducer assembly (36) that is particularly suited for the generation of ultrasonic vibrations through transducer assembly (36). Generator (50) may also be configured to provide a power profile that enables end effector (18) to apply RF electrosurgical energy to tissue.

By way of example only, generator (50) may comprise a GEN 300 sold by Ethicon Endo-Surgery, Inc. of Cincinnati, Ohio. In addition or in the alternative, generator (not shown) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (50) may be integrated into handle assembly (26), and that handle assembly (26) may even include a battery or other on-board power source such that plug (52) is omitted. Still other suitable forms that generator (50) may take, as well as various features and operabilities that generator (50) may provide, will be apparent to those of ordinary skill in the art in view of the teachings herein.

Ultrasonic vibrations that are generated by transducer assembly (36) are communicated along acoustic waveguide (42) when properly coupled. Waveguide (42) is mechanically and acoustically coupled with transducer assembly (36). Waveguide (42) extends through shaft assembly (28) to reach ultrasonic blade (20). Waveguide (42) may be secured to proximal outer sheath (38) and/or body (30) via a pin (not shown) extending through waveguide (42) and proximal outer sheath (38). Pin may help ensure waveguide (42) remains longitudinally and rotationally fixed relative to the rest of shaft assembly (28) when waveguide (42) is in a deactivated state (i.e. not vibrating ultrasonically).

Additionally, waveguide (42) may be supported by tube (40) via seals (54) located between an interior of tube (40) and an exterior of waveguide (42). Seals (54) may also prevent unwanted matter and fluid from entering portions of tube (40) housing waveguide (42). Pin (not shown) and seals (54) are located at positions along the length of waveguide

(42) corresponding to nodes associated with resonant ultrasonic vibrations communicated through waveguide (42). Therefore, contact between waveguide (42) and pin (not shown), as well as contact between waveguide (42) and seals (54) may not affect ultrasonic vibrations communicated through waveguide (42).

When ultrasonic blade (20) is in an activated state (i.e., vibrating ultrasonically), ultrasonic blade (20) is operable to effectively cut through and seal tissue, particularly when the tissue is being clamped between clamp pad (22) and ultrasonic blade (20). It should be understood that waveguide (42) may be configured to amplify mechanical vibrations transmitted through waveguide (42). Furthermore, waveguide (42) may include features operable to control the gain of the longitudinal vibrations along waveguide (42) and/or features to tune waveguide (42) to the resonant frequency of the system.

In the present example, the distal end of ultrasonic blade (20) is located at a position corresponding to an anti-node associated with resonant ultrasonic vibrations communicated through waveguide (42), in order to tune the acoustic assembly to a preferred resonant frequency $f_o$ when the acoustic assembly is not loaded by tissue. When transducer assembly (36) is energized, the distal end of ultrasonic blade (20) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (36) of the present example is activated, these mechanical oscillations are transmitted through the waveguide (42) reach ultrasonic blade (20), thereby providing oscillation of ultrasonic blade (20) at the resonant ultrasonic frequency. Thus, when tissue is secured between ultrasonic blade (20) and clamp pad (22), the ultrasonic oscillation of ultrasonic blade (20) may simultaneously sever the tissue and denature the proteins in adjacent tissue cells, thereby providing a coagulative effect with relatively little thermal spread.

In some versions, an electrical current may also be provided through ultrasonic blade (20) and/or clamp pad (22) to also seal the tissue. It should therefore be understood that instrument (10) may also be configured to provide radiofrequency (RF) energy to a surgical site via end effector (18). By way of example only, an operator may rely mainly on the use of ultrasonic energy from blade (20) to sever tissue that is captured between ultrasonic blade (20) and clamp pad (22). The operator may further rely on the use of RF energy from end effector (18) to seal the severed tissue. Of course, it will be understood that the ultrasonic energy from blade (20) may seal tissue to some degree, such that the RF energy from end effector (18) may supplement the sealing that would already be provided from the ultrasonic energy. It will also be understood that there may be instances where the operator may wish to simply use end effector (18) to only apply RF energy to tissue, without also applying ultrasonic energy to tissue. As will be appreciated from the description herein, some versions of instrument (10) are capable of providing all of the above noted kinds of functionality. Various ways in which instrument (10) may be configured and operable to provide both ultrasonic and RF electrosurgical modes of operation are described in various references cited herein; while other ways in which instrument (10) may be configured and operable to provide both ultrasonic and RF electrosurgical modes of operation will be apparent to those of ordinary skill in the art in view of the teachings herein.

An operator may activate buttons (34) to selectively activate transducer assembly (36) to thereby activate ultrasonic blade (20). In the present example, two buttons (34) are provided. In some versions, one button (34) is provided for activating ultrasonic blade (20) at a first power profile (e.g., a first frequency and/or first amplitude) and another button (34) is provided for activating ultrasonic blade (20) at a second power profile (e.g., a second frequency and/or second amplitude). In some other versions, one button (34) is provided for activating ultrasonic blade (20) with ultrasonic energy, and the other button (34) is provided for activating end effector (18) with RF energy. In some other versions, one button (34) is operable to activate ultrasonic blade (20) with ultrasonic energy while simultaneously activating end effector (18) with RF energy; while the other button (34) is only operable to activate ultrasonic blade (20) with ultrasonic energy. In some other versions, at least one button (34) is operable to initially activate ultrasonic blade (20) with ultrasonic energy, then based on one or more other conditions (e.g., time, measured impedance, etc.) while button (34) remains activated, eventually activating end effector (18) with RF energy while still activating ultrasonic blade (20) with ultrasonic energy. In some other versions, at least one button (34) is operable to initially activate ultrasonic blade (20) with ultrasonic energy, then based on one or more other conditions (e.g., time, measured impedance, etc.) while button (34) remains activated, eventually activating end effector (18) with RF energy while ceasing activation of ultrasonic blade (20) with ultrasonic energy. In some other versions, at least one button (34) is operable to initially activate end effector (18) with RF energy, then based on one or more other conditions (e.g., time, measured impedance, etc.) while button (34) remains activated, eventually activating ultrasonic blade (20) with ultrasonic energy while ceasing activation of end effector (18) with RF energy.

It should be understood that any other suitable number of buttons and/or otherwise selectable power levels and/or power modalities may be provided. For instance, a foot pedal may be provided to selectively activate transducer assembly (36).

Buttons (34) of the present example are positioned such that an operator may readily fully operate instrument (10) with a single hand. For instance, when first and second modular assemblies (12, 14) are coupled, the operator may position their thumb in thumb grip ring (56), position their ring finger in finger grip ring (32), position their middle finger about body (30), and manipulate buttons (34) using their index finger. Of course, any other suitable techniques may be used to grip and operate instrument (10), and buttons (34) may be located at any other suitable position.

As mentioned above, and as will be described below, coupling member (16) is configured to selectively couple first modular assembly (12) with second modular assembly (14). As best seen in FIG. 2, coupling member (16) comprises a body (58), a pair of resilient arms (60), and a pair of grips (62) extending from body (58). Resilient arms (60) each define a respective pivot bore (64) and a locking assembly (66). Resilient arms (60) are spaced apart from each other in order to receive proximal outer sheath (38) and to snap-fit pivot bores (64) with respective protrusions (44). Coupling member (16) is configured to pivotally connect with proximal outer sheath (38) via pivot bores (64) and protrusions (44). While in the current example, coupling member (16) and proximal outer sheath (38) are pivotally coupled via snap-fitting, any other type of suitable connection may be used as would be apparent to one having ordinary skill in the art in view of the teachings herein. For example, protrusions (44) may be extendable relative to proximal outer sheath (38) in order to pivotally couple with pivot bore (64) of coupling member (16). Grips (62) may be positioned on body (58) such that an operator may easily rotate coupling member (16) relative to proximal outer sheath (38) via grips (62). As will be described in greater detail below, locking assembly (66) is configured to rotate about pivot bore (64) and protrusions (44) in order to selectively couple with portions of second modular assembly (14).

While coupling member (16) in the current example is used to connect first modular assembly (12) with second modular assembly (14), it should be understood that coupling member (16) may be incorporated into any suitable type of modular assembly that would be apparent to one having ordinary skill in the art in view of the teachings herein. For example, coupling member (16) may be modified to couple different modular clamp arm assemblies with first modular assembly (12) where the different modular clamp arm assemblies include clamp arm assemblies such as those taught in U.S. patent application Ser. No. 15/284,855, entitled "Surgical Instrument with Dual Mode End Effector and Modular Clamp Arm Assembly," filed Oct. 4, 2016, issued as U.S. Pat. No. 10,893,914 on Jan. 19, 2021, the disclosure of which is incorporated by reference herein. Thus, one modular clamp arm assembly that may be coupled with first modular assembly (12) may provide pivotal motion of a clamp arm at one side of ultrasonic blade (20) while the other modular clamp arm assembly that may be coupled with first modular assembly (12) may provide pivotal motion of a clamp arm at the other side of ultrasonic blade (20). Other suitable kinds of clamp arm assemblies that may be used to provide different kinds of second modular assemblies (14) will be apparent to those of ordinary skill in the art in view of the teachings herein.

Second modular assembly (14) includes a clamp arm assembly (68), clamp pad assembly (24), and a distal outer sheath (48). As will be described in greater detail below, distal outer sheath (48) is configured to couple with both coupling member (16) and proximal outer sheath (38) in order to selectively couple first modular assembly (12) with second modular assembly (14). It other words, when properly coupled, proximal outer sheath (38) and distal outer sheath (48) may be fixed relative to one another. As will also be described in greater detail below, clamp arm assembly (68) and clamp pad assembly (24) are both pivotally coupled with distal outer sheath (48). Additionally, clamp arm assembly (68) and clamp pad assembly (24) are dimensioned to mesh with each other such that rotation of one assembly (24, 68) relative to distal outer sheath (48) causes rotation of the other assembly (24, 68) relative to distal outer sheath (48). In other words, clamp pad assembly (24) and clamp arm assembly (68) are capable of rotating each other relative to distal outer sheath (48).

Distal outer sheath (48) includes a U-shaped body (70) extending from a distal face (72) and terminating in a pair of proximally presented projections (74). Proximally presented projections (74) each include a lateral protrusion (76) extending away from U-shaped body (70). U-shaped body (70) defines a longitudinal pathway (78) and a plurality of bores (80). U-shaped body (70) and longitudinal pathway (78) are dimensioned to receive tube (40) and to rotationally house a portion of clamp arm assembly (68) and clamp pad assembly (24). In particular, U-shaped body (70) may be inserted over ultrasonic blade (20) and tube (40) such that tube (40) will rest under clamp arm assembly (68) and clamp pad assembly (24). Tube (40) may protect waveguide (42) such that clamp arm assembly (68) and clamp pad assembly (24) do not contact adjacent portions of waveguide (42).

As shown in FIG. 2, proximally presented projections (74) are configured to be inserted into recesses (46) defined by proximal outer sheath (38). When proximally presented projections (74) are inserted into recesses (46), distal outer sheath (48) may not rotate relative to proximal outer sheath (38) about a longitudinal axis defined by tube (40). Therefore, proximally presented projections (74) may mate with recesses (46) in order to rotationally fix distal outer sheath (48) relative to proximal outer sheath (38).

Once distal outer sheath (48) is rotationally fixed relative to proximal outer sheath (38), an operator may rotate coupling member (16) such that locking assembly (66) snap-fits with lateral protrusions (76). In particular, an operator may rotate coupling member (16) about protrusions (44) such that lateral protrusions (76) cam against resilient arms (60). As a result, resilient arms (60) are flexed outwardly away from proximally presented projections (74). An operator may further rotate coupling member (16) about protrusions (44). The resilient nature of resilient arms (60) allows resilient arms (60) to return to a relaxed position such that lateral protrusions (76) rest within locking assembly (66). With locking assembly (66) of coupling member (16) fully attached, distal outer sheath (48) is longitudinally fixed relative to proximal outer sheath (38), thereby coupling first modular assembly (12) with second modular assembly (14).

If an operator wishes to decouple first modular assembly (12) with second modular assembly (14), an operator may grasp grips (62) to rotate coupling member (16) in the opposite direction about protrusions (44) in order to flex resilient arms (60) to pop out lateral protrusions (76).

As mentioned above, clamp arm assembly (68) and clamp pad assembly (24) are both pivotally coupled with distal outer sheath (48) such that rotation of one assembly (24, 68) relative to distal outer sheath (48) causes rotation of the other assembly (24, 68) relative to distal outer sheath (48).

Clamp arm assembly (68) includes an elongated arm (82), thumb grip ring (56), a camming protrusion (84) seen in FIG. 1B. Thumb grip ring (56) and elongated arm (82) together provide a scissor grip type configuration in combination with body (30) and finger grip ring (32). Pivot coupling pivotally couples clamp arm assembly (68) with distal outer sheath (48) via pins (86). As will be described in greater detail below, camming protrusion (84) interacts with clamp pad assembly (24) in order to rotate clamp pad assembly (24) in response to rotation of clamp arm assembly (68).

Clamp pad assembly (24) includes clamp pad (24) facing ultrasonic blade (20), a pair of tissue stops (88) located adjacent to ultrasonic blade (20) and proximal to clamp pad (22), an arm (90) defining a camming recess (92) as seen in FIG. 1B. In some versions, clamp pad assembly (24) further includes one or more electrodes that is/are operable to apply RF electrosurgical energy to tissue. Various references herein provide examples of how a clamp pad assembly may incorporate one or more electrodes that is/are operable to apply RF electrosurgical energy to tissue, while other examples of how clamp pad assembly (24) may incorporate one or more electrodes that is/are operable to apply RF electrosurgical energy to tissue will be apparent to those of ordinary skill in the art in view of the teachings herein.

In the current example, tissue stops (88) longitudinally align with distal face (72) when end effector (18) is in the closed position. Tissue stops (88) and distal face (72) may cooperate to consistently and simply prevent tissue from inadvertently reaching a proximal position within end effector (18) where ultrasonic energy from blade (20) may not adequately sever or seal the tissue. In providing such prevention, tissue stop (88) may eliminate the need for an operator to visualize proximal region of end effector (18) in order to determine whether the tissue has reached an undesirably proximal position within end effector (18).

Camming protrusion (84) is dimensioned to rotate within camming recess (92) while also contacting camming recess (92). Camming protrusion (84) and camming recess (92) are positioned within distal outer sheath (48). Therefore, as shown between FIGS. 1A-1B, when an operator rotates elongated arm (82) toward distal outer sheath (48), camming protrusion (84) rotates away from distal outer sheath (48). Because camming protrusion (84) is housed within camming recess (92), upward movement of camming protrusion (84) causes upward movement of camming recess (92). Upward movement of camming recess (92) rotates arm (90) such that clamp pad (22) rotates toward ultrasonic blade (20). Therefore, closure of elongated arm (82) of clamp arm assembly (68) toward handle assembly (26) leads to closure of clamp pad (22) toward ultrasonic blade (20). It should therefore be understood that when first modular assembly (12) and second modular assembly (14) are connected, an operator may squeeze thumb grip ring (56) toward body (30) to thereby clamp tissue between clamp pad assembly (24) and ultrasonic blade (20) to compress tissue against ultrasonic blade (20). When ultrasonic blade (20) is activated during such compression, clamp pad assembly (24) and ultrasonic blade (20) cooperate to transect and/or seal the compressed tissue.

In some versions, one or more resilient members are used to bias clamp pad assembly (24) toward the open position shown in FIG. 1A. Of course, any other suitable kind of resilient member may be used as would be apparent to one having ordinary skill in the art in view of the teachings herein, such as a torsion spring. Alternatively, clamp pad assembly (24) need not necessarily be biased toward the open position.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned U.S. Pub. No. 2007/0191713 now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; and/or U.S. Pub. No. 2015/0080925, entitled "Alignment Features for Ultrasonic Surgical Instrument," published Mar. 19, 2015, now abandoned, the disclosure of which is incorporated by reference herein.

II. Second Exemplary Ultrasonic Surgical Instrument for Surgical Procedures

Figure 3:
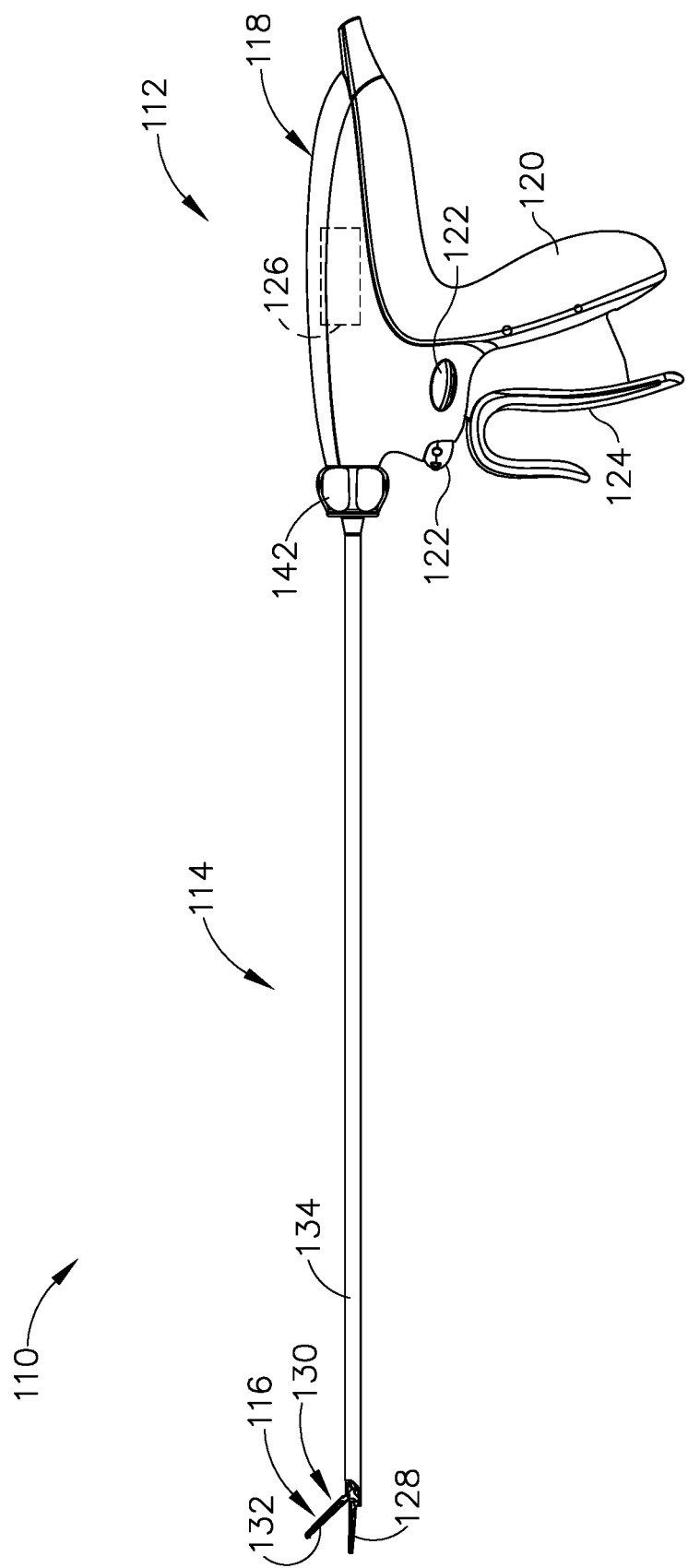
FIG. 3 depicts a side view of a second exemplary ultrasonic surgical instrument having a handle assembly and a shaft assembly with an end effector.
Figure 4A:
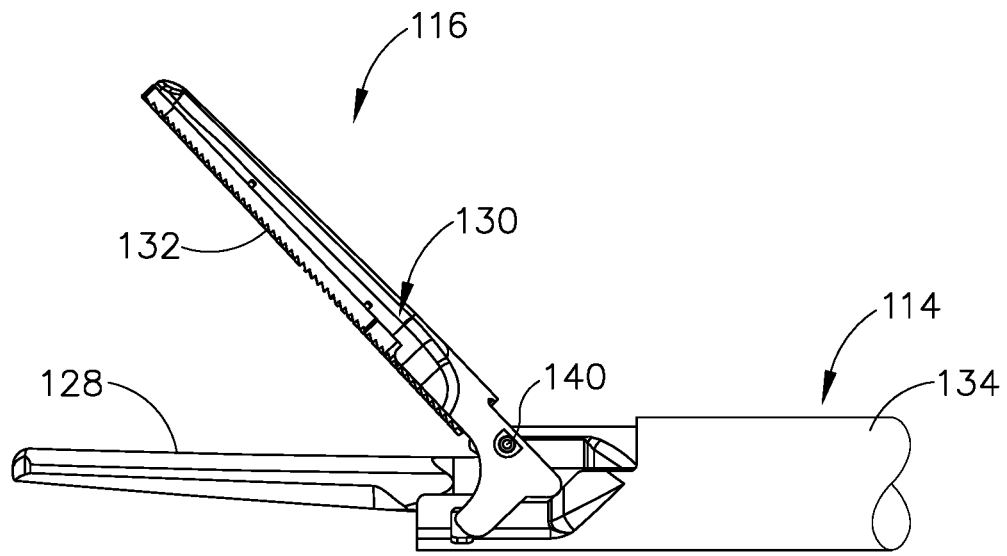
FIG. 4A depicts an enlarged side view of the end effector of FIG. 3 in an open configuration.
Figure 4B:
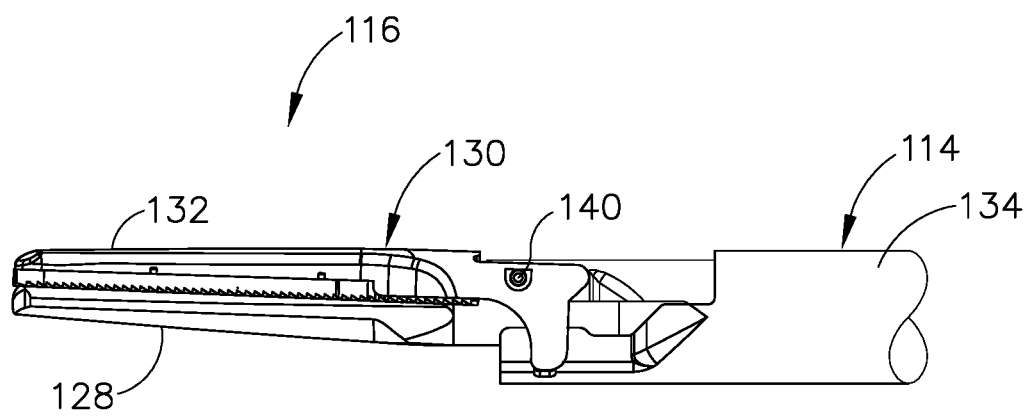
FIG. 4B depicts the enlarged side view of the end effector similar to FIG. 4A, but with the end effector in a closed configuration.

FIGS. 3-4B show an exemplary ultrasonic surgical instrument (110) that includes a first modular assembly shown as a handle assembly (112), a second modular assembly shown as a shaft assembly (114) extending distally from handle assembly (112), and an end effector (116) arranged at a distal end of shaft assembly (114). Handle assembly (112) comprises a body (118) including a pistol grip (120) and energy control buttons (122) configured to be manipulated by a surgeon to control various aspects of tissue treatment energy delivered by surgical instrument (110). A trigger (124) is coupled to a lower portion of body (118) and is pivotable toward and away from pistol grip (120) to selectively actuate end effector (116). In other suitable variations of surgical instrument (110), handle assembly (112) may comprise a scissor grip configuration, for example. Body (118) houses an ultrasonic transducer (126), shown schematically in FIG. 3, configured to deliver ultrasonic energy to end effector (116), as described in greater detail below. Body (118) may also be referred to herein as a housing (118) and may include one component or an assembly of components. The terms "body" and "housing" are thus not intended to unnecessarily limit the invention described herein to any number of discrete components.

As shown best in FIGS. 4A-4B, end effector (116) includes an ultrasonic blade (128) and a clamp arm (130) configured to selectively pivot toward and away from ultrasonic blade (128) for clamping tissue therebetween. Clamp arm (130) includes a clamp pad (132) arranged on a clamping side thereof and is moveable from an open position shown in FIG. 4A to a closed position shown in FIG. 4B. With respect to FIG. 3, ultrasonic blade (128) is acoustically coupled with ultrasonic transducer (126), which is configured to drive (i.e., vibrate) ultrasonic blade (128) at ultrasonic frequencies for cutting and/or sealing tissue positioned in contact with ultrasonic blade (128). Clamp arm (130) is operatively coupled with trigger (124) such that clamp arm (130) is configured to pivot toward ultrasonic blade (128), to the closed position, in response to pivoting of trigger (124) toward pistol grip (120). Further, clamp arm (130) is configured to pivot away from ultrasonic blade (128), to the open position in response to pivoting of trigger (124) away from pistol grip (120). Various suitable ways in which clamp arm (130) may be coupled with trigger (124) will be apparent to those of ordinary skill in the art in view of the teachings provided herein. In some versions, one or more resilient members may be incorporated to bias clamp arm (130) and/or trigger (124) toward the open position.

Shaft assembly (114) of the present example extends along a longitudinal axis and includes an outer tube (134), an inner tube (136) received within outer tube (134), and an ultrasonic waveguide (138) supported within and extending longitudinally through inner tube (136). Ultrasonic blade (128) is formed integrally with and extends distally from waveguide (138). A proximal end of clamp arm (130) is pivotally coupled to distal ends of outer and inner tubes (134, 136), enabling clamp arm (130) to pivot relative to shaft assembly (114) about a pivot axis defined by a pivot pin (140) (see FIGS. 4A and 4B) extending transversely through the distal end of inner tube (136).

In the present example, inner tube (136) is longitudinally fixed relative to handle assembly (118), and outer tube (134) is configured to translate relative to inner tube (136) and handle assembly (118), along the longitudinal axis of shaft assembly (120). As outer tube (134) translates distally, clamp arm (130) pivots about its pivot axis toward its open position. As outer tube (134) translates proximally, clamp arm (130) pivots about its pivot axis in an opposite direction toward its closed position. Though not shown, a proximal end of outer tube (134) is operatively coupled with trigger (124) such that actuation of trigger (124) causes translation of outer tube (134) relative to inner tube (136), thereby opening or closing clamp arm (130) as discussed above. In other suitable configurations not shown herein, outer tube (134) may be longitudinally fixed and inner tube (136) may be configured to translate for moving clamp arm (130) between the open and closed positions. Various other suitable mechanisms for actuating clamp arm (130) between the open and closed positions will be apparent to those of ordinary skill in the art.

Figure 5:
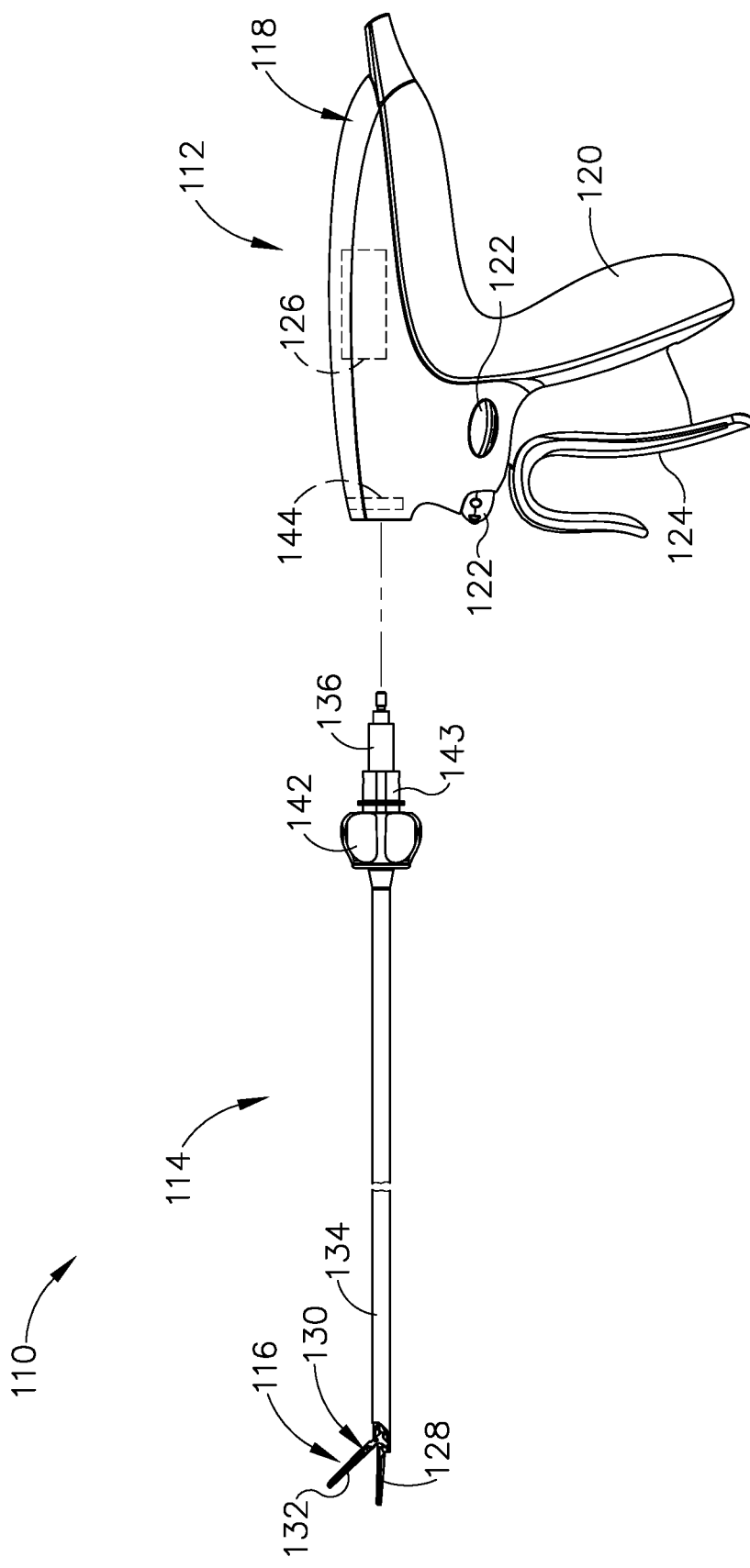
FIG. 5 depicts a partially exploded side view of the ultrasonic surgical instrument of FIG. 3.
Figure 6:
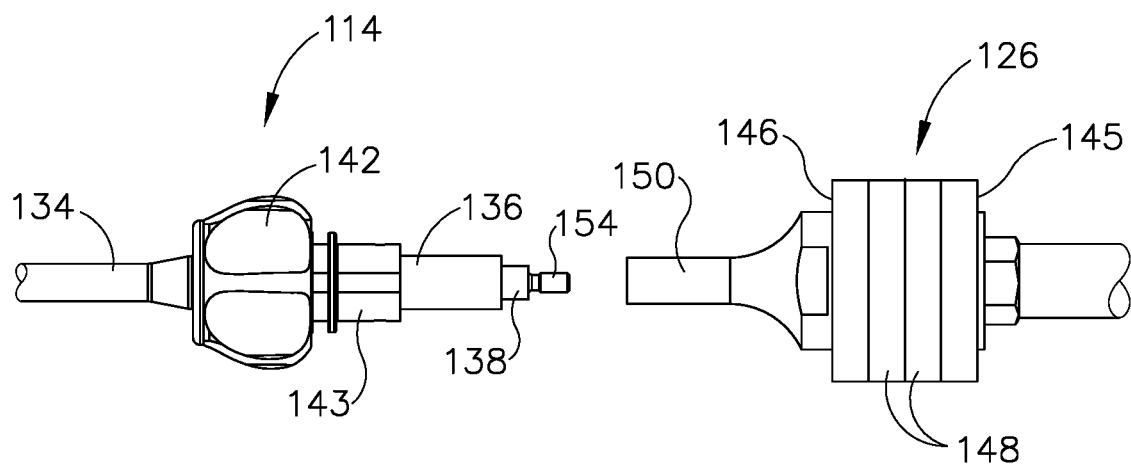
FIG. 6 depicts a partially schematic enlarged side view of an ultrasonic transducer, a waveguide, and a rotation knob of the ultrasonic surgical instrument of FIG. 3, showing attachment of the waveguide to the ultrasonic transducer.

Shaft assembly (114) and end effector (116) are configured to rotate together relative to body (118) about the longitudinal axis defined by shaft assembly (114). As shown in FIGS. 5-6, shaft assembly (114) further includes a rotation knob (142) arranged at a proximal end thereof as well as a shaft coupler (143) configured to mechanically connect to a body coupler (144) of handle assembly (112). Rotation knob (142) is rotatably coupled to body (118) of handle assembly (112), and is rotationally fixed to outer tube (134), inner tube (136), and waveguide (138) by a coupling pin (not shown) extending transversely therethrough. Coupling pin (not shown) is arranged at a longitudinal location corresponding to an acoustic node of waveguide (138). In other examples, rotation knob (142) may be rotationally fixed to the remaining components of shaft assembly (114) in various other manners. Rotation knob (142) is configured to be gripped by a user to selectively manipulate the rotational orientation of shaft assembly (114) and end effector (116) relative to handle assembly (112). Various examples of acoustic and mechanical connections between shaft assembly (114) and handle assembly (112) are described in greater detail in U.S. patent application Ser. No. 15/644,930, entitled "Acoustic Drivetrain with External Collar at Nodal Position," filed on Jul. 10, 2017, issued as U.S. Pat. No. 10,813,662 on Oct. 27, 2020 and U.S. patent application Ser. No. 15/644,944, entitled "Features to Couple Acoustic Drivetrain Components in Ultrasonic Surgical Instrument," filed on Jul. 10, 2017, issued as U.S. Pat. No. 10,709,470 on Jul. 14, 2020, the disclosures of which are each incorporated by reference herein.

FIGS. 3-5 show additional details of ultrasonic transducer (126) and waveguide (138). In particular, ultrasonic transducer (126) and waveguide (138) are configured to threadedly couple together. Accordingly, waveguide (138) is configured to acoustically couple ultrasonic transducer (126) with ultrasonic blade (128), and thereby communicate ultrasonic mechanical vibrations from ultrasonic transducer (126) to blade (128). In this manner, ultrasonic transducer (126), waveguide (138), and ultrasonic blade (128) together define an acoustic assembly of ultrasonic surgical instrument (110). Ultrasonic transducer (126) is rotatably supported within body (118) of handle assembly (112), and is configured to rotate with shaft assembly (114), including waveguide (138), and end effector (116) about the longitudinal axis of shaft assembly (114).

Ultrasonic transducer (126) is electrically coupled with a generator (50) (see FIG. 1A), which may be provided externally of ultrasonic surgical instrument (110) or integrated within surgical instrument (110). During use, generator (50) (see FIG. 1A) powers ultrasonic transducer (126) to produce ultrasonic mechanical vibrations, which are communicated distally through waveguide (138) to ultrasonic blade (128). Ultrasonic blade (128) is caused to oscillate longitudinally in the range of approximately 10 to 500 microns peak-to-peak, for example, and in some instances in the range of approximately 20 to 200 microns, at a predetermined vibratory frequency $f_o$ of approximately 50 kHz, for example. Vibrating ultrasonic blade (128) may be positioned in direct contact with tissue, with or without assistive clamping force provided by clamp arm (130), to impart ultrasonic vibrational energy to the tissue and thereby cut and/or seal the tissue. For example, blade (128) may cut through tissue clamped between clamp arm (130) and a clamping side of blade (128), or blade (128) may cut through tissue positioned in contact with an oppositely disposed non-clamping side of blade (128) having an edge, for example during a "back-cutting" movement. In some versions, waveguide (138) may be configured to amplify the ultrasonic vibrations delivered to blade (128). Waveguide (138) may include various features operable to control the gain of the vibrations, and/or features suitable to tune waveguide (138) to a selected resonant frequency.

Figure 7:
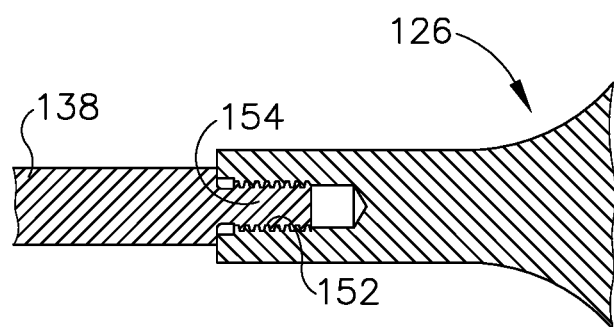
FIG. 7 depicts a partially schematic enlarged side view of a threaded coupling between the ultrasonic transducer and the waveguide of FIG. 6.

In the present example, ultrasonic transducer (26) includes a first resonator (or "end-bell") (145), a conically shaped second resonator (or "fore-bell") (146), and a transduction portion arranged between end-bell (145) and fore-bell (146) that includes a plurality of piezoelectric elements (148). A compression bolt (not shown) extends distally, coaxially through end-bell (145) and piezoelectric elements (148), and is threadedly received within a proximal end of fore-bell (146). A velocity transformer (or "horn") (150) extends distally from fore-bell (146) and includes an internally threaded bore (152) configured to receive and threadedly couple with an externally threaded proximal tip (154) of waveguide (38) as shown in FIGS. 6-7.

While the teachings herein are disclosed in connection with ultrasonic surgical instruments, it will be appreciated that they may also be employed in connection with surgical instruments configured to provide a combination of ultrasonic and radio frequency (RF) energies. Examples of such instruments and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 9,949,385 on Apr. 24, 2018, the disclosure of which is incorporated by reference herein; and U.S. Pub. No. 2017/0000541, entitled "Surgical Instrument with User Adaptable Techniques," published Jan. 5, 2017, the disclosure of which is incorporated by reference herein.

III. Exemplary Transducer Power Circuit

FIGS. 8A-8B illustrate a diagrammatic representation of the surgical instrument (110) having a transducer power circuit (160) electrically connected generator (50). As discussed above, first modular assembly is shown with handle assembly (112) supporting ultrasonic transducer (126) therein and includes trigger (124). In the present example, trigger (124) is electrically connected within transducer power circuit (160) as a trigger activation switch (162), which is selectively opened or closed by the operator during use. Generator (50), ultrasonic transducer (126), and trigger activation switch (162) are thus electrically connected in transducer power circuit (160) to selectively power ultrasonic transducer (126) with generator (50). Trigger activation switch (162) is biased toward an opened position such that transducer power circuit (160) is open and, in turn, inhibits electrical power from powering ultrasonic transducer (126) as shown in FIG. 8A. However, the operator manipulates trigger (124) to selectively close trigger activation switch (162), thereby closing transducer power circuit (160) to allow electrical power to flow through transducer power circuit (160) and power ultrasonic transducer (126) in operation as shown in FIG. 8B. While the present example of trigger activation switch (162) is binarily opened or closed, alternative trigger activation switches may include some gradient between fully opened and fully closed for providing variable power. In any case, the trigger activation switch (162) is not intended to be unnecessarily limited to the particular example shown and described herein. While transducer power circuit (160) is described with respect to surgical instrument (110), it will be appreciated that transducer power circuit (160) may be similarly incorporated into surgical instrument (10).

IV. Alternative Exemplary Ultrasonic Surgical Instruments and Various Electronic Lockouts Given that various portions of ultrasonic surgical instrument (10, 110) removably connect together, it may be desirable in various examples to reuse some portions of ultrasonic surgical instrument (10, 110) while replacing others upon reconnection for further use by the surgeon. For example, first modular assembly (12, 112) in the present example is reusable whereas second modular assembly (14, 114) may be disconnected and replaced with an unused, second modular assembly (14, 114). In some examples, the replacement second modular assembly (14, 114) mechanically connects to first modular assembly (12, 112) such that the operator may use ultrasonic surgical instrument (10, 110) despite not be properly aligned in a relative predetermined alignment. Such predetermined alignment between first and second modular assemblies (12, 112, 14, 114) is generally preferred in order to provide the greatest likelihood of an efficient, effective, and positive outcome for the patient.

Ultrasonic surgical instruments (310, 410, 510, 610, 910, 1010, 1110, 1310, 1410, 1510, 1610, 1710, 1810, 1910, 2110) described below each include at least one of various electronic lockouts (168, 416, 516, 616, 716, 816, 916, 1016, 1116, 1216, 1316, 1416, 1516, 1616, 1716, 1816, 1916, 2016, 2116) having respective modular electrical couplings (176, 427, 527, 627, 727, 827, 927, 1027, 1127, 1227, 1327, 1427, 1527, 1627, 1727, 1827, 1927, 2027, 2127). Generally, each electronic lockout (168, 416, 516, 616, 716, 816, 916, 1016, 1116, 1216, 1316, 1416, 1516, 1616, 1716, 1816, 1916, 2016, 2116) is configured to inhibit, and more particularly prevent, operation of ultrasonic transducers (36, 126) when first modular assemblies (312, 412, 512, 612, 912, 1012, 1112, 1312, 1412, 1512, 1612, 1712, 1812, 1912, 2112) are respectively misaligned from the predetermined alignment with second modular assemblies (314, 414, 514, 614, 914, 1014, 1114, 1314, 1414, 1514, 1614, 1714, 1814, 1914, 2114). Such inhibition of operation by electronic lockouts (168, 416, 516, 616, 716, 816, 916, 1016, 1116, 1216, 1316, 1416, 1516, 1616, 1716, 1816, 1916, 2016, 2116) is referred to herein as a "locked-out state." Once first modular assemblies (312, 412, 512, 612, 912, 1012, 1112, 1312, 1412, 1512, 1612, 1712, 1812, 1912, 2112) are mechanically connected to second modular assemblies (314, 414, 514, 614, 914, 1014, 1114, 1314, 1414, 1514, 1614, 1714, 1814, 1914, 2114) in the predetermined alignment, electronic lockouts (168, 416, 516, 616, 716, 816, 916, 1016, 1116, 1216, 1316, 1416, 1516, 1616, 1716, 1816, 1916, 2016, 2116) allow for operation of ultrasonic transducers (36, 126) in an "operational state."

Figure 9A:
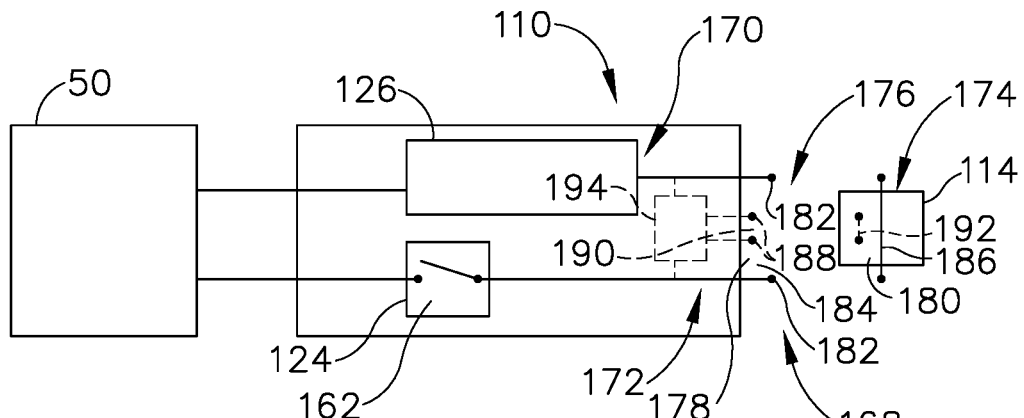
FIG. 9A depicts a diagrammatic view of another example of a transducer power circuit in a selectively opened position and further including a first example of an electrical lockout with a first modular electrical coupling having a modular circuit portion electrically disconnected from a remainder of the transducer power circuit such that the transducer power circuit inhibits electrical flow in a locked-out state.
Figure 9B:
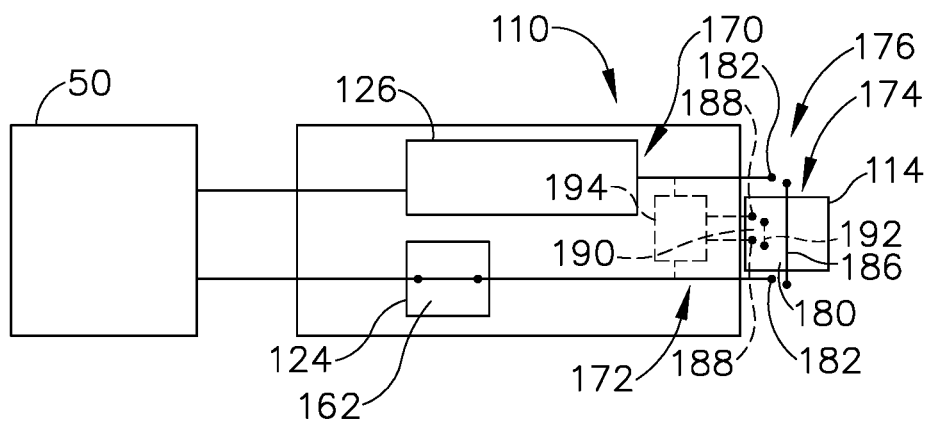
FIG. 9B depicts the diagrammatic view of the transducer power circuit similar to FIG. 9A, but in a selectively closed position and the modular circuit portion misaligned such that the modular circuit portion remains electrically disconnected from the remainder of the transducer power circuit to continue inhibiting electrical flow in the locked out state.

To this end, FIGS. 9A-9B show a diagrammatic representation of an electrical lockout (168) and another example of a transducer power circuit (170). In the present example, first modular assembly includes handle assembly (112) and a first lockout portion (172) of electrical lockout (168), whereas second modular assembly includes shaft assembly (114) and a second lockout portion (174) of electrical lockout (168). Electrical lockout (168) more particularly includes a first modular electrical coupling (176) integrated into transducer power circuit (170) between handle assembly (112) and shaft assembly (114) to inhibit electrical flow to ultrasonic transducer (126) in the locked-out state, but allow electrical flow to ultrasonic transducer (126) in the operational state.

First lockout portion (172) positioned on handle assembly (112) includes a first electrical connection (178), and second lockout portion (174) positioned on shaft assembly (114) includes a second electrical connection (180). First electrical connection (178) is generally fixed relative to the handle assembly (112), and second electrical connection (18) is generally fixed relative to shaft assembly (114) such that first and second electrical connections align in complementary positions when handle assembly (112) and shaft assembly (114) mechanically connect in the predetermined alignment for the operational state. However, first and second electrical connections do not align when handle assembly (112) and shaft assembly (114) are misaligned from the predetermined alignment in the locked-out state.

In the present example, first electrical connection (178) of modular electrical coupling (176) includes a first pair of electrical contacts (182) defining a first electrical gap (184) therebetween such that transducer power circuit (170) is open in the locked-out state. Second electrical connection (180) of modular electrical coupling (176) includes a first electrical shunt (186) configured to electrically connect the first pair of electrical contacts (182) to close transducer power circuit (170) in the operational state upon the predetermined alignment between handle and shaft assemblies (112, 114).

Additionally, first electrical connection (178) of modular electrical coupling (176) may further include a second pair of electrical contacts (188) defining a second electrical gap (190) therebetween such that transducer power circuit (170) is further open in the locked-out state. Second electrical connection (180) of modular electrical coupling (176) thus may further include a second electrical shunt (192) configured to electrically connect the second pair of electrical contacts (188) to close transducer power circuit (170) in the operational state upon the predetermined alignment between handle and shaft assemblies (112, 114). Such dual first and second pairs of electrical contacts (182, 188) may further ensure alignment between handle and shaft assemblies (112, 114) in the predetermined alignment.

Electrical lockout (168) may alternatively or additionally include a controller (194) connected to first and/or second electrical connections (178, 180) and, more particularly, to one or more electrical contacts (182, 188). By way of example, first lockout portion (172) may include controller (194) electrically connected in transducer power circuit (170). Controller (194) detects the operative connection of second electrical connection (180) of second modular assembly, such as shaft assembly (114). When handle and shaft assemblies (112, 114) are misaligned, controller (194) directs transducer power circuit (170) to the locked-out state. However, upon detection, controller (194) directs transducer power circuit (170) to the operational state. Thus, transducer power circuit (170) may not be an electrically open circuit, as discussed above in a prior example, but may rather apply a logic to select the locked-out or operational state. For example, first and second electrical connections (178, 180) may be metallic members with controller (194) operatively connected thereto to detect changes in capacitance for selecting the locked-out or operational state. By way of further example, first electrical connection (170) may be an electrical coil, whereas second electrical connection (180) may be a magnet such that controller (194) is configured to detect changes in inductance for selecting the locked-out state or operational state. Controller (194) may be further configured to detect infrared light and/or positions of additional components to select between the locked-out or operational states. These examples and others will be more readily appreciated in view of the various examples discussed below.

As discussed above, first modular assembly includes handle assembly (112) and second modular assembly includes shaft assembly (114) with respect to ultrasonic surgical instrument shown in FIGS. 3-7. Alternatively, with respect to FIGS. 1-2, first modular assembly may include handle assembly (26) and shaft assembly (28), whereas second modular assembly may include clamp arm assembly (68). Distinctions between modular assemblies may thus vary with one or more modular electrical couplings (176) configured to connect modular assemblies in the predetermined alignment for operation.

While the following electrical lockouts (168, 416, 516, 616, 716, 816, 916, 1016, 1116, 1216, 1316, 1416, 1516, 1616, 1716, 1816, 1916, 2016, 2116) are shown in distinct positions between reusable and replaceable features for removable connection, it will be appreciated that electrical lockouts (168, 416, 516, 616, 716, 816, 916, 1016, 1116, 1216, 1316, 1416, 1516, 1616, 1716, 1816, 1916, 2016, 2116) may be incorporated into any surgical instrument described herein, exchanged, or moved so as to make one or more portions of a surgical instrument removable from a remainder of the surgical instrument. To this end, other suitable kinds of clamp arm assemblies and/or shaft assemblies may be used to provide different kinds of modular assemblies will be apparent to those of ordinary skill in the art in view of the teachings herein. Various mechanical lockouts may be similarly incorporated into any surgical instrument in conjunction with the following electrical lockouts (168, 416, 516, 616, 716, 816, 916, 1016, 1116, 1216, 1316, 1416, 1516, 1616, 1716, 1816, 1916, 2016, 2116). Such mechanical lockouts are disclosed in U.S. application Ser. No. 15/951,773, entitled "Mechanical Lockout for Ultrasonic Surgical Instrument," filed on Apr. 12, 2018, issued as U.S. Pat. No. 10,945,755 on Mar. 16, 2021, the disclosure of which is incorporated by reference herein.

The following description provides various examples of electrical lockouts (168, 416, 516, 616, 716, 816, 916, 1016, 1116, 1216, 1316, 1416, 1516, 1616, 1716, 1816, 1916, 2016, 2116). Such electrical lockouts (168, 416, 516, 616, 716, 816, 916, 1016, 1116, 1216, 1316, 1416, 1516, 1616, 1716, 1816, 1916, 2016, 2116) described below may be used with any ultrasonic surgical instrument described above and below and in any of the various procedures described in the various patent references cited herein. To this end, like numbers below indicated like features described above. Except as otherwise described below, ultrasonic surgical instruments (310, 410, 510, 610, 910, 1010, 1110, 1310, 1410, 1510, 1610, 1710, 1810, 1910, 2110) described below may be constructed and operable like instruments (10, 110) described above. Certain details of ultrasonic surgical instruments (310, 410, 510, 610, 910, 1010, 1110, 1310, 1410, 1510, 1610, 1710, 1810, 1910, 2110) will therefore be omitted from the following description, it being understood that such details are already provided above in the description of instruments (10, 110). Other suitable ways in which various ultrasonic surgical instruments may be used will be apparent to those of ordinary skill in the art in view of the teachings herein.

Figure 10:
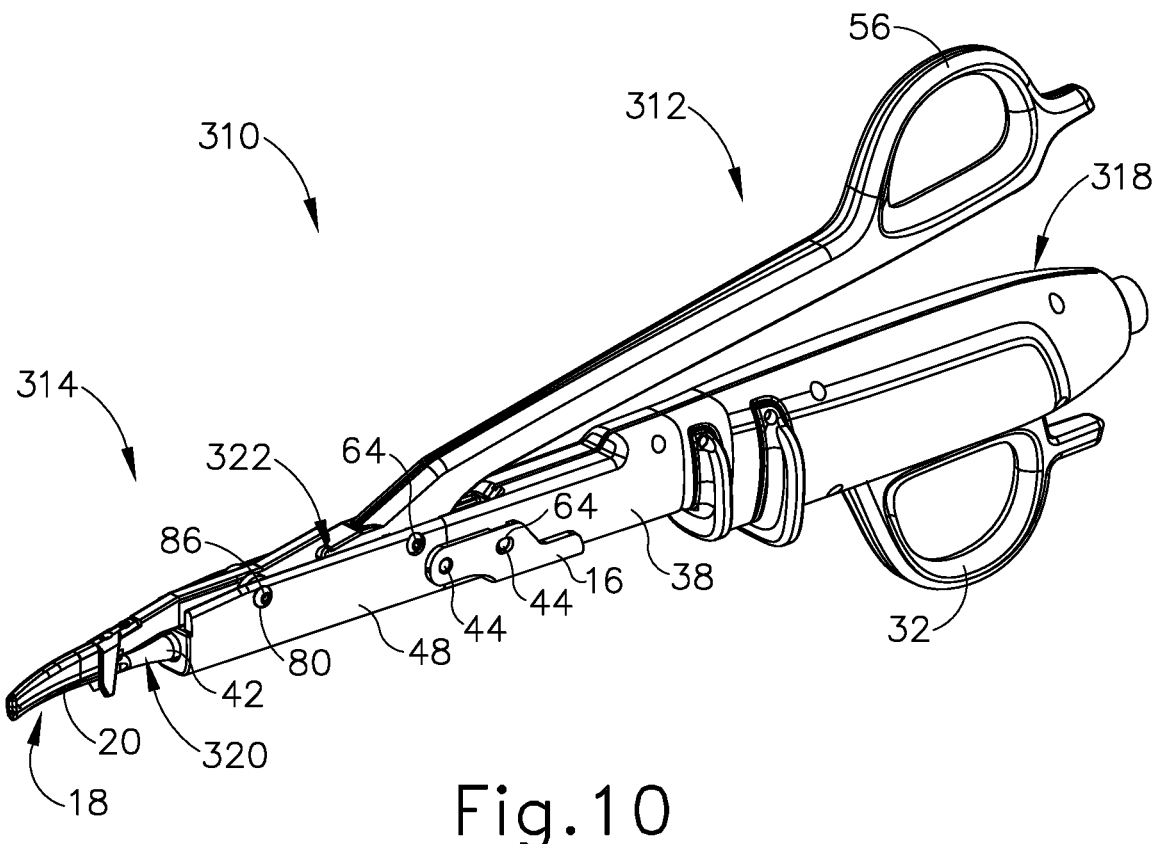
FIG. 10 depicts a schematic, perspective view of a third exemplary surgical instrument having the electrical lockout with the modular electrical coupling of FIG. 9A-9C such that the surgical instrument is in the operational state.
Figure 11:
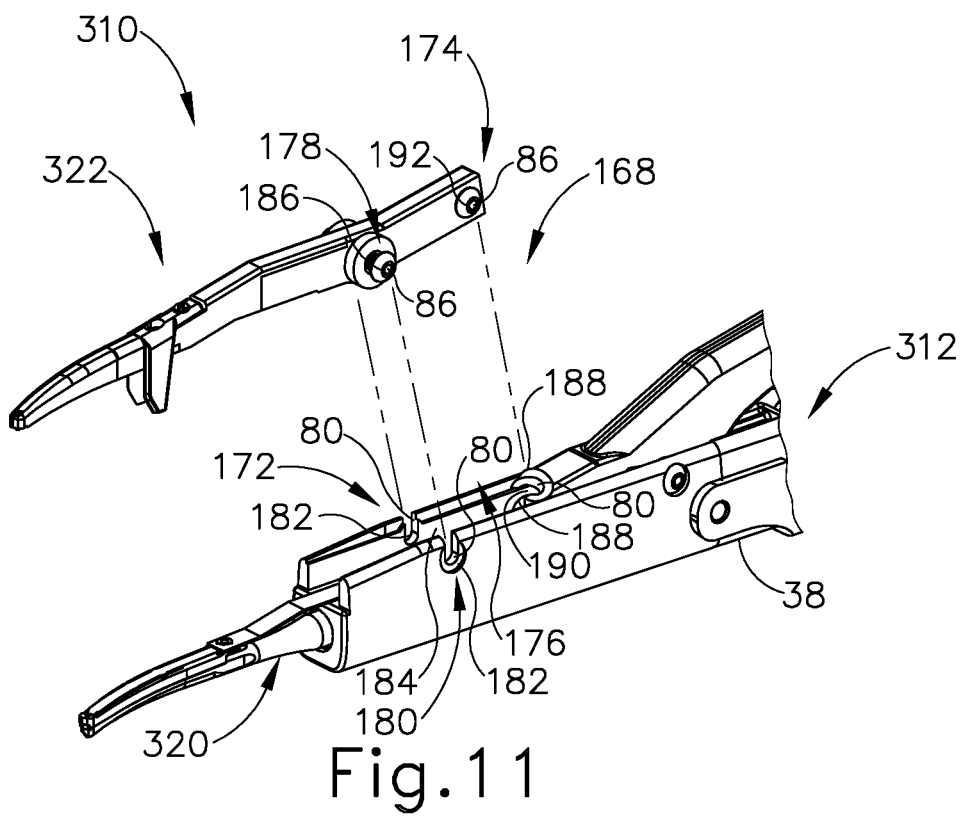
FIG. 11 depicts a schematic, enlarged perspective view of the surgical instrument of FIG. 10 with a clamp arm assembly mechanically and electrically disconnected from a remainder of the surgical instrument in the locked-out state.

A. Third Exemplary Ultrasonic Surgical Instrument Having a First Example of an Electrical Lockout FIGS. 10-11 show a third exemplary ultrasonic surgical instrument (310) including a first modular assembly (312), a second modular assembly (314), and a first example of electrical lockout (168) for inhibiting misaligned use of surgical instrument (310) in the locked-out state. In the present example, first modular assembly (312) has a handle assembly (318) and a distally extending shaft assembly (320), whereas, second modular assembly (314) has a clamp arm assembly (322). Electrical lockout (316) has first lockout portion (172) positioned on a distal portion of handle assembly (318) and second lockout portion (174) positioned on a proximal portion of clamp arm assembly (322). First and second lockout portions (424, 426) collectively define first modular electrical coupling (176) and cooperatively align as clamp arm assembly (322) mechanically connects to handle assembly (318) with a predetermined alignment to direct transducer power circuit (170) (see FIGS. 9A-9C) from the locked-out state to the operational state.

With respect to FIG. 11, first lockout portion (172) includes first electrical connection (178) with first pair of electrical contacts (182) and second pair of electrical contacts (188). Second lockout portion (174) includes second electrical connection (180) including first and second electrical shunts (186, 192). More particularly, first pair of electrical contacts (182) are positioned on laterally opposing distal bores (80), while second pair of electrical contacts (188) are positioned on laterally opposing proximal bores (80). Similarly, first electrical shunt (186) is positioned on distal pin (86) and second electrical shunt (192) is position on proximal pin (86). First electrical shunt (186) is configured to be received in first electrical gap (184) between first pair of electrical contacts (188), and second electrical shunt (192) is configured to be received in second electrical gap (190) between second pair of electrical contacts (188). In the present example, each first and second pair of electrical contacts (182, 188) with electrical gaps (190) is a distinct circuit to close for use. First and second electrical shunts (186, 192) electrically connect first and second pair of electrical contacts (182, 188) respectively upon mechanical connection of clamp arm assembly (322) to handle assembly (318) in predetermined alignment. Thereby, electrical lockout (316) transitions surgical instrument (310) from the incomplete and/or misaligned locked-out state to the operational state as discussed above with respect to transducer power circuit (170) of FIGS. 9A-9C.

Figure 12:
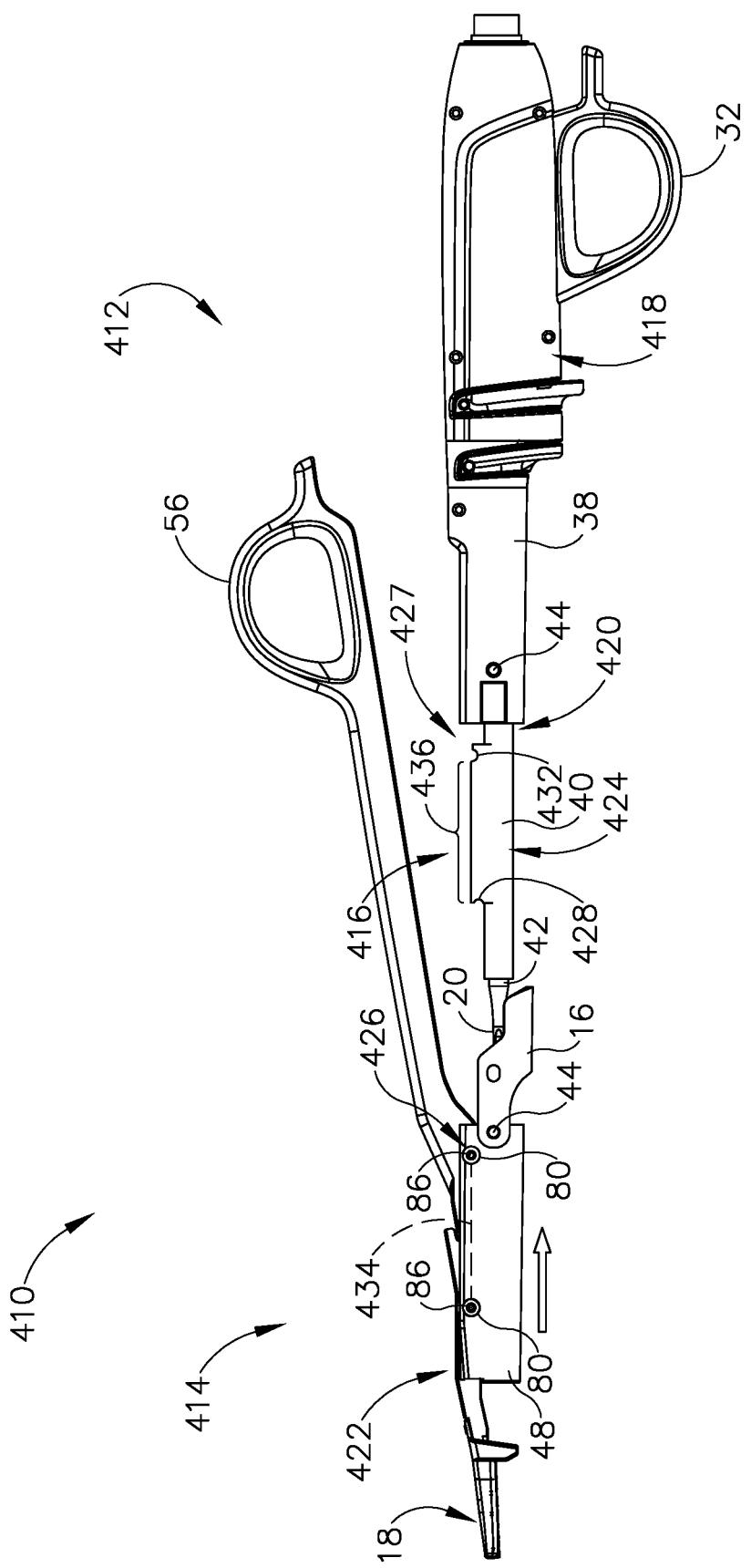
FIG. 12 depicts an elevational side view of a fourth exemplary surgical instrument having a second example of an electrical lockout with a second modular electrical coupling such that the surgical instrument is in a locked-out state.
Figure 13:
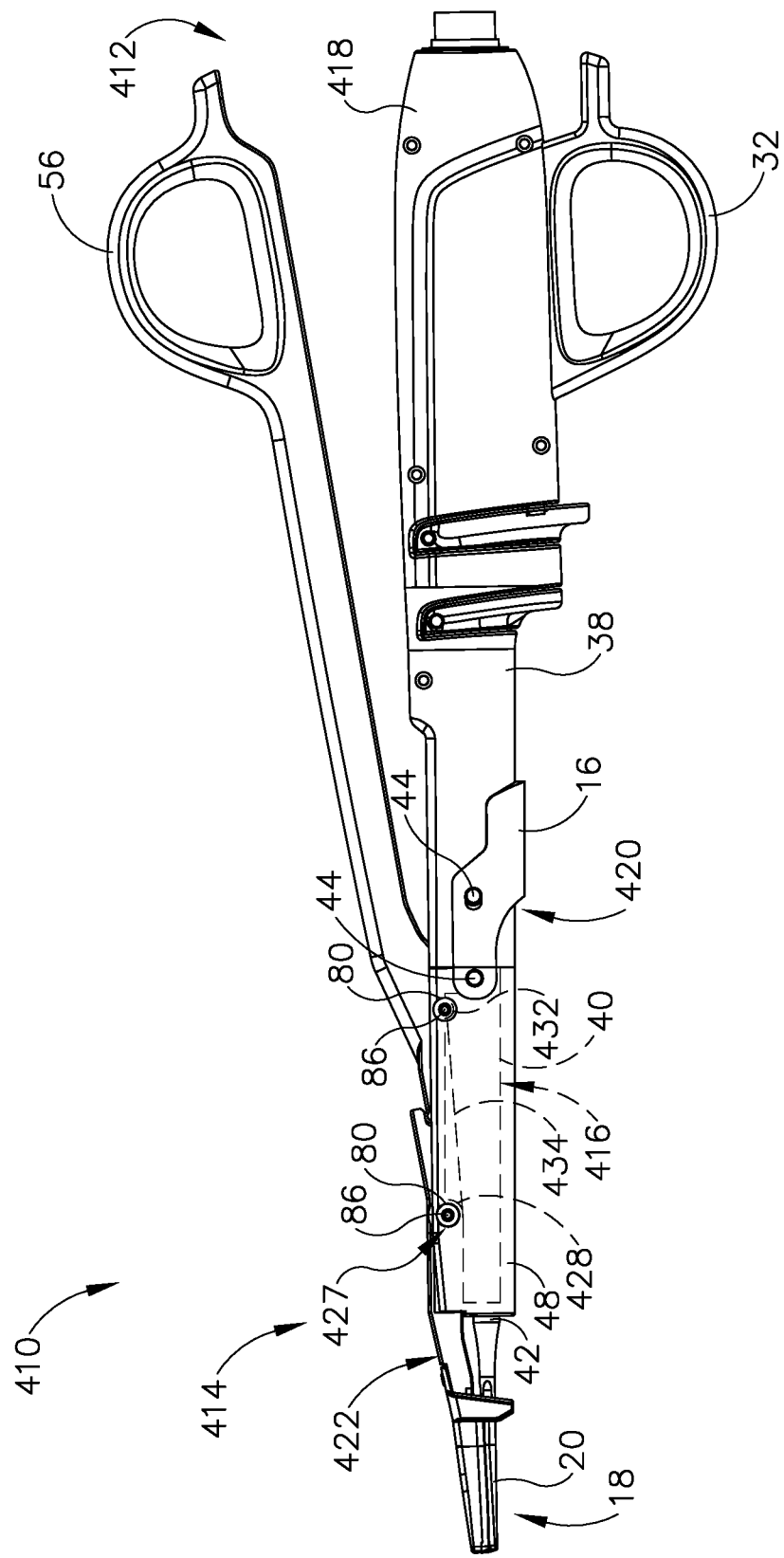
FIG. 13 depicts a schematic, elevational side view of the surgical instrument of FIG. 12 in an operational state.
Figure 14:
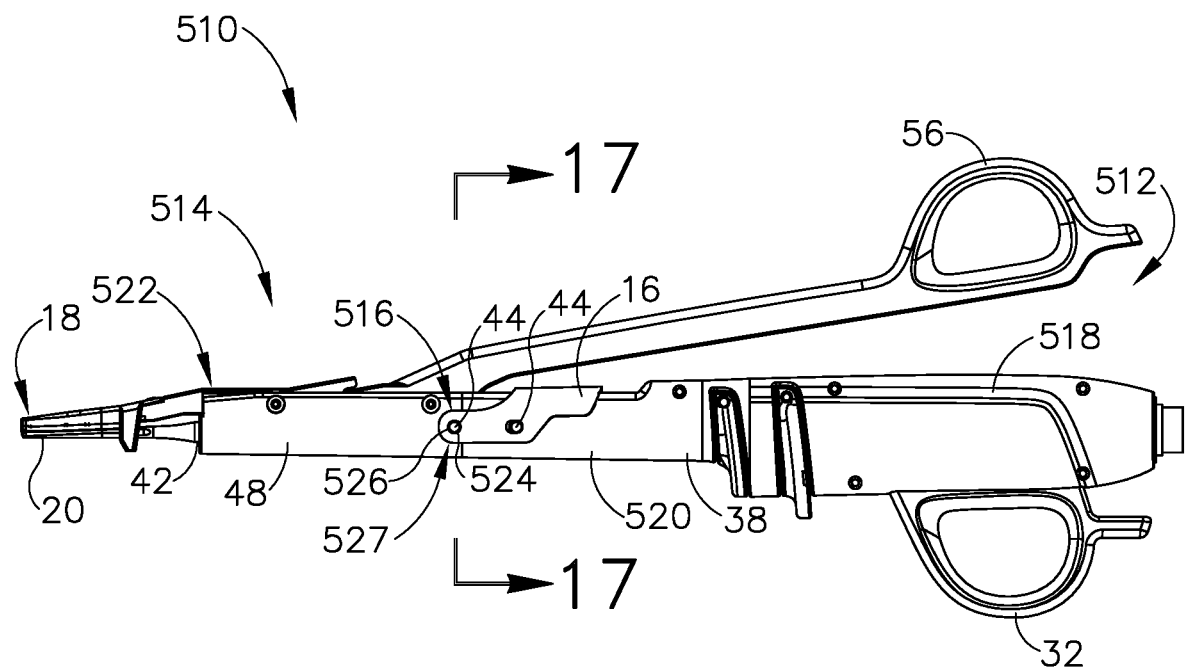
FIG. 14 depicts a schematic, elevational side view of a fifth exemplary surgical instrument having a third example of an electrical lockout with a third modular electrical coupling such that the surgical instrument is an operational state.

B. Fourth Exemplary Ultrasonic Surgical Instrument Having a Second Example of an Electrical Lockout FIGS. 12-13 show a fourth exemplary ultrasonic surgical instrument (410) including a first modular assembly (412), a second modular assembly (414), and a second example of an electrical lockout (416) for inhibiting misaligned use of surgical instrument (410) in a locked-out state. In the present example, first modular assembly (412) has a handle assembly (418) and a distally extending shaft assembly (420), whereas second modular assembly (414) has a clamp arm assembly (422). Electrical lockout (416) has a first lockout portion (424) positioned on a distal portion of handle assembly (418) and a second lockout portion (426) positioned on a proximal portion of clamp arm assembly (422). First and second lockout portions (424, 426) collectively define a second modular electrical coupling (427) and cooperatively align as clamp arm assembly (422) mechanically connects to handle assembly (418) with a predetermined alignment to direct surgical instrument (410) from the locked-out state to the operational state.

With respect to FIG. 12, first lockout portion (424) includes a first electrical connection (428) with a pair of electrical contacts (430). Second lockout portion (426) includes a second electrical connection (432) including an electrical shunt (434). More particularly, distal and proximal electrical contacts (430) extend transversely upward from tube (40). Similarly, electrical shunt (434) extends from distal pin (86) to proximal pin (86) across an electrical gap (436). Distal pin (86) of electrical shunt (434) is configured to be received against distal electrical contact (430), while proximal pin (86) of electrical shunt (434) is configured to be received against proximal electrical contact (430) such that electrical shunt (434) electrically connects electrical contacts (430). Electrical shunt (434) electrically connects electrical contacts (430) upon mechanical connection of clamp arm assembly (422) to handle assembly (418) in the predetermined alignment shown in FIG. 13. Thereby, electrical lockout (416) transitions surgical instrument (410) from the incomplete and/or misaligned locked-out state to the operational state as discussed above with respect to transducer power circuit (170) of FIGS. 9A-9C.

C. Fifth Exemplary Ultrasonic Surgical Instrument Having a Third Example of an Electrical Lockout FIGS. 14-17 show a fifth exemplary ultrasonic surgical instrument (510) including a first modular assembly (512), a second modular assembly (514), and a third example of an electrical lockout (516) for inhibiting misaligned use of surgical instrument (510) in a locked-out state. In the present example, first modular assembly (512) has a handle assembly (518) and a distally extending shaft assembly (520), whereas second modular assembly (514) has a clamp arm assembly (522). Electrical lockout (516) has a first lockout portion (524) positioned on a distal portion of handle assembly (518) and a second lockout portion (526) positioned on a proximal portion of clamp arm assembly (522). First and second lockout portions (524, 526) collectively define a third modular electrical coupling (527) and cooperatively align as clamp arm assembly (522) mechanically connects to handle assembly (518) with a predetermined alignment to direct surgical instrument (510) from the locked-out state to the operational state.

Figure 15:
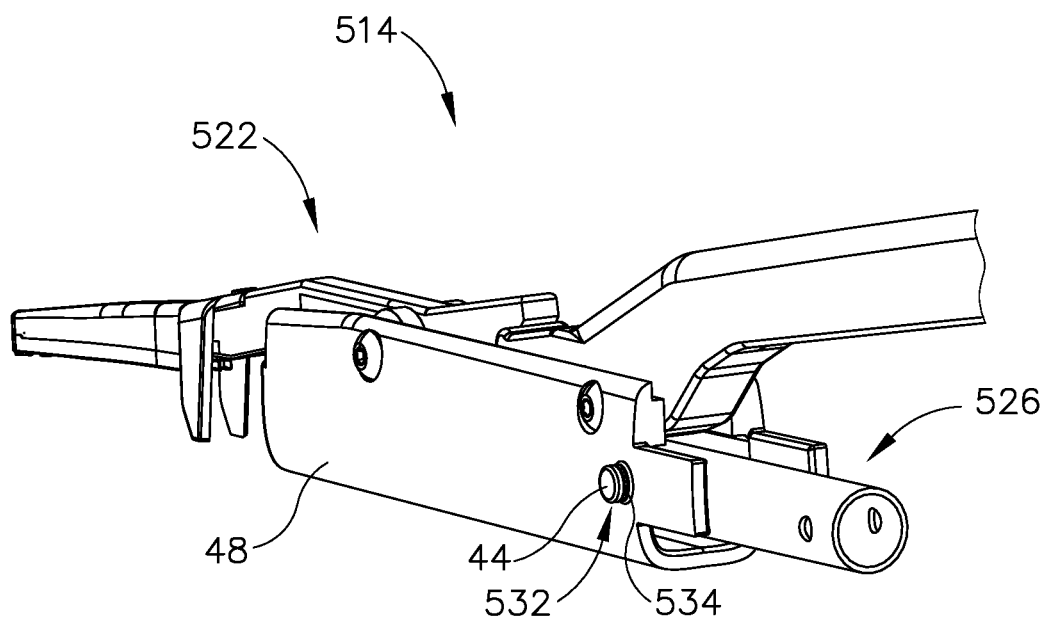
FIG. 15 depicts a schematic, proximal perspective view of a clamp arm assembly of the surgical instrument of FIG. 14 with a portion of the modular electrical coupling.
Figure 16:
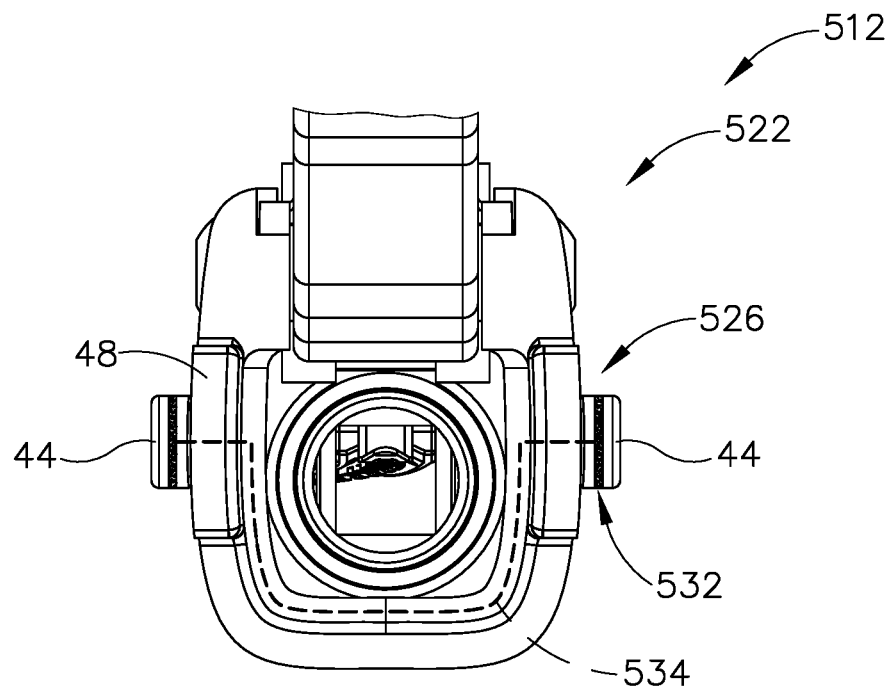
FIG. 16 depicts a schematic, enlarged proximal end view of the clamp arm assembly of FIG. 15 with the portion of the modular electrical coupling.
Figure 17:
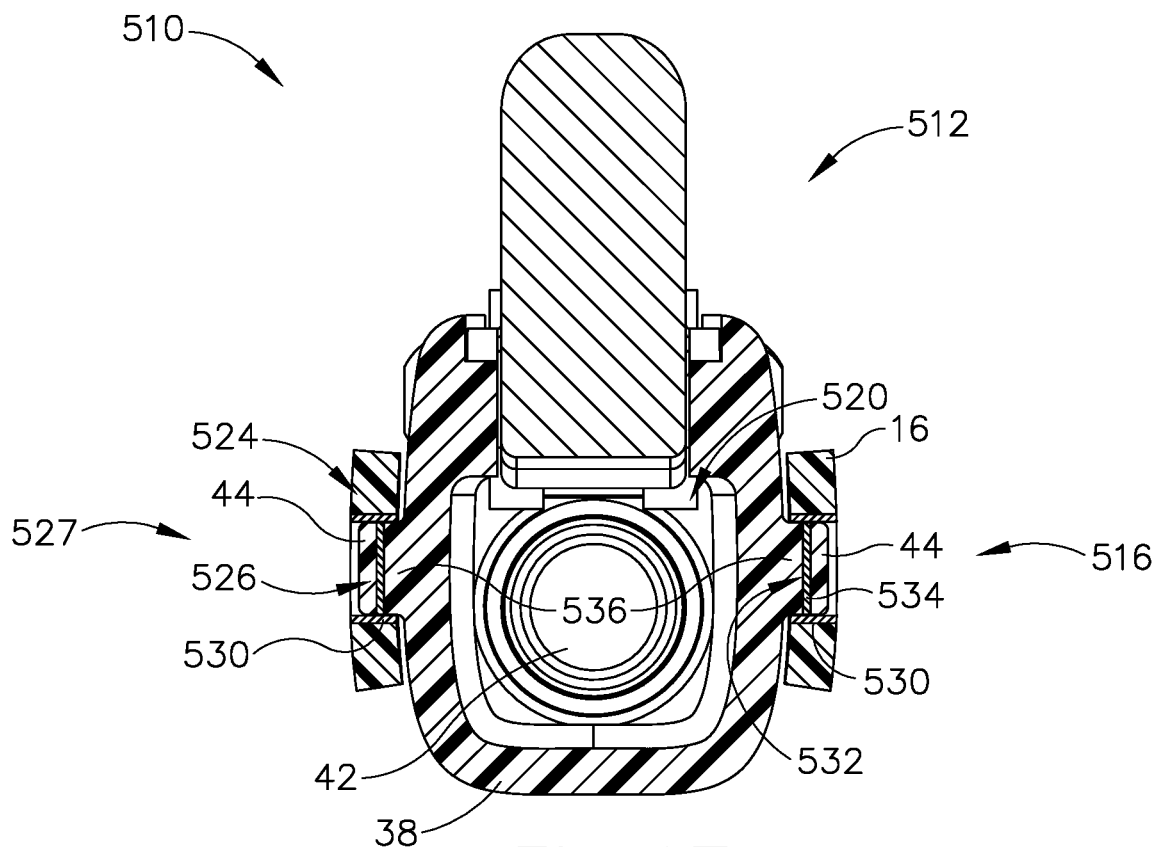
FIG. 17 depicts a schematic, cross-sectional view of the surgical instrument taken along section line 17-17 of FIG. 14 in the operational state.
Figure 18:
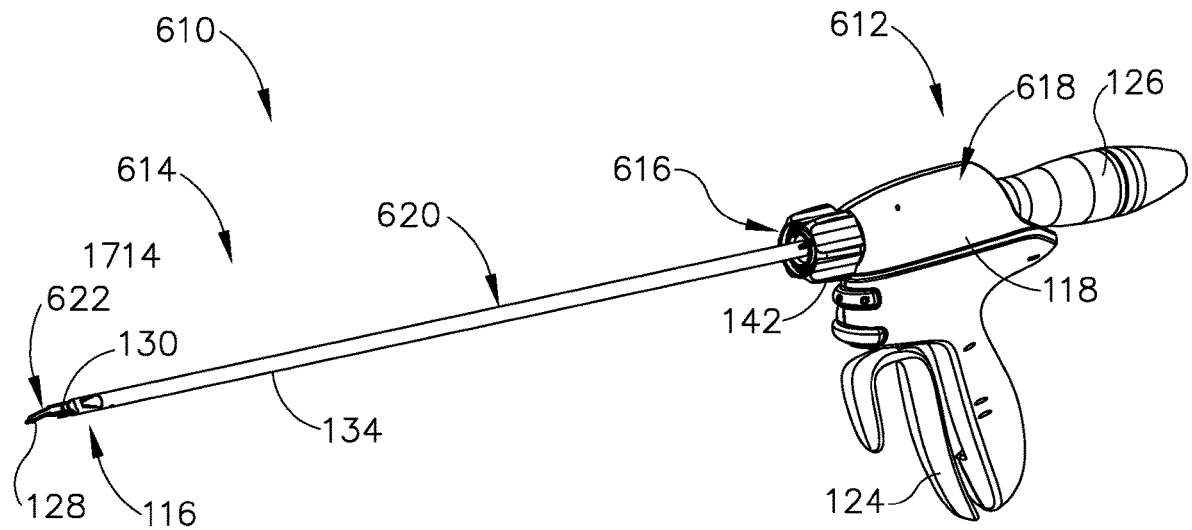
FIG. 18 depicts a schematic, perspective view of a sixth exemplary surgical instrument having a fourth example of an electrical lockout with a fourth modular electrical coupling such that the surgical instrument is in an operational state.
Figure 19:
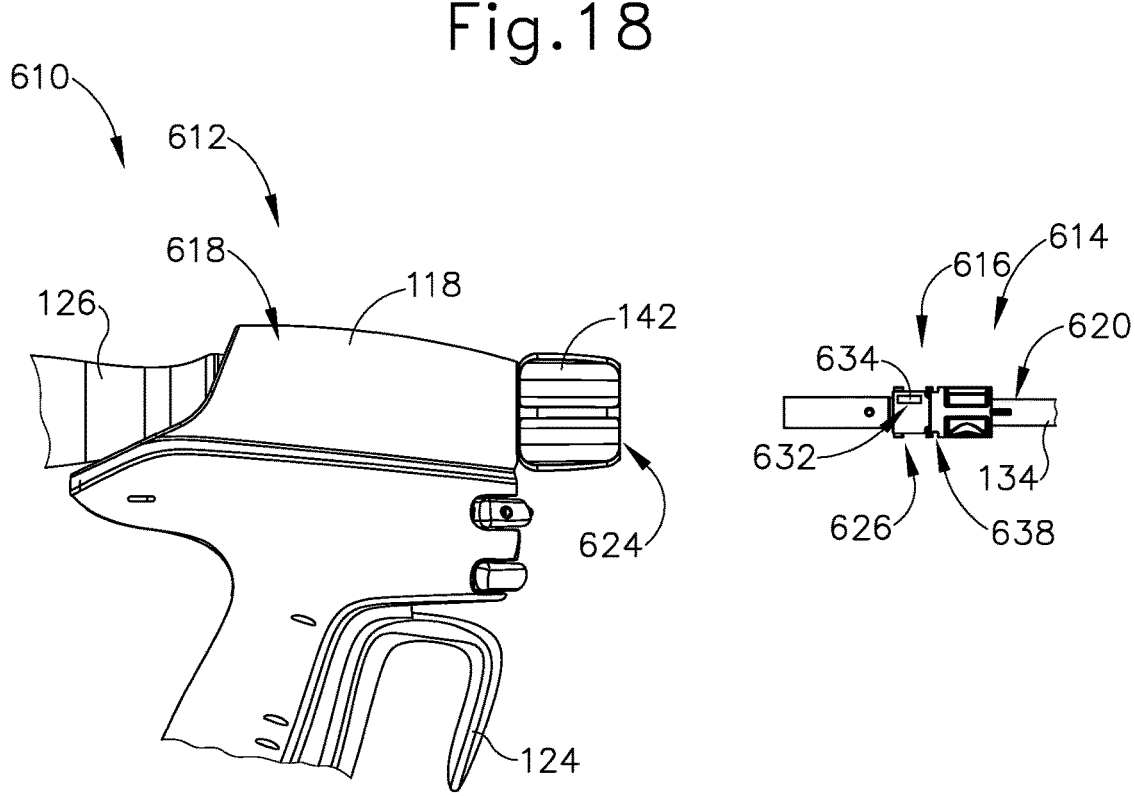
FIG. 19 depicts a schematic, enlarged, elevational side view of the surgical instrument of FIG. 18 with a shaft assembly mechanically and electrically disconnected from a handle assembly in a locked-out state.

With respect to FIGS. 15-17, first lockout portion (524) includes a first electrical connection (528) with a pair of electrical contacts (530). Second lockout portion (526) includes a second electrical connection (532) including an electrical shunt (534). More particularly, electrical contacts (530) are positioned respectively within laterally opposing bores (64) of coupling member (16). Similarly, electrical shunt (534) extends from one lateral protrusion (44) to another opposing lateral protrusion (44) across an electrical gap (536). Protrusions (44) of electrical shunt (534) are configured to be respectively received within bores (64) against respective electrical contacts (530) such that electrical shunt (534) electrically connects electrical contacts (530). Electrical shunt (534) electrically connects electrical contacts (530) upon mechanical connection of clamp arm assembly (522) to handle assembly (518) in the predetermined alignment shown in FIG. 17. Thereby, electrical lockout (516) transitions surgical instrument (510) from the incomplete and/or misaligned locked-out state to the operational state as discussed above with respect to transducer power circuit (170) of FIGS. 9A-9C.

D. Sixth Exemplary Ultrasonic Surgical Instrument Having a Fourth Example of an Electrical Lockout FIGS. 18-20B show a sixth exemplary ultrasonic surgical instrument (610) including a first modular assembly (612), a second modular assembly (614), and a fourth example of an electrical lockout (616) for inhibiting misaligned use of surgical instrument (610) in a locked-out state. In the present example, first modular assembly (612) has a handle assembly (618), whereas second modular assembly (614) has a shaft assembly (620) and a distally extending clamp arm assembly (622). Electrical lockout (616) has a first lockout portion (624) positioned on a distal portion of handle assembly (618) and a second lockout portion (626) positioned on a proximal portion of shaft assembly (620). First and second lockout portions (624, 626) collectively define a fourth modular electrical coupling (627) and cooperatively align as shaft assembly (620) mechanically connects to handle assembly (618) with a predetermined alignment to direct surgical instrument (610) from the locked-out state to the operational state.

Figure 20A:
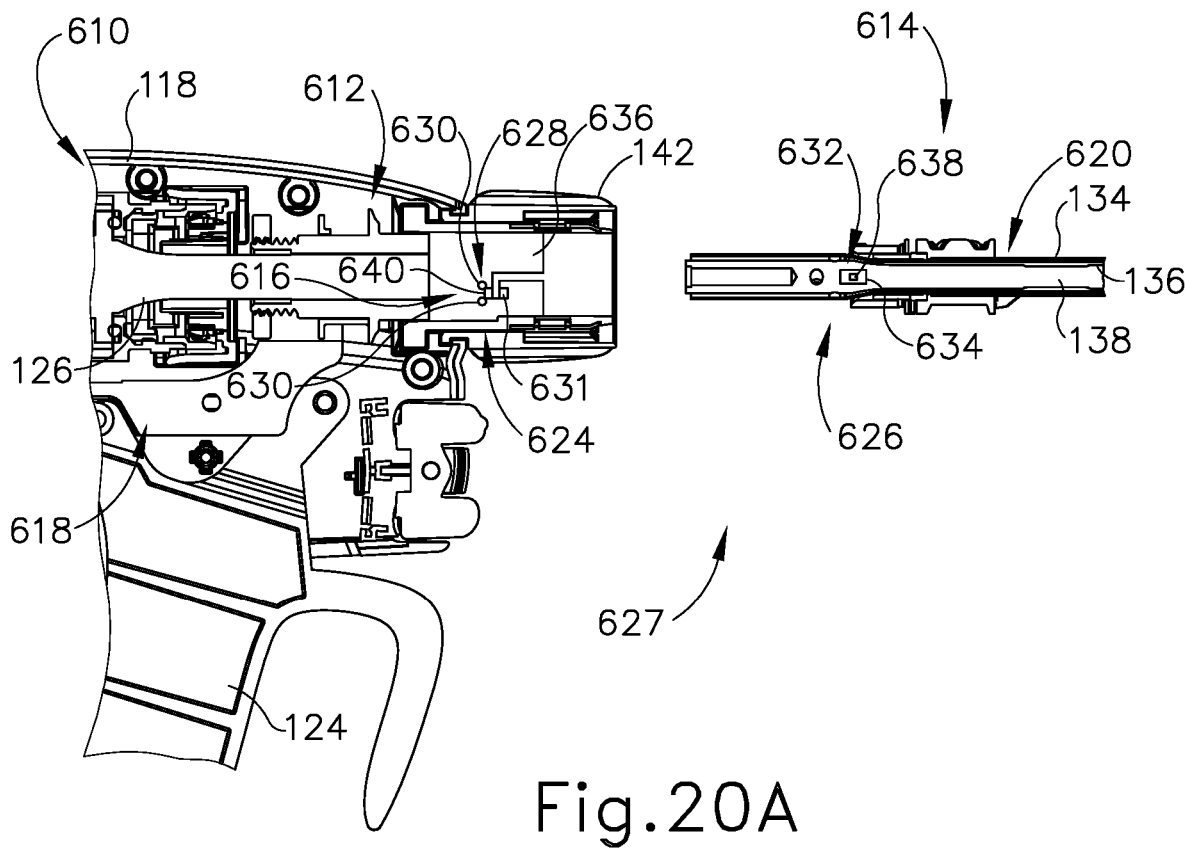
FIG. 20A depicts a schematic, sectional side view of the surgical instrument of FIG. 18 showing the electrical lockout with the modular electrical coupling sensing a capacitance in the locked-out state.
Figure 20B:
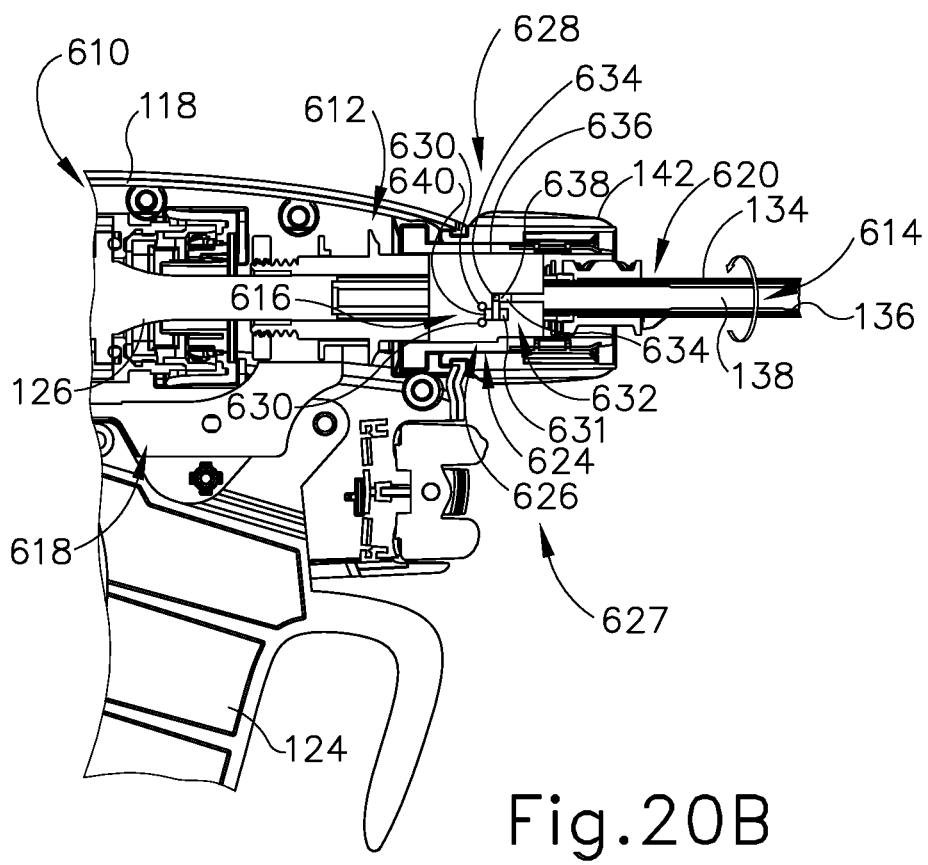
FIG. 20B depicts the schematic, sectional side view of the surgical instrument similar to FIG. 20A, but showing the modular electrical coupling sensing the capacitance in the operational state.

With respect to FIGS. 20A-20B, first lockout portion (624) includes a first electrical connection (628) with a pair of electrical contacts (630) as well as a metallic member, such as a first metallic plate (631). Second lockout portion (626) includes a second electrical connection (632) including a metallic member, such as a second metallic plate (634). More particularly, electrical contacts (630) and first metallic plate (631) are positioned within a female bayonet body coupler (636), whereas second metallic plate (634) is positioned on a male bayonet shaft coupler (638). Electrical contacts (630) are connected to controller (194) (see FIGS. 9A-9C) such that controller (194) (see FIGS. 9A-9C) is configured to detect changes in capacitance across electrical gap (640) between first and second metallic plates (631, 634). Such detection of capacitance changes occur upon mechanical connection of shaft assembly (620) to handle assembly (618) in the predetermined alignment shown in FIG. 20B. Thereby, electrical lockout (616) transitions surgical instrument (610) from the incomplete and/or misaligned locked-out state to the operational state as discussed above with respect to transducer power circuit (170) of FIGS. 9A-9C.

Figure 21:
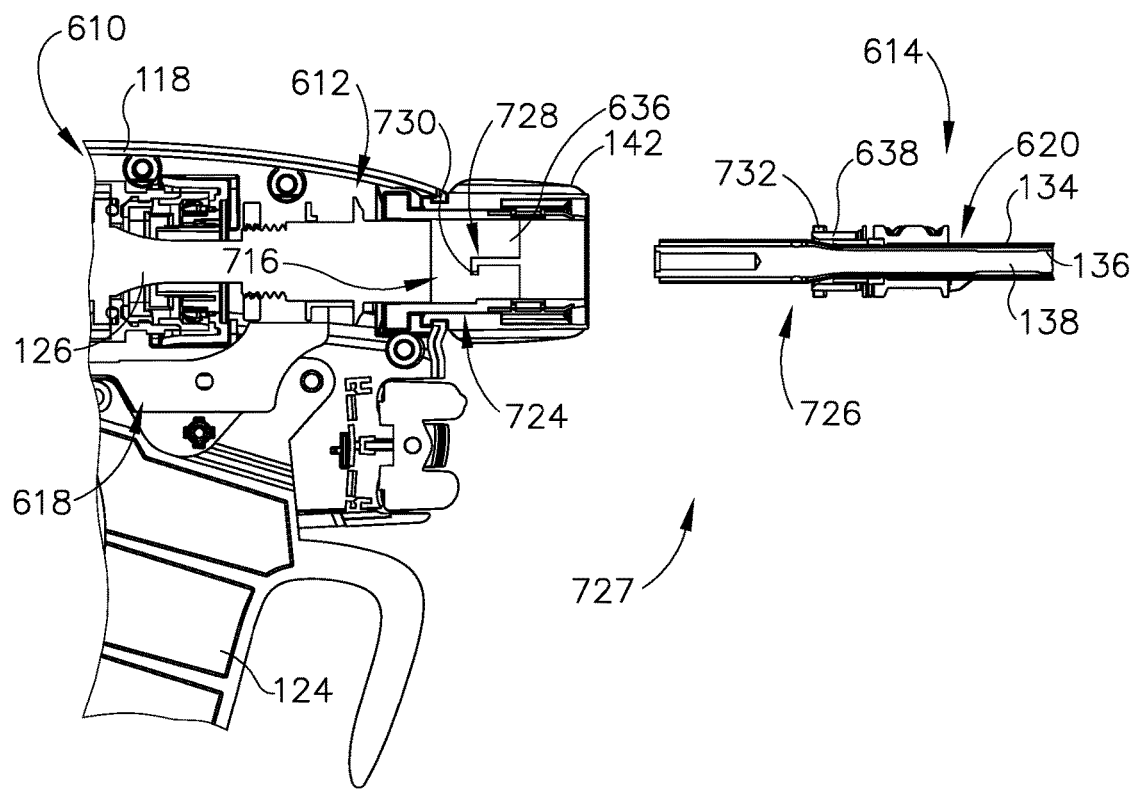
FIG. 21 depicts a schematic, sectional side view of the surgical instrument of FIG. 18 with the shaft assembly mechanically and electrically disconnected from the handle assembly in a locked-out state as well as a fifth example of an electrical lockout with a fifth modular electrical coupling sensing an inductance in the locked-out state.

E. Sixth Exemplary Ultrasonic Surgical Instrument Having a Fifth Example of an Electrical Lockout FIG. 21 shows ultrasonic surgical instruments (610) discussed above with first modular assembly (612) and second modular assembly (614) in conjunction with a fifth example of an electrical lockout (716) including a fifth modular electrical coupling (727). Electrical lockout (716) has a first lockout portion (724) positioned on a distal portion of handle assembly (618) and a second lockout portion (726) positioned on a proximal portion of shaft assembly (620). First lockout portion (724) includes a first electrical connection (728) with an electrical coil (730) operatively connected to controller (194) (see FIGS. 9A-9C). Second lockout portion (726) includes a magnet (732). More particularly, electrical coil (730) is positioned within female bayonet body coupler (636), whereas magnet (734) is positioned on a male bayonet shaft coupler (638). Controller (194) (see FIGS. 9A-9C) is configured to detect changes in inductance as magnet (432) is introduced therein during alignment. Such detection of inductance changes occur upon mechanical connection of shaft assembly (620) to handle assembly (618) in the predetermined alignment. Thereby, electrical lockout (716) transitions surgical instrument (610) from the incomplete and/or misaligned locked-out state to the operational state as discussed above with respect to transducer power circuit (170) of FIGS. 9A-9C.

Figure 22:
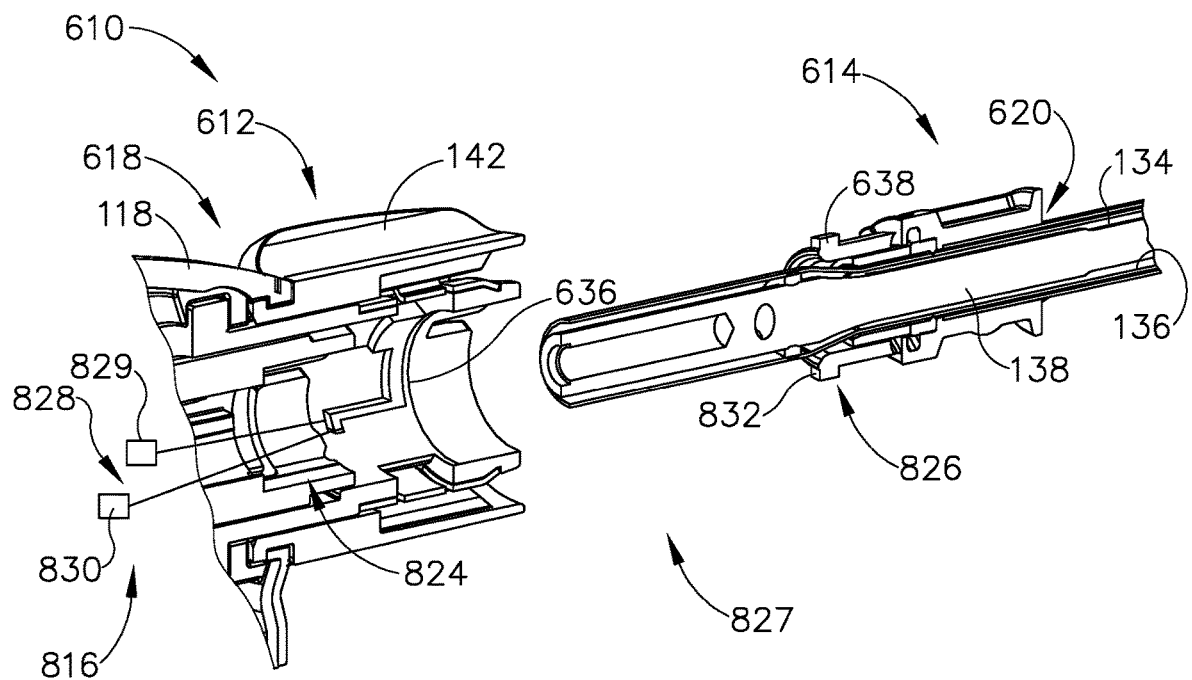
FIG. 22 depicts a schematic, enlarged, sectional perspective view of the surgical instrument of FIG. 18 with the shaft assembly mechanically and electrically disconnected from the handle assembly in a locked-out state as well as a sixth example of an electrical lockout with a sixth modular electrical coupling sensing an infrared signal in the locked-out state.
Figure 23A:
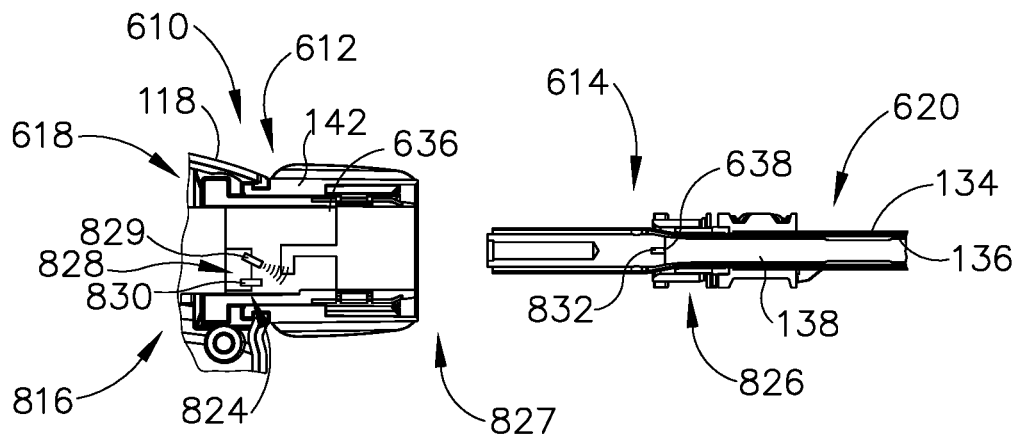
FIG. 23A depicts a schematic, enlarged sectional side view of the surgical instrument of FIG. 22 in the locked-out state with the shaft assembly removed from the handle assembly.
Figure 23B:
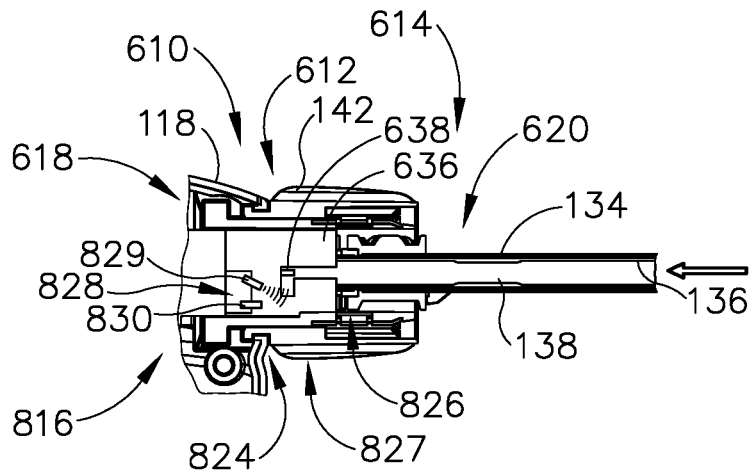
FIG. 23B depicts the schematic, enlarged sectional side view of the surgical instrument in the locked-out state similar to FIG. 23A, but showing the shaft assembly inserted into the handle assembly.
Figure 23C:
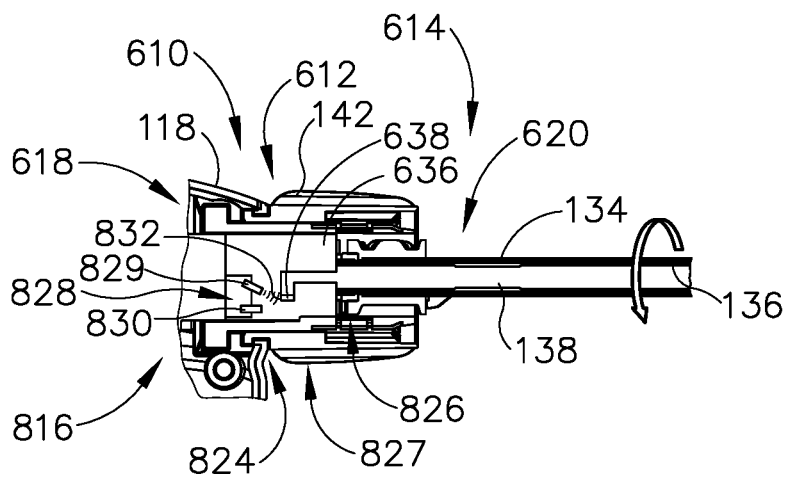
FIG. 23C depicts the schematic, enlarged sectional side view of the surgical instrument similar to FIG. 23B, but showing the electrical lockout and modular electrical coupling sensing the infrared signal in an operational state.
Figure 24:
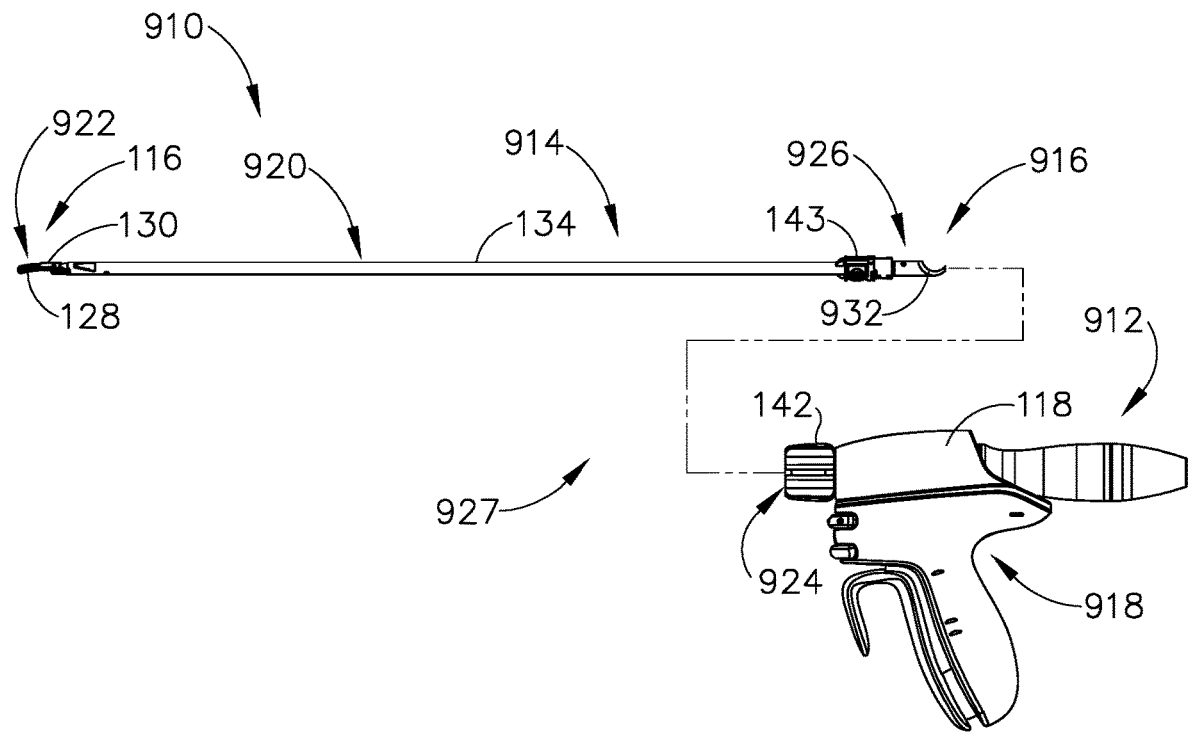
FIG. 24 depicts a schematic, partially exploded, perspective view of a seventh exemplary surgical instrument having a seventh example of an electrical lockout with a seventh modular electrical coupling an a locked-out state.

F. Sixth Exemplary Ultrasonic Surgical Instrument Having a Sixth Example of an Electrical Lockout FIGS. 22-23C show ultrasonic surgical instruments (610) discussed above with first modular assembly (612) and second modular assembly (614) in conjunction with a sixth example of an electrical lockout (816) including a sixth modular electrical coupling (827). Electrical lockout (816) has a first lockout portion (824) positioned on a distal portion of handle assembly (618) and a second lockout portion (826) positioned on a proximal portion of shaft assembly (620). First lockout portion (824) includes a first electrical connection (828) with an infrared light source (829) and an infrared receiver (830) operatively connected to controller (194) (see FIGS. 9A-9C). Second lockout portion (826) includes a reflective surface (832). More particularly, infrared light source and receiver (829, 830) are positioned on female bayonet body coupler (636), whereas reflective surface (834) is positioned on a male bayonet shaft coupler (638). Reflective surface (834) is positioned to direct infrared light from infrared light source (829) into infrared receiver (830) in the predetermined alignment as shown in FIGS. 23A-23C. Controller (194) (see FIGS. 9A-9C) is configured to detect changes in infrared light during alignment. Such detection of infrared light changes occur upon mechanical connection of shaft assembly (620) to handle assembly (618) in the predetermined alignment. Thereby, electrical lockout (816) transitions surgical instrument (610) from the incomplete and/or misaligned locked-out state to the operational state as discussed above with respect to transducer power circuit (170) of FIGS. 9A-9C.

G. Seventh Exemplary Ultrasonic Surgical Instrument Having a Seventh Example of an Electrical Lockout FIGS. 24-27C show a seventh exemplary ultrasonic surgical instrument (910) including a first modular assembly (912), a second modular assembly (914), and a seventh example of an electrical lockout (916) for inhibiting misaligned use of surgical instrument (910) in a locked-out state. In the present example, first modular assembly (912) has a handle assembly (918), whereas second modular assembly (914) has a shaft assembly (920) and a distally extending clamp arm assembly (922). Electrical lockout (916) has a first lockout portion (924) positioned on a distal portion of handle assembly (918) and a second lockout portion (926) positioned on a proximal portion of shaft assembly (920). First and second lockout portions (924, 926) collectively define a seventh modular electrical coupling (927) and cooperatively align as shaft assembly (920) mechanically connects to handle assembly (918) with a predetermined alignment to direct surgical instrument (910) from the locked-out state to the operational state.

Figure 25:
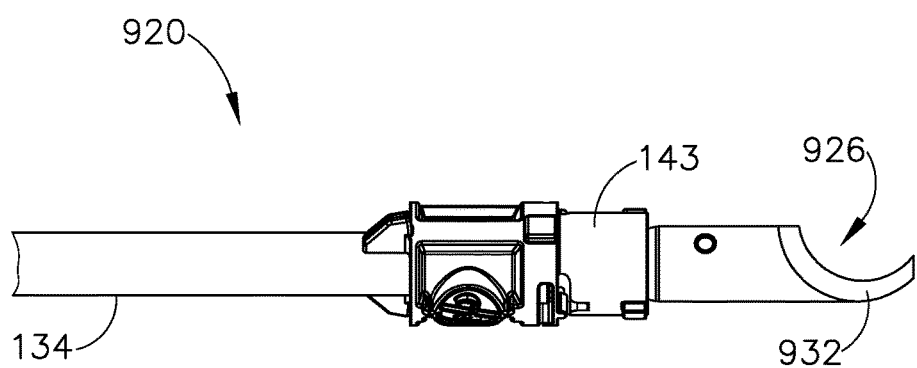
FIG. 25 depicts a schematic, enlarged, elevational side view of a shaft assembly of the surgical instrument of FIG. 24 including a portion of the electrical lockout and modular electrical coupling.
Figure 26:
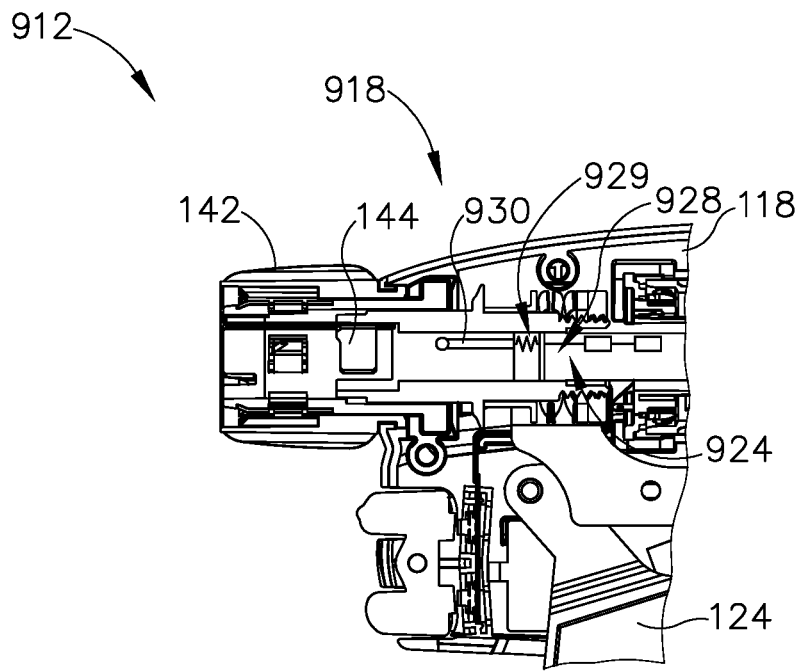
FIG. 26 depicts a schematic, enlarged, sectional view of a handle assembly of the surgical instrument of FIG. 24 including another portion of the electrical lockout and modular electrical coupling.
Figure 27A:
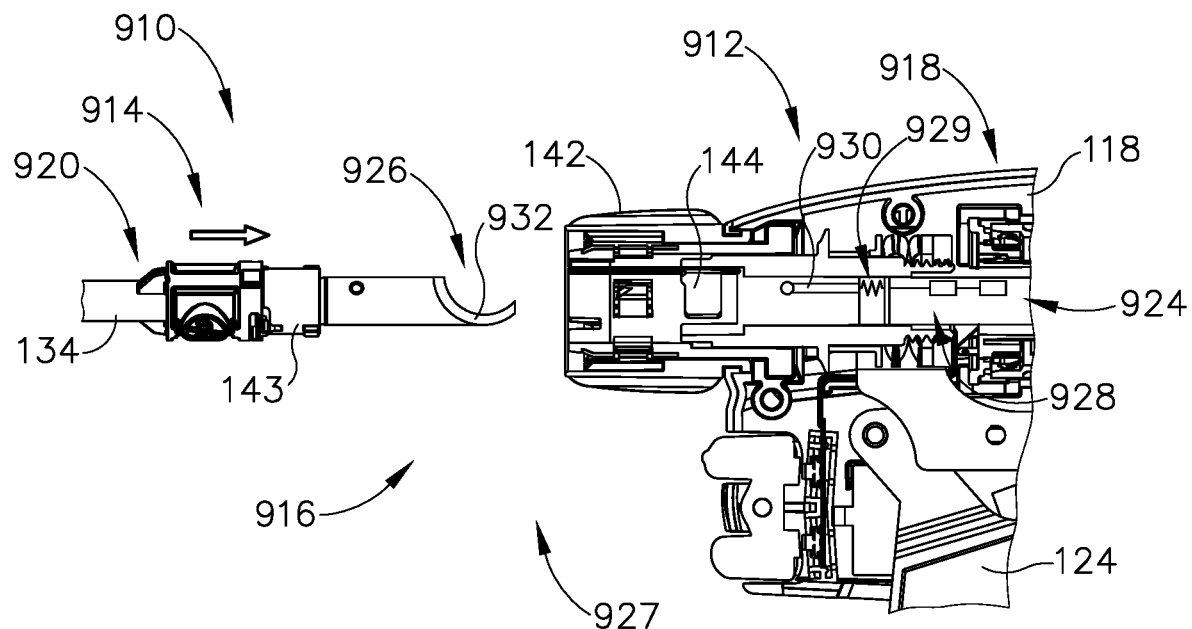
FIG. 27A depicts a schematic, enlarged sectional view of the shaft assembly of FIG. 25 being inserted into the handle assembly of FIG. 26 in the locked-out state.
Figure 27B:
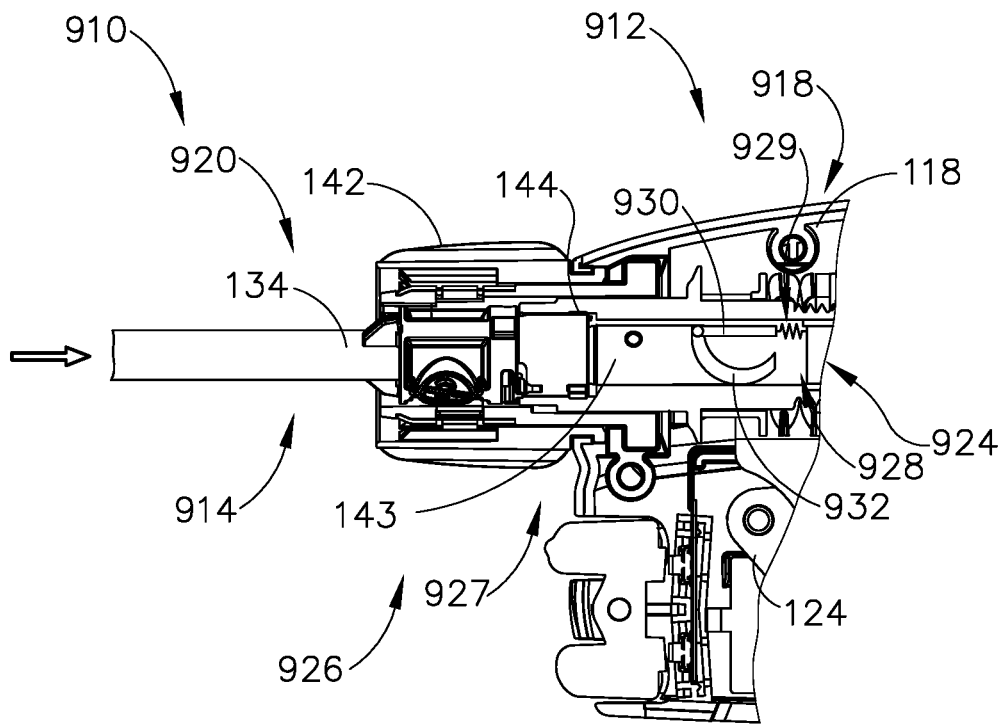
FIG. 27B depicts the schematic, enlarged sectional view of the shaft assembly and the handle assembly similar to FIG. 27A, but showing the electrical connection of the modular electrical coupling in the locked-out state.
Figure 27C:
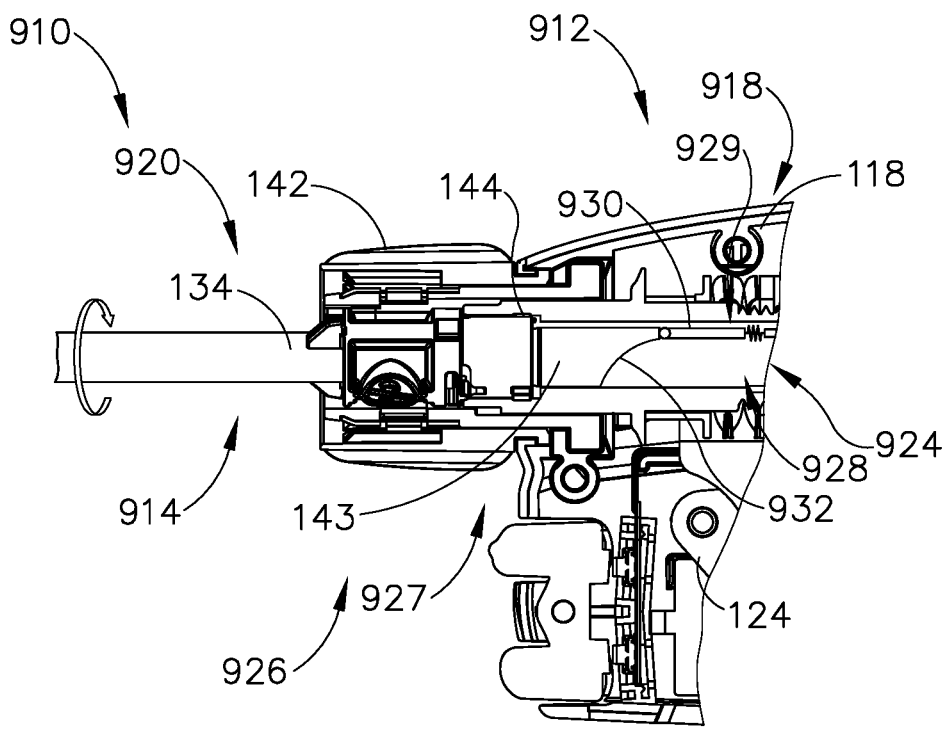
FIG. 27C depicts the schematic, enlarged sectional view of the shaft assembly and the handle assembly similar to FIG. 27B, but showing the electrical connection of the modular electrical coupling in the operational state.

With respect to FIGS. 25-26, first lockout portion (924) includes a first electrical connection (928) with potentiometer (929) operatively connected to a pin (930). Pin (930) is movably mounted within handle assembly (918) and connected to potentiometer (929) from a disconnected position, continuously through a plurality of intermediate positions, and to a connected position as shown in FIGS. 27A-27C. In response to the position of pin (930), potentiometer (929) is configured to generate a disconnected voltage in the disconnected position, one of a variably continuous voltage in the intermediate positions, and a connected voltage in the connected position. Second lockout portion (926) includes a ramp surface (932) that proximally spirals from shaft assembly (920) in the present example. Ramp surface (932) is configured to continuously urge pin (930) from the disconnected position to the connected position upon assembly upon mechanical connection of shaft assembly (920) to handle assembly (918) in the predetermined alignment shown in FIG. 27C. Thereby, electrical lockout (916) transitions surgical instrument (910) from the incomplete and/or misaligned locked-out state to the operational state as discussed above with respect to transducer power circuit (170) of FIGS. 9A-9C. Furthermore, in one example, controller (194) (see FIGS. 9A-9C) detects the disconnected, intermediate, or connected voltage of potentiometer (929) and communicates a disconnected, partially connected, or connected and aligned state to the operator for additional information regarding the operative state of ultrasonic surgical instrument (910) in use.

Figure 28:
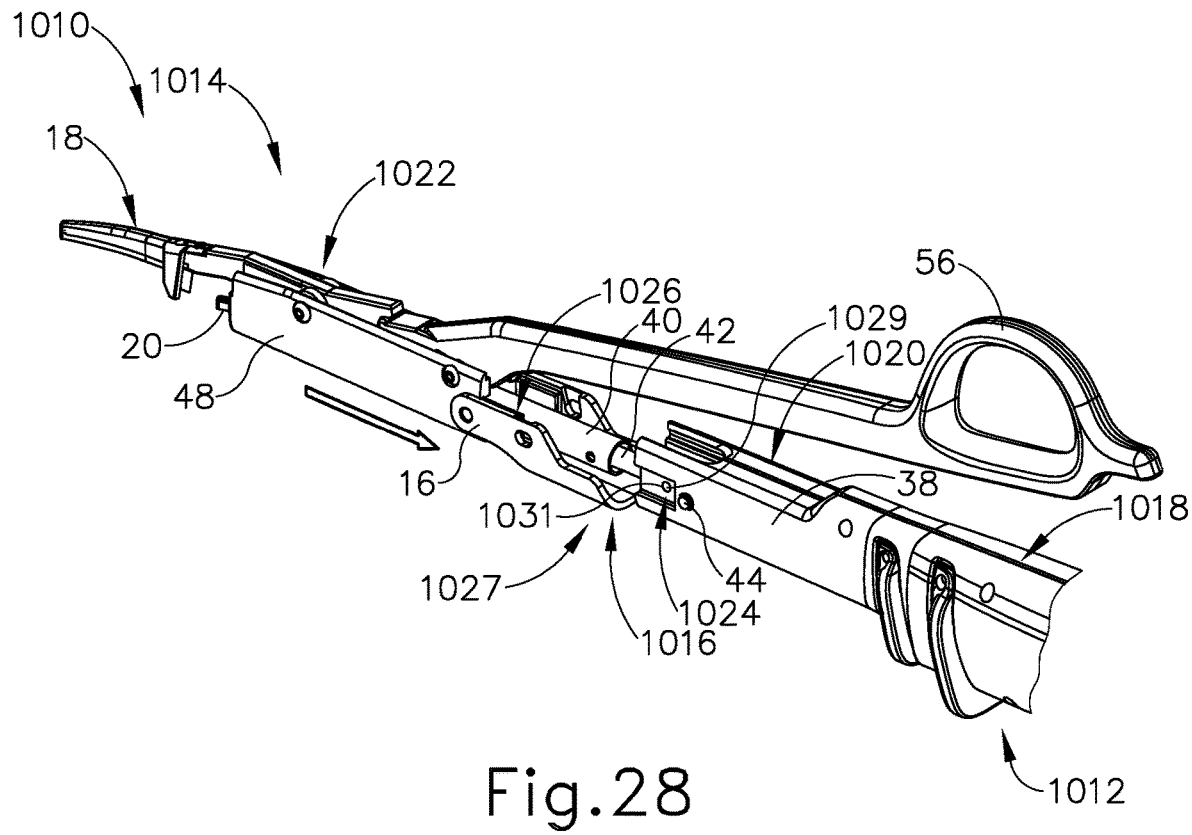
FIG. 28 depicts a schematic, perspective view of an eighth exemplary surgical instrument having an eighth example of an electrical lockout with an eighth modular electrical coupling in a locked-out state.

H. Eighth Exemplary Ultrasonic Surgical Instrument Having an Eighth Example of an Electrical Lockout FIGS. 28-29 show an eighth exemplary ultrasonic surgical instrument (1010) including a first modular assembly (1012), a second modular assembly (1014), and a eighth example of an electrical lockout (1016) for inhibiting misaligned use of surgical instrument (1010) in a locked-out state. In the present example, first modular assembly (1012) has a handle assembly (1018) and a distally extending shaft assembly (1020), whereas second modular assembly (1014) has a clamp arm assembly (1022). Electrical lockout (1016) has a first lockout portion (1024) positioned on a distal portion of handle assembly (1018) and a second lockout portion (1-26) positioned on a proximal portion of clamp arm assembly (422). First and second lockout portions (1024, 1026) collectively define an eighth modular electrical coupling (1027) and cooperatively align as clamp arm assembly (1022) mechanically connects to handle assembly (1018) with a predetermined alignment to direct surgical instrument (1010) from the locked-out state to the operational state.

Figure 29A:
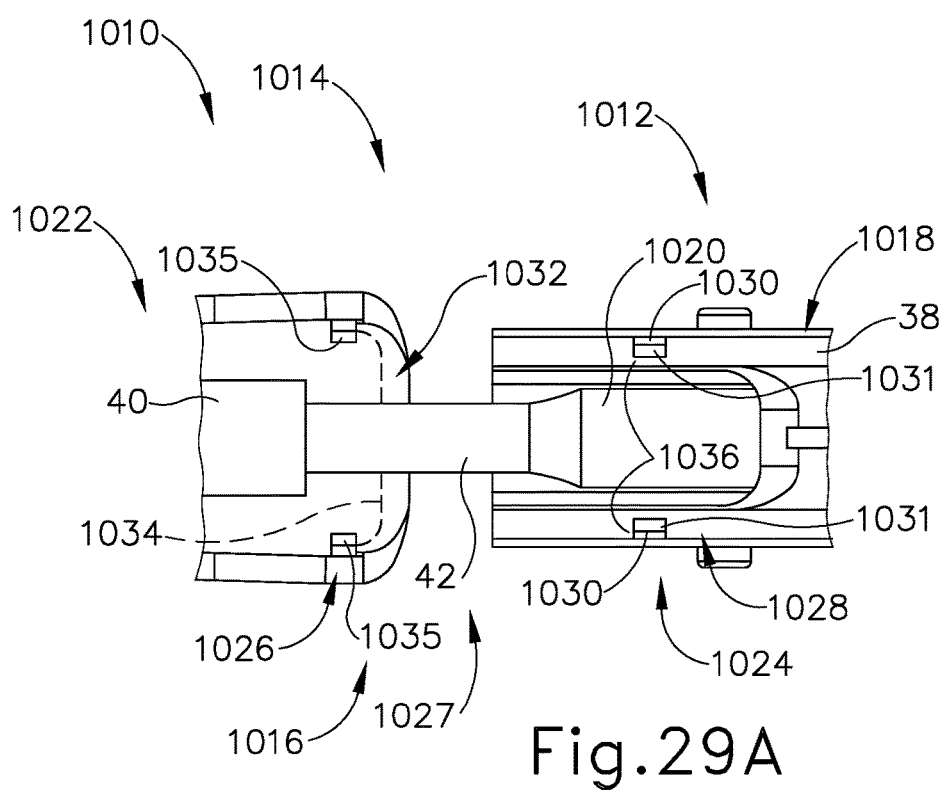
FIG. 29A depicts a schematic, enlarged top sectional view of the surgical instrument of FIG. 28 with the clamp arm assembly being inserted onto a remainder of the surgical instrument in the locked-out state.
Figure 29B:
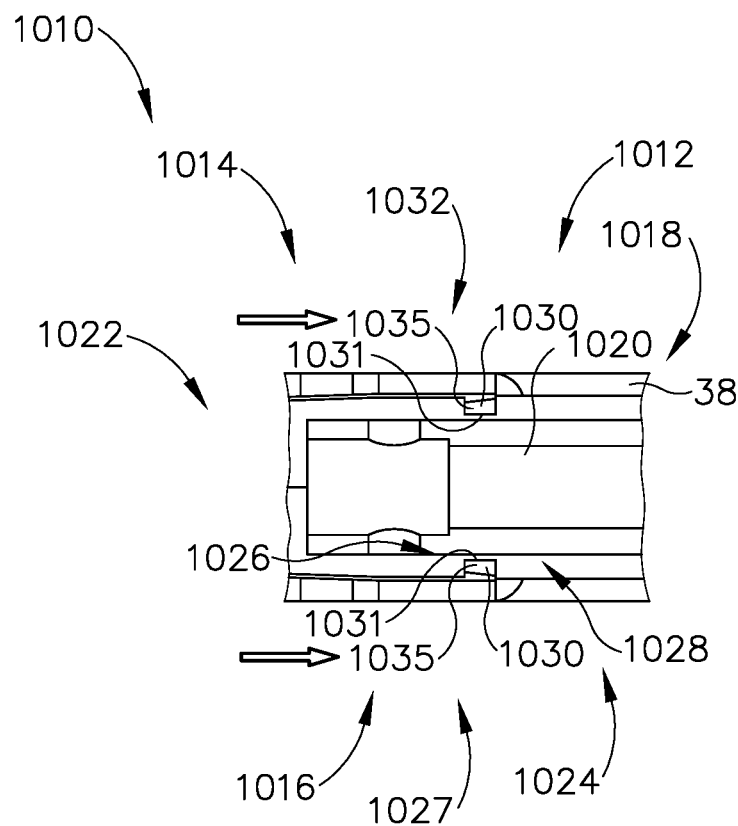
FIG. 29B depicts the schematic, enlarged top sectional view of the surgical instrument similar to FIG. 29A, but showing the modular electrical coupling connected such that the surgical instrument is in the operational state.
Figure 30:
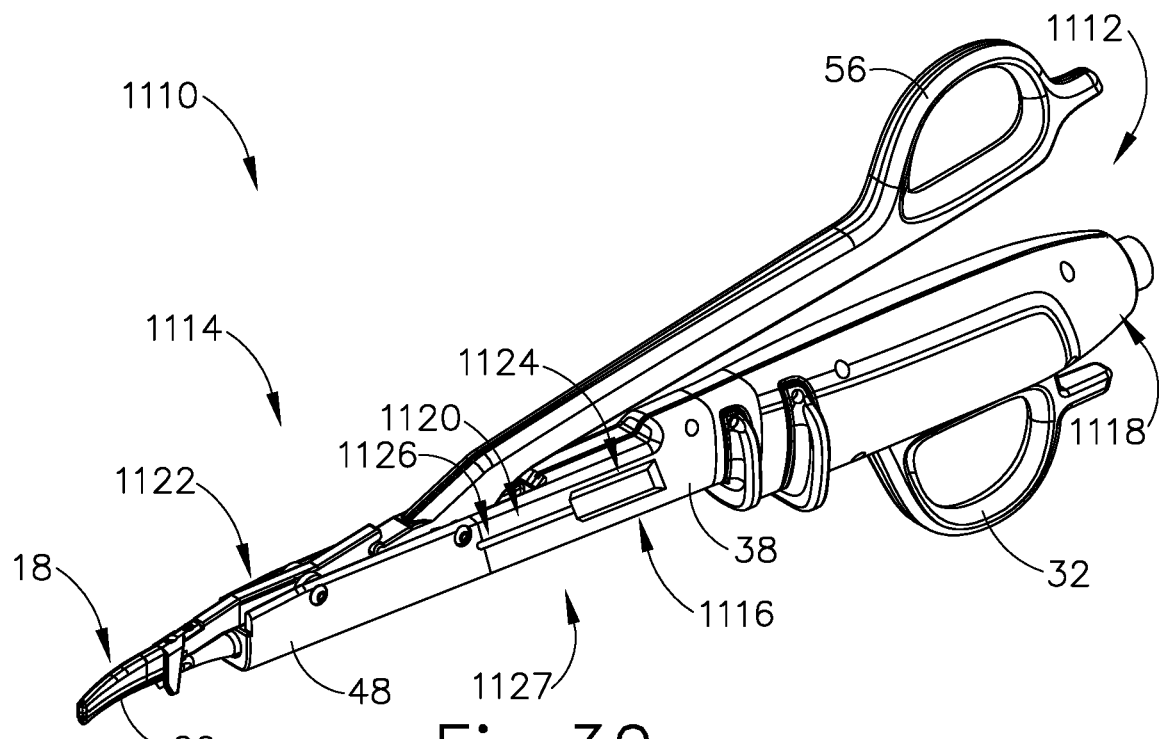
FIG. 30 depicts a schematic, perspective view of a ninth exemplary surgical instrument having a ninth example of an electrical lockout with a ninth modular electrical coupling in an operational state.

With respect to FIGS. 29A-29B, first lockout portion (1024) includes a first electrical connection (1028) with a pair of electrical contacts (1030) and a pair of snap holes (1031). Electrical contacts (1030) are respectively positioned within snap holes (1031), which extend through lateral sides of proximal outer sheath (38). Second lockout portion (1026) includes a second electrical connection (1032) including an electrical shunt (1034) and a pair of snaps (1035), which extend laterally and inwardly from distal outer sheath (48). Electrical shunt (1034) extends between and electrically connects one snap (1035) laterally positioned opposite from the other snap (1035). Electrical shunt (434) is configured to extend between snaps (1035) across an electrical gap (1036). Snaps (1035) of electrical shunt (186) are configured to be received within snap holes (1031) against respective electrical contacts (1030) such that electrical shunt (1034) electrically connects electrical contacts (1030). In addition, snaps (1035) are further configured to mechanically connect shaft assembly (1020) to handle assembly (1018). Electrical shunt (1034) electrically connects electrical contacts (1030) upon mechanical connection of clamp arm assembly (1022) to handle assembly (418) in the predetermined alignment shown in FIG. 29B. Thereby, electrical lockout (1016) transitions surgical instrument (1010) from the incomplete and/or misaligned locked-out state to the operational state as discussed above with respect to transducer power circuit (170) of FIGS. 9A-9C.

I. Ninth Exemplary Ultrasonic Surgical Instrument Having a Ninth Example of an Electrical Lockout FIGS. 30-32B show a ninth exemplary ultrasonic surgical instrument (1110) including a first modular assembly (1112), a second modular assembly (1114), and a ninth example of an electrical lockout (1116) for inhibiting misaligned use of surgical instrument (1110) in a locked-out state. In the present example, first modular assembly (1112) has a handle assembly (1118) and a distally extending shaft assembly (1120), whereas second modular assembly (1114) has a clamp arm assembly (1122). Electrical lockout (1116) has a first lockout portion (1124) positioned on a distal portion of handle assembly (1118) and a second lockout portion (1126) positioned on a proximal portion of clamp arm assembly (1122). First and second lockout portions (1124, 1126) collectively define a ninth modular electrical coupling (1127) and cooperatively align as clamp arm assembly (1122) mechanically connects to handle assembly (1118) with a predetermined alignment to direct surgical instrument (1110) from the locked-out state to the operational state.

Figure 31A:
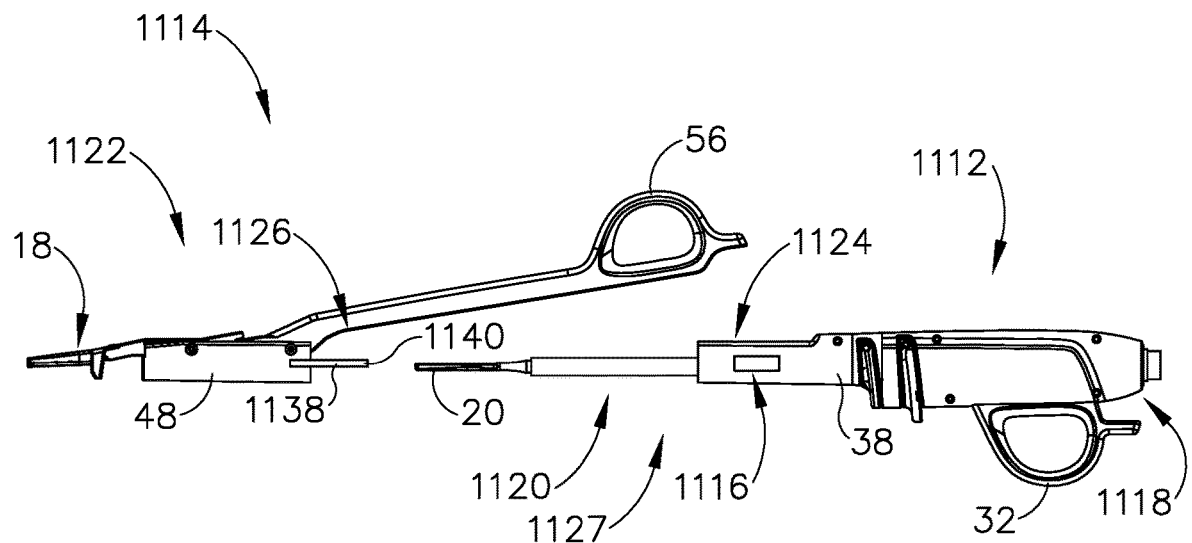
FIG. 31A depicts a schematic, elevational side view of the surgical instrument of FIG. 30 with a clamp arm assembly removed from the remainder of the surgical instrument in a locked-out state.
Figure 31B:
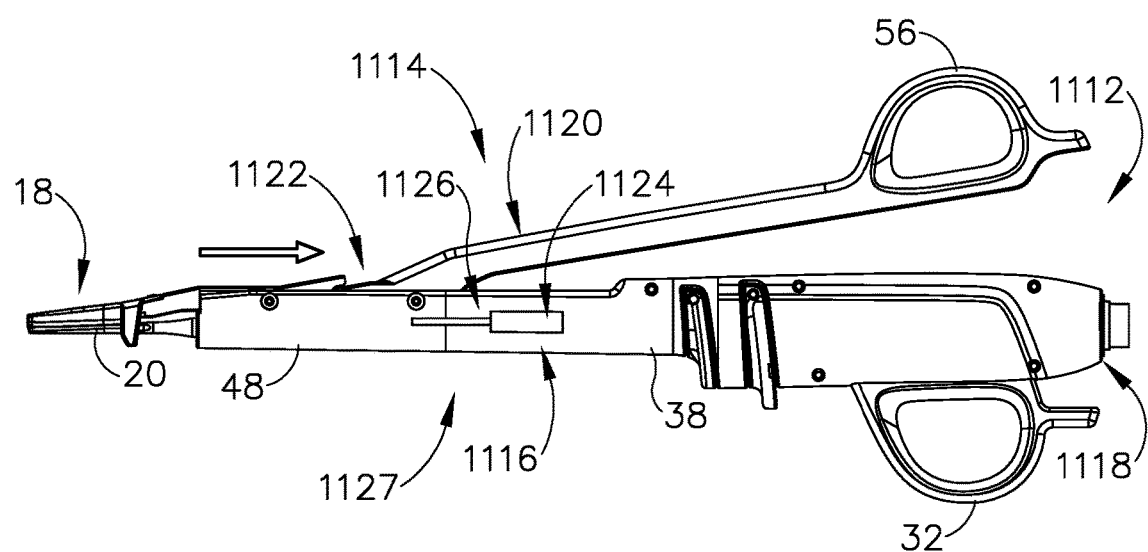
FIG. 31B depicts the schematic, elevational side view of the surgical instrument similar to FIG. 31A, but showing the electrical lockout and the modular electrical coupling in electrical connection such that the surgical instrument is in the operational state.

With respect to FIG. 31A and FIG. 32A, first lockout portion (1124) includes first and second push members (1129), a first electrical connection (1128) with a first pair of electrical contacts (1130) and a second pair of electrical contacts (1130) as well as a second electrical connection (1132) with first and second electrical shunts (1134). Each first and second push member (1129) is resiliently mounted in first and second longitudinal slots (1135), which are blind and extending through laterally opposing sides of proximal outer sheath (38). First pair of electrical contacts (1130) are positioned within first longitudinal slot (1135), whereas first electrical shunt (1134) laterally extends across first push member (1129). Generally, first electrical shunt (1134) and first pair of electrical contacts (1130) do not electrically connect due to misalignment thus defining an electrical gap (1136). However, urging resiliently mounted first push member (1129) proximally to the predetermined alignment electrically connects first pair of electrical contacts (1130) via first electrical shunt (1134).

Second pair of electrical contacts (1130) are positioned within second longitudinal slot (1135), whereas second electrical shunt (1134) laterally extends across second push member (1129). Again, second electrical shunt (1134) and second pair of electrical contacts (1130) do not electrically connect due to misalignment thus defining another electrical gap (1136). However, urging resiliently mounted second push member (1129) proximally to the predetermined alignment electrically connects second pair of electrical contacts (1130) via second electrical shunt (1134).

Second lockout portion (1126) includes first and second legs (1136) respectively extending from distal outer sheath (48) to first and second abutment surfaces (1140). First and second abutment surfaces (1140) are configured to be respectively received in first and second slots (1135) upon mechanical connection of clamp arm assembly (1122) to handle assembly (1118) in the predetermined alignment shown in FIG. 31B and FIG. 32B. In the present example, each first and second pair of electrical contacts (1130) with electrical gaps (1136) is in the same circuit to close for use. Thereby, electrical lockout (1116) transitions surgical instrument (1110) from the incomplete and/or misaligned locked-out state to the operational state as discussed above with respect to transducer power circuit (170) of FIGS. 9A-9C.

Figure 34A:
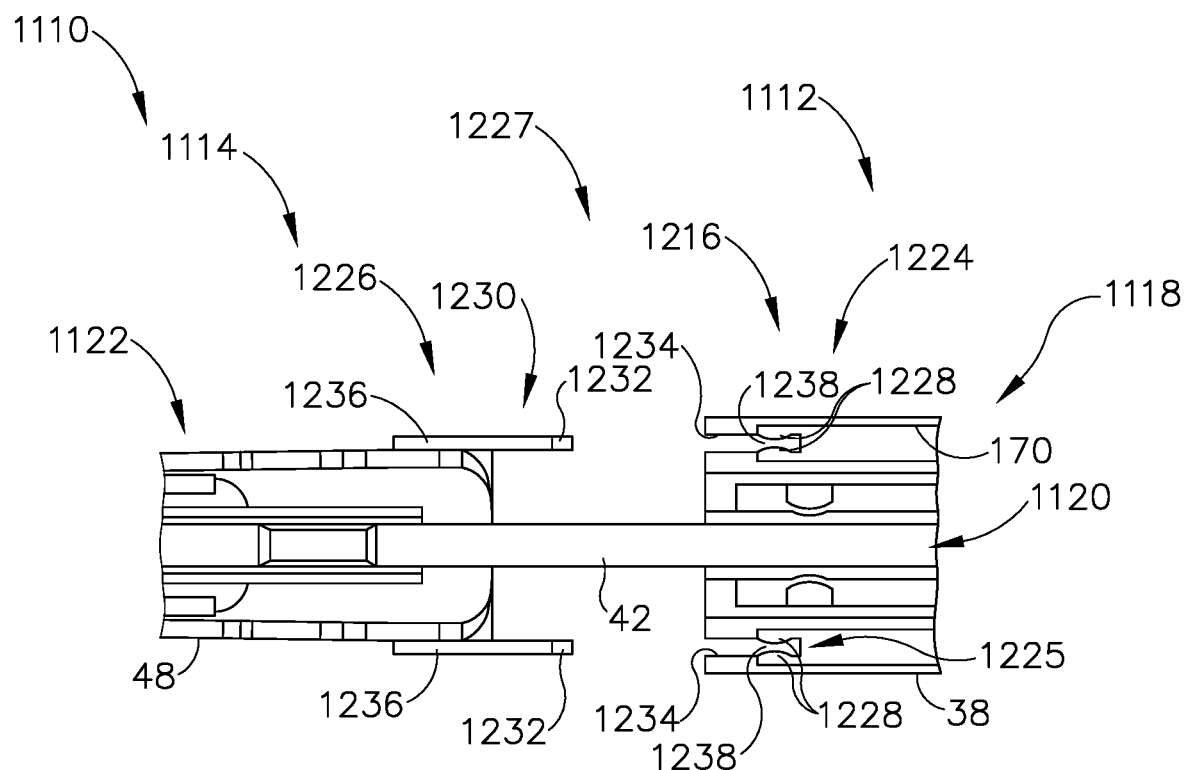
FIG. 34A depicts a schematic, enlarged, top sectional view of the surgical instrument of FIG. 33 with the clamp arm assembly being connected to the remainder of the surgical instrument.
Figure 34B:
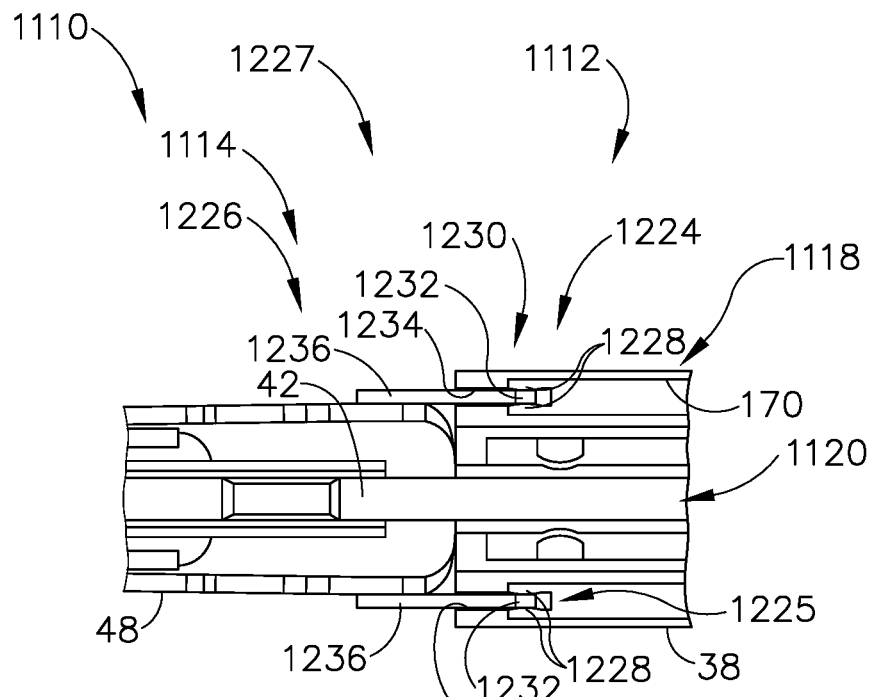
FIG. 34B depicts the schematic, enlarged, top sectional view of the surgical instrument similar to FIG. 34A, but showing the clamp arm assembly connected to shaft assembly and the handle assembly such that the electrical lockout and the modular electrical coupling are in electrical connection and the surgical instrument is in an operational state.

J. Ninth Exemplary Ultrasonic Surgical Instrument Having a Tenth Example of an Electrical Lockout FIGS. 33-34B show ultrasonic surgical instruments (1110) discussed above with first modular assembly (1112) and second modular assembly (1114) in conjunction with a tenth example of an electrical lockout (1216) including a tenth modular electrical coupling (1227). Electrical lockout (1216) has a first lockout portion (1224) positioned on a distal portion of handle assembly (1118) and a second lockout portion (1226) positioned on a proximal portion of clamp arm assembly (1122).

First lockout portion (1224) includes first electrical connection (1225) with first and second pairs of electrical contacts (1228). Second lockout portion (1226) includes second electrical connection (1230) including first and second electrical shunts (1232). More particularly, first lockout portion (1224) further includes first and second longitudinal slots (1234), which are blind and extending through laterally opposing sides of proximal outer sheath (38). Second lockout portion (1226) further includes first and second legs (1236) proximally extending from distal outer sheath (48) and configured to be respectively received within first and second slots (1234) in the predetermined alignment. First and second pairs of electrical contacts (1228) are respectively positioned within first and second slot (1234), and first and second shunts are positioned on proximal portions of respective first and second legs (1236).

First electrical shunt (1232) is configured to be received in a first electrical gap (1238) between first pair of electrical contacts (1228), and second electrical shunt (1232) is configured to be received in second electrical gap (1238) between second pair of electrical contacts (1228). In the present example shown in FIGS. 34A-34B, each first and second pair of electrical contacts (1228) include leaf springs with electrical gaps (1238) in the same circuit to close for use. First and second electrical shunts (1232) electrically connect first and second pair of electrical contacts (1228) respectively upon mechanical connection of clamp arm assembly (1122) to handle assembly (1118) in predetermined alignment. Thereby, electrical lockout (1216) transitions surgical instrument (1110) from the incomplete and/or misaligned locked-out state to the operational state as discussed above with respect to transducer power circuit (170) of FIGS. 9A-9C.

Figure 35:
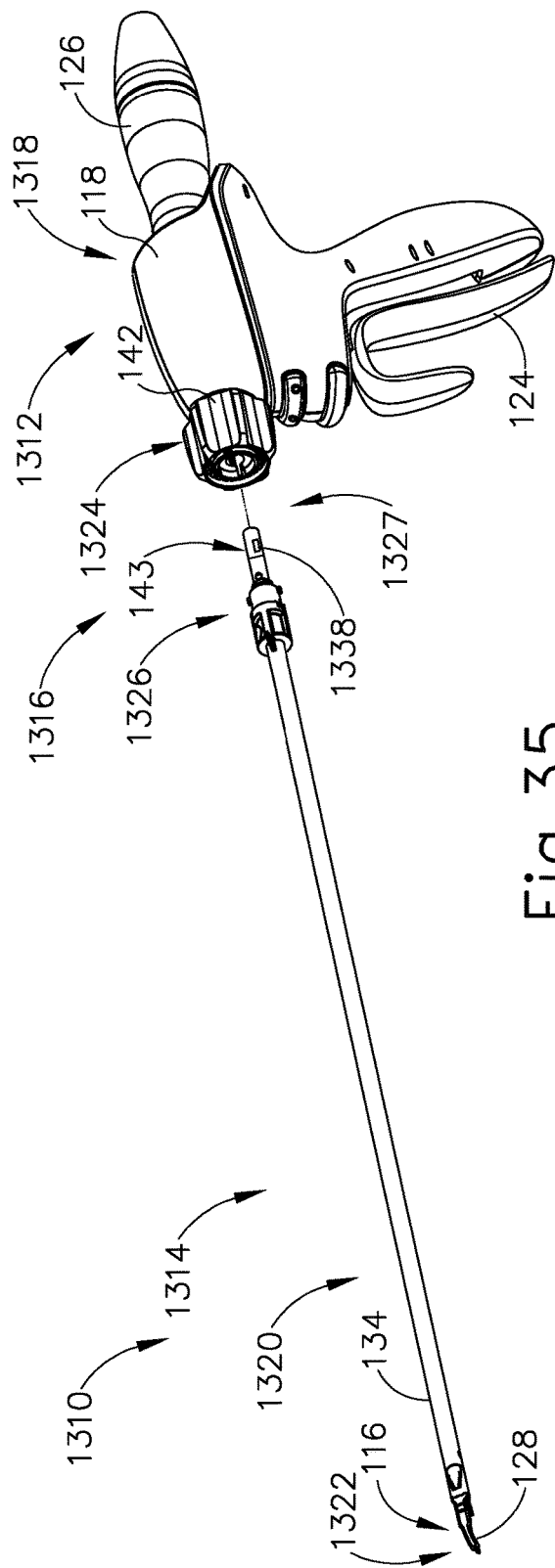
FIG. 35 depicts a perspective view of a tenth exemplary surgical instrument having an eleventh example of an electrical lockout with an eleventh modular electrical coupling and a shaft assembly removed from a handle assembly such that the surgical instrument is in a locked-out state.

K. Tenth Exemplary Ultrasonic Surgical Instrument Having an Eleventh Example of an Electrical Lockout FIGS. 35-36C show a tenth exemplary ultrasonic surgical instrument (1310) including a first modular assembly (1312), a second modular assembly (1314), and an eleventh example of an electrical lockout (1316) for inhibiting misaligned use of surgical instrument (1310) in a locked-out state. In the present example, first modular assembly (1312) has a handle assembly (1318), whereas second modular assembly (1314) has a shaft assembly (1320) and a distally extending clamp arm assembly (1322). Electrical lockout (1316) has a first lockout portion (1324) positioned on a distal portion of handle assembly (1318) and a second lockout portion (1326) positioned on a proximal portion of shaft assembly (1320). First and second lockout portions (1324, 1326) collectively define an eleventh modular electrical coupling (1327) and cooperatively align as shaft assembly (1320) mechanically connects to handle assembly (1318) with a predetermined alignment to direct surgical instrument (1310) from the locked-out state to the operational state.

Figure 36A:
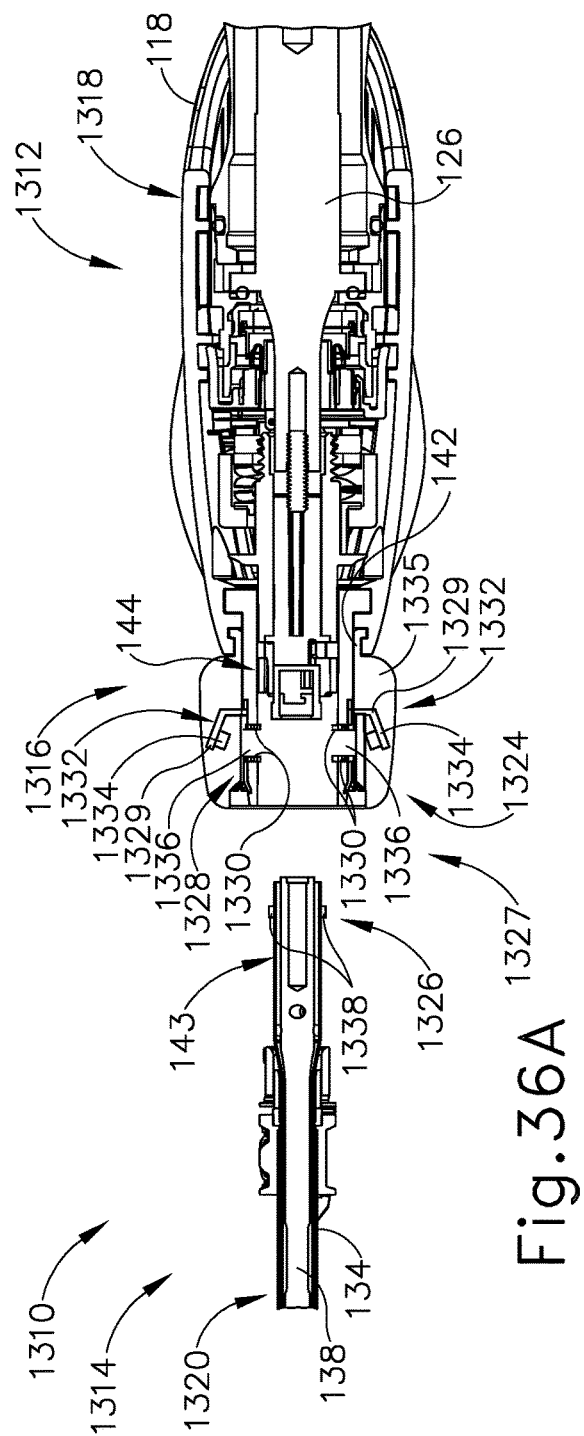
FIG. 36A depicts a schematic, enlarged, top sectional view of the surgical instrument of FIG. 35.
Figure 36B:
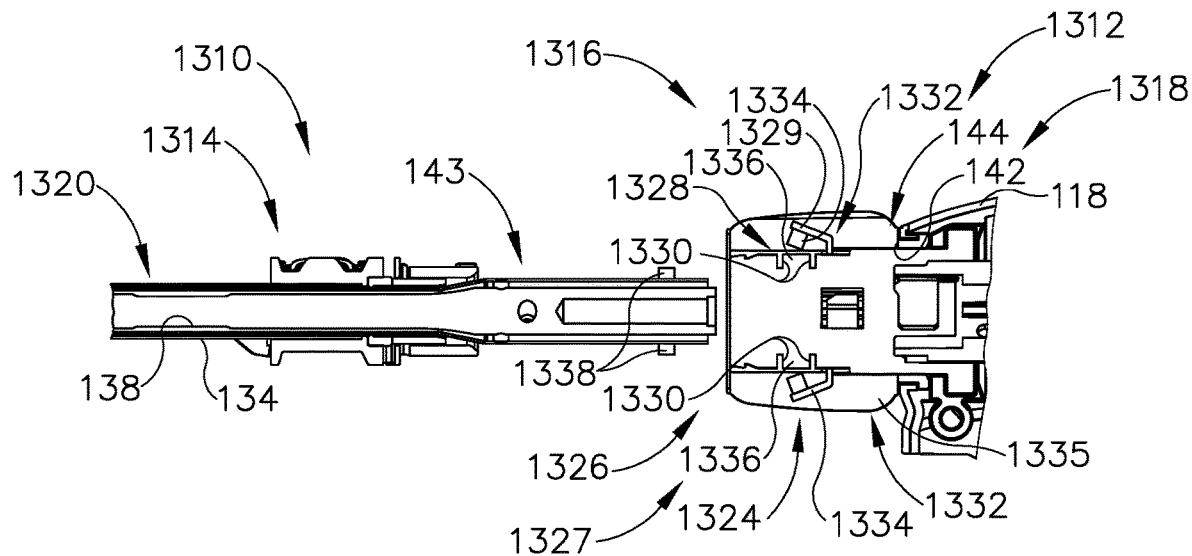
FIG. 36B depicts the schematic, enlarged, top sectional view of the surgical instrument similar to FIG. 36A, but showing the shaft assembly being connected to the handle assembly such that the surgical instrument is in the locked-out state.
Figure 36C:
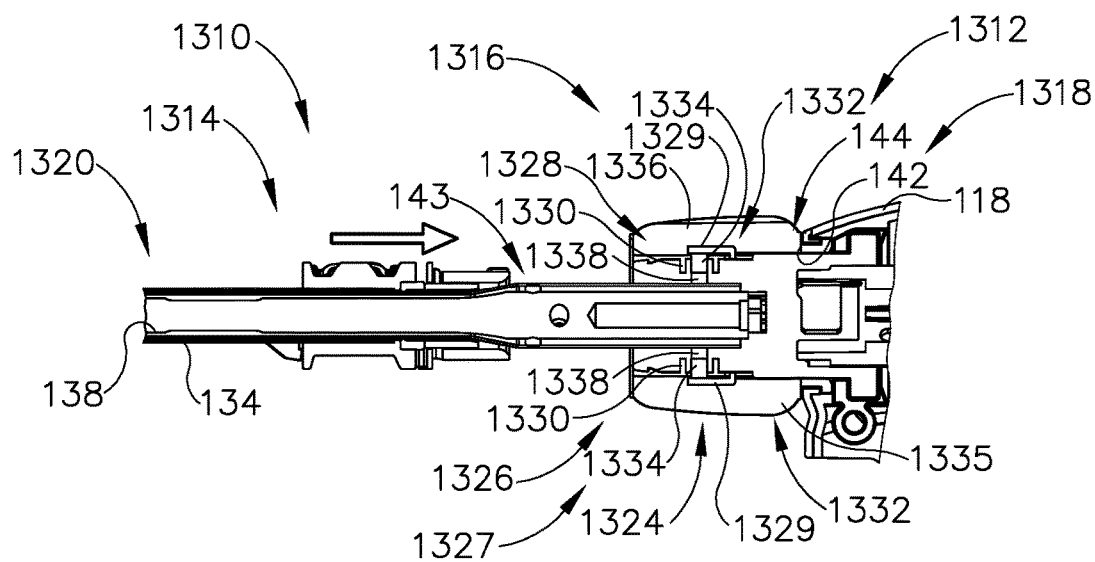
FIG. 36C depicts the schematic, enlarged, top sectional view of the surgical instrument similar to FIG. 36B, but showing the shaft assembly connected to the handle assembly such that the electrical lockout and the modular electrical coupling are in electrical connection and the surgical instrument is in an operational state.

With respect to FIGS. 36A-36C, first lockout portion (1324) includes first and second pivot members (1329), a first electrical connection (1328) with a first pair of electrical contacts (1330) and a second pair of electrical contacts (1330) as well as a second electrical connection (1332) with first and second electrical shunts (1334). Each first and second pivot member (1329) is resiliently mounted within a hollow (1335) of knob (142). First pair of electrical contacts (1330) are positioned in hollow (1335) on one side of knob (142), whereas first electrical shunt (1334) laterally extends across first pivot member (1329). Generally, first electrical shunt (1334) and first pair of electrical contacts (1330) do not electrically connect due to misalignment thus defining an electrical gap (1336). However, urging resiliently mounted first pivot member (1329) inwardly to the predetermined alignment electrically connects first pair of electrical contacts (1330) via first electrical shunt (1334).

Second pair of electrical contacts (1330) are positioned in hollow (1335) on another side of knob (142), whereas second electrical shunt (1334) laterally extends across second pivot member (1329). Again, second electrical shunt (1334) and second pair of electrical contacts (1330) do not electrically connect due to misalignment thus defining another electrical gap (1336). However, urging resiliently mounted second pivot member (1329) inwardly to the predetermined alignment electrically connects second pair of electrical contacts (1330) via second electrical shunt (1334).

Second lockout portion (1326) includes first and second magnets (1338) angularly positioned about shaft coupler (143). First and second magnets (1338) are configured to attract first and second pivot members (1329) upon mechanical connection of clamp arm assembly (1122) to handle assembly (1118) in the predetermined alignment shown in FIG. 36C. Electrical shunts (1334) on pivot members (1329) are thus pulled into connection with pairs of electrical contacts (1330) in the predetermined alignment. In the present example, each first and second pair of electrical contacts (1330) with electrical gaps (1336) is in the same circuit to close for use. Thereby, electrical lockout (1316) transitions surgical instrument (1310) from the incomplete and/or misaligned locked-out state to the operational state as discussed above with respect to transducer power circuit (170) of FIGS. 9A-9C. While magnets (1338) are positioned on shaft coupler (143) and pivot members (1329) are attracted to magnets (1338), such as by being metallic, it will be appreciated that either magnets (1338) and/or pivot members (1329) may be magnetic or metallic for attracting the other.

Figure 37:
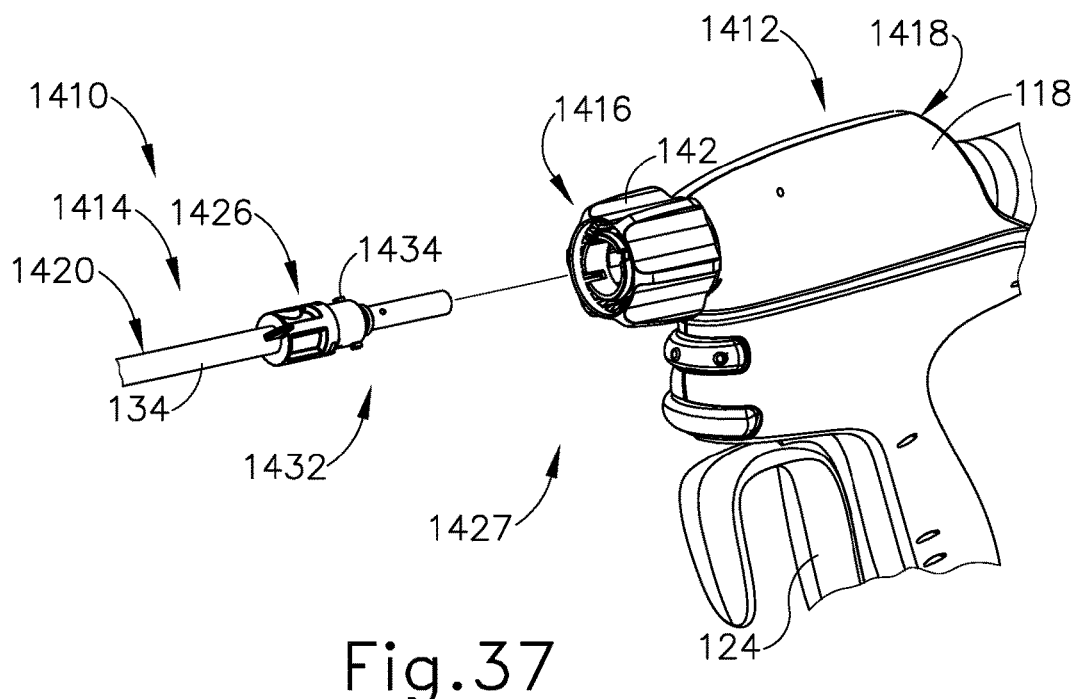
FIG. 37 depicts a schematic, enlarged, perspective view of an eleventh exemplary surgical instrument having a twelfth example of an electrical lockout with a twelfth modular electrical coupling and a shaft assembly removed from a handle assembly such that the surgical instrument is in a locked-out state.

L. Eleventh Exemplary Ultrasonic Surgical Instrument Having a Twelfth Example of an Electrical Lockout FIGS. 37-38C show an eleventh exemplary ultrasonic surgical instrument (1410) including a first modular assembly (1412), a second modular assembly (1414), and a twelfth example of an electrical lockout (1416) for inhibiting misaligned use of surgical instrument (1410) in a locked-out state. In the present example, first modular assembly (1412) has a handle assembly (1418), whereas second modular assembly (1414) has a shaft assembly (1420) and a distally extending clamp arm assembly (not shown). Electrical lockout (1416) has a first lockout portion (1424) positioned on a distal portion of handle assembly (1418) and a second lockout portion (1426) positioned on a proximal portion of shaft assembly (1420). First and second lockout portions (1424, 9146) collectively define a twelfth modular electrical coupling (1427) and cooperatively align as shaft assembly (1420) mechanically connects to handle assembly (1418) with a predetermined alignment to direct surgical instrument (1410) from the locked-out state to the operational state.

Figure 38A:
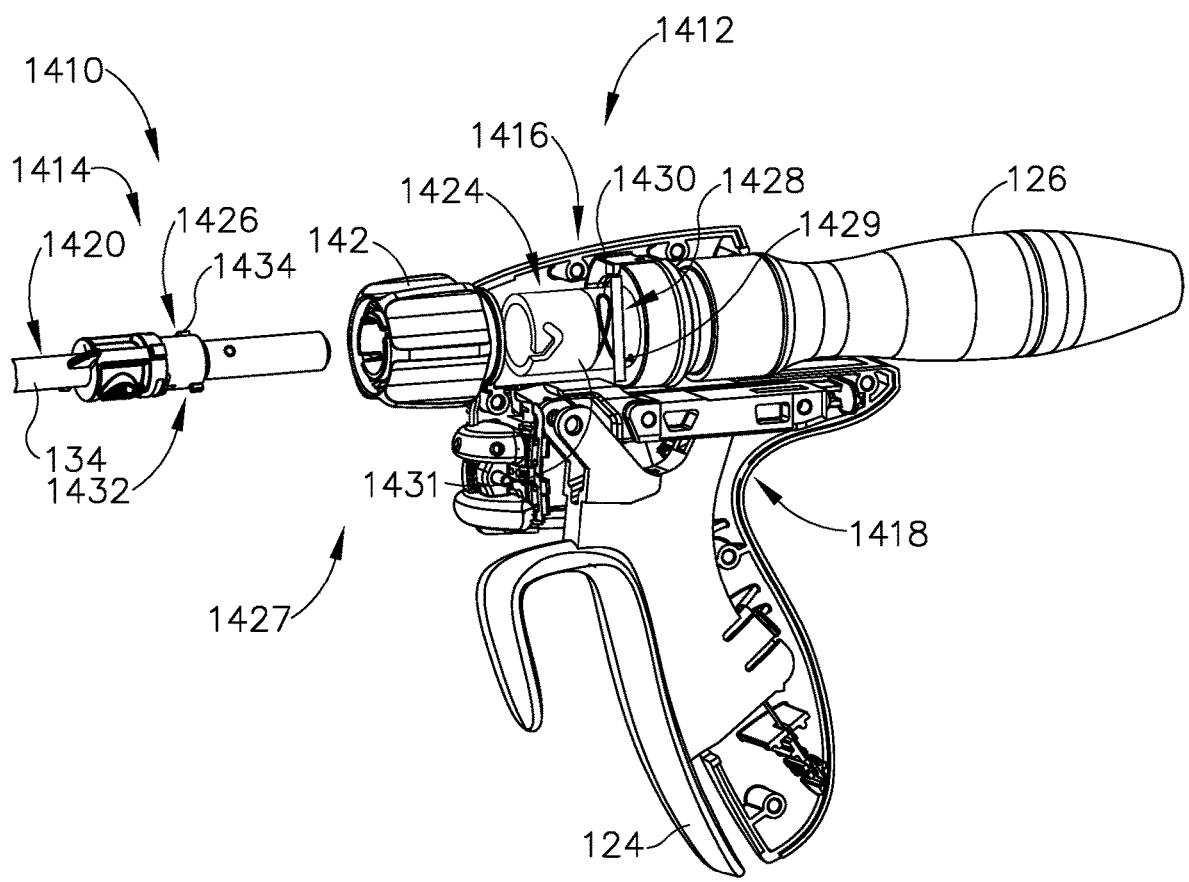
FIG. 38A depicts a schematic, enlarged perspective view of the surgical instrument of FIG. 37 having a portion of a handle assembly removed for greater clarity of the electrical lockout and the modular electrical coupling.
Figure 38B:
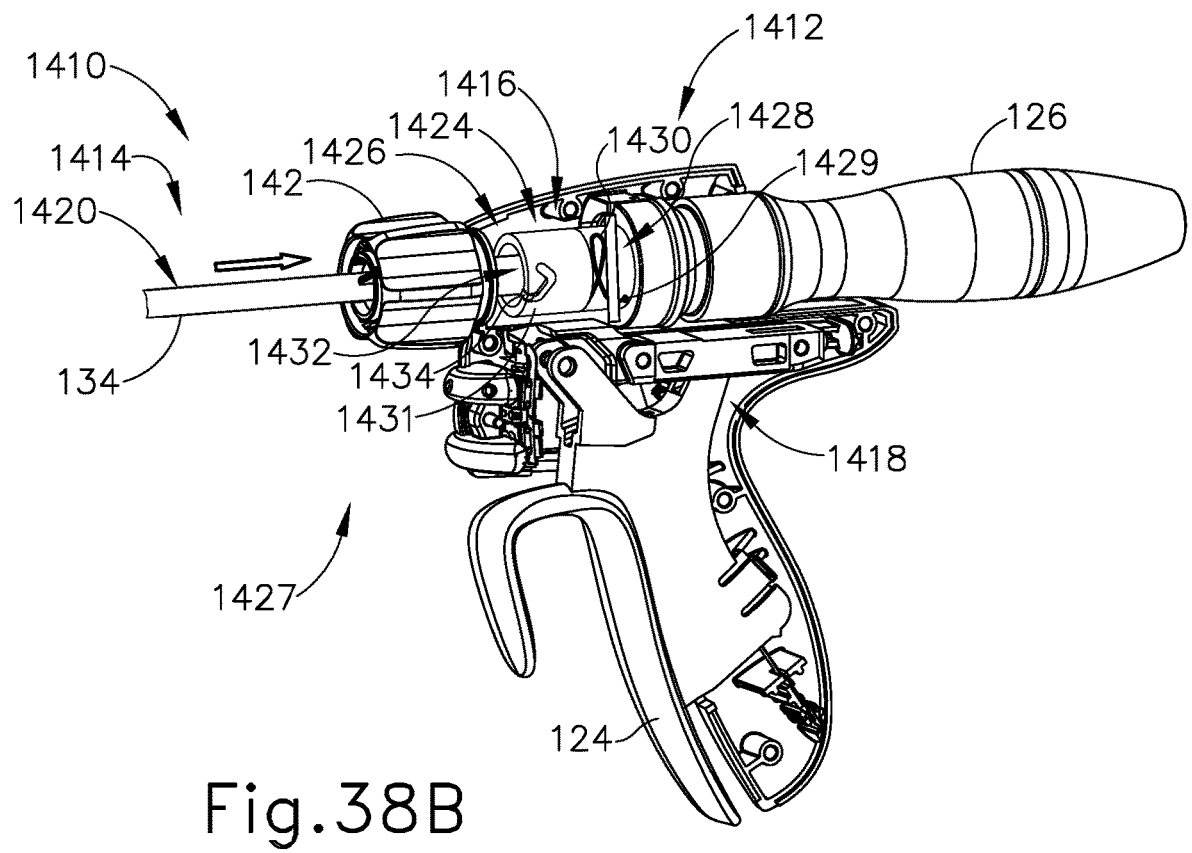
FIG. 38B depicts the schematic, enlarged perspective view of the surgical instrument similar to FIG. 38A, but showing the shaft assembly being connected to the handle assembly such that the surgical instrument is in the locked-out state.
Figure 38C:
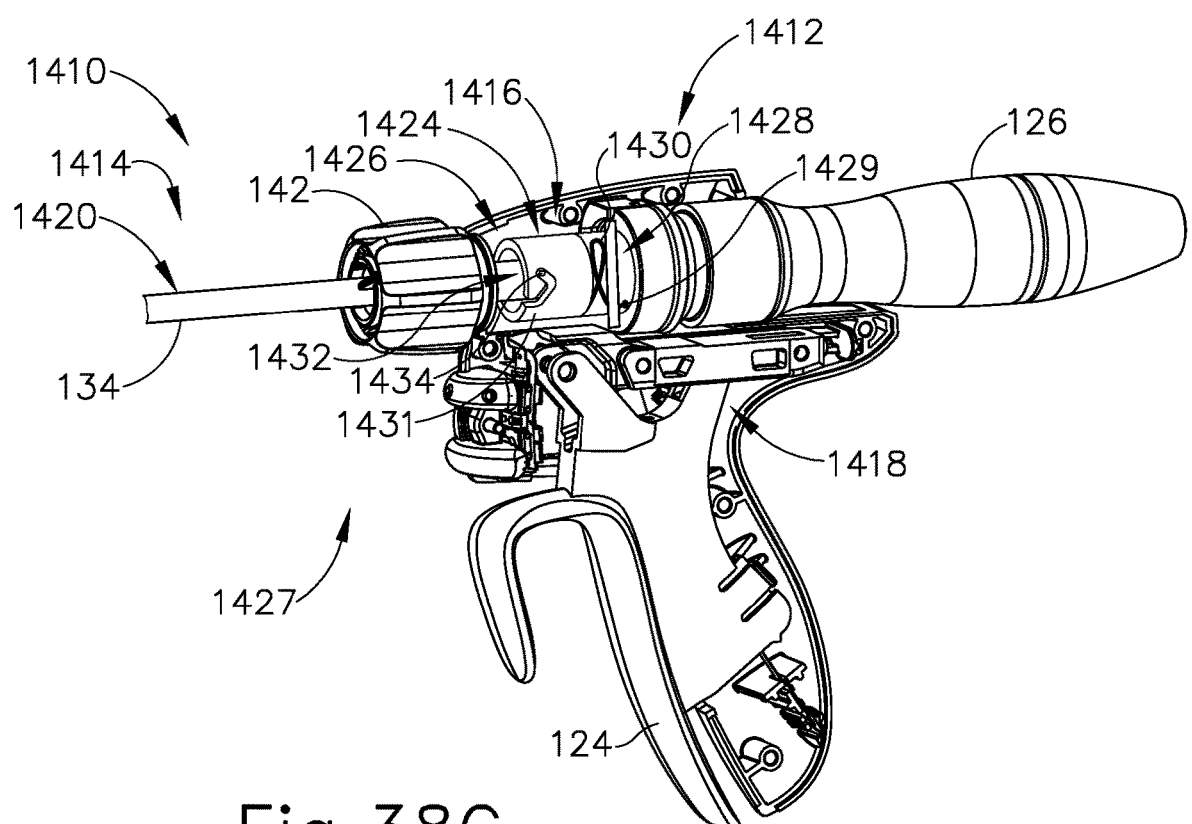
FIG. 38C depicts the schematic, enlarged perspective view of the surgical instrument similar to FIG. 38B, but showing the shaft assembly connected to the handle assembly such that the electrical lockout and the modular electrical coupling are in electrical connection and the surgical instrument is in an operational state.

With respect to FIGS. 38A-38C, first lockout portion (1424) includes a first electrical connection (1428) with a force sensor (1429) operatively connected to a biasing element (1430) supporting a female bayonet body coupler (1431). Female bayonet body coupler (1431) is movably mounted within handle assembly (1418) and connected to force sensor (1429) such that biasing element (1430) is positioned therebetween. In response to the force of biasing element (1430) against force sensor (1429), force sensor (1429) is configured to generate a disconnected resistance in the disconnected position, one of a variably continuous resistance in the intermediate positions, and a connected resistance in the connected position. Second lockout portion (1426) includes a male bayonet shaft coupler (1432) with a proximal abutment surface (1434) in the present example. Proximal abutment surface (1434) is configured to continuously urge female bayonet body coupler (1431) from the disconnected position to the connected position and, in turn, increase applied force on force sensor (1429). Force sensor (1429) thus changes resistance from the disconnected resistance to the connected resistance upon assembly upon mechanical connection of shaft assembly (1420) to handle assembly (1418) in the predetermined alignment shown in FIG. 38C. Thereby, electrical lockout (1416) transitions surgical instrument (1410) from the incomplete and/or misaligned locked-out state to the operational state as discussed above with respect to transducer power circuit (170) of FIGS. 9A-9C. Furthermore, in one example, controller (194) (see FIGS. 9A-9C) detects the disconnected, intermediate, or connected resistance of force sensor (1429) and communicates a disconnected, partially connected, or connected and aligned state to the operator for additional information regarding the operative state of ultrasonic surgical instrument (1410) in use.

Figure 39:
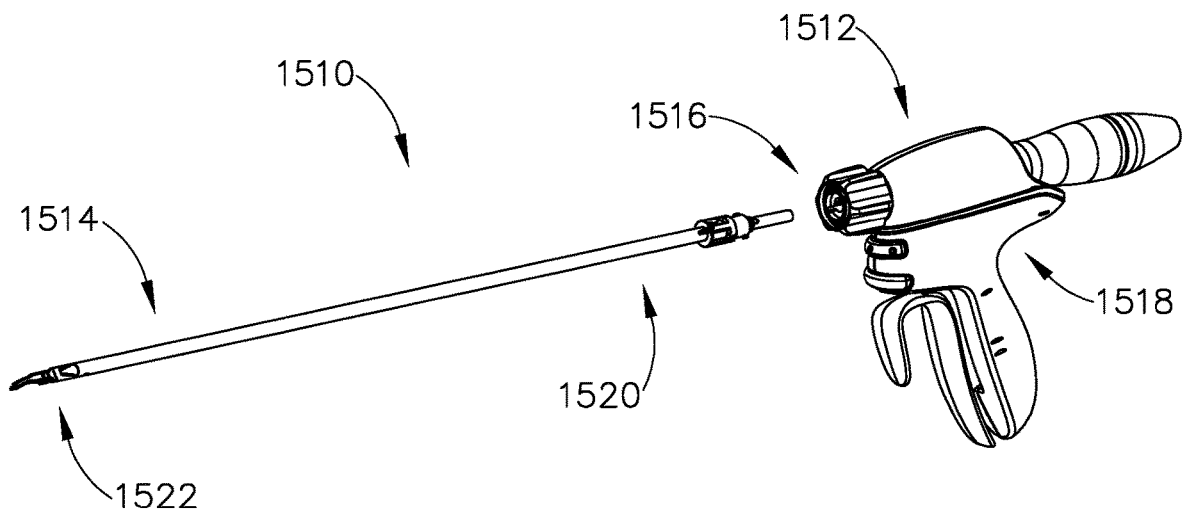
FIG. 39 depicts a schematic, perspective view of a twelfth exemplary surgical instrument having a thirteenth example of an electrical lockout with a thirteenth modular electrical coupling and a shaft assembly removed from a handle assembly such that the surgical instrument is in a locked-out state.

M. Twelfth Exemplary Ultrasonic Surgical Instrument Having a Thirteenth Example of an Electrical Lockout FIGS. 39-40B show a twelfth exemplary ultrasonic surgical instrument (1510) including a first modular assembly (1512), a second modular assembly (1514), and a thirteenth example of an electrical lockout (1516) for inhibiting misaligned use of surgical instrument (1510) in a locked-out state. In the present example, first modular assembly (1512) has a handle assembly (1518), whereas second modular assembly (1514) has a shaft assembly (1520) and a distally extending clamp arm assembly (1522). Electrical lockout (1516) has a first lockout portion (1524) positioned on a distal portion of handle assembly (1518) and a second lockout portion (1526) positioned on a proximal portion of shaft assembly (1520). First and second lockout portions (1524, 1526) collectively define a thirteenth modular electrical coupling (1527) and cooperatively align as shaft assembly (1520) mechanically connects to handle assembly (1518) with a predetermined alignment to direct surgical instrument (1510) from the locked-out state to the operational state.

Figure 40A:
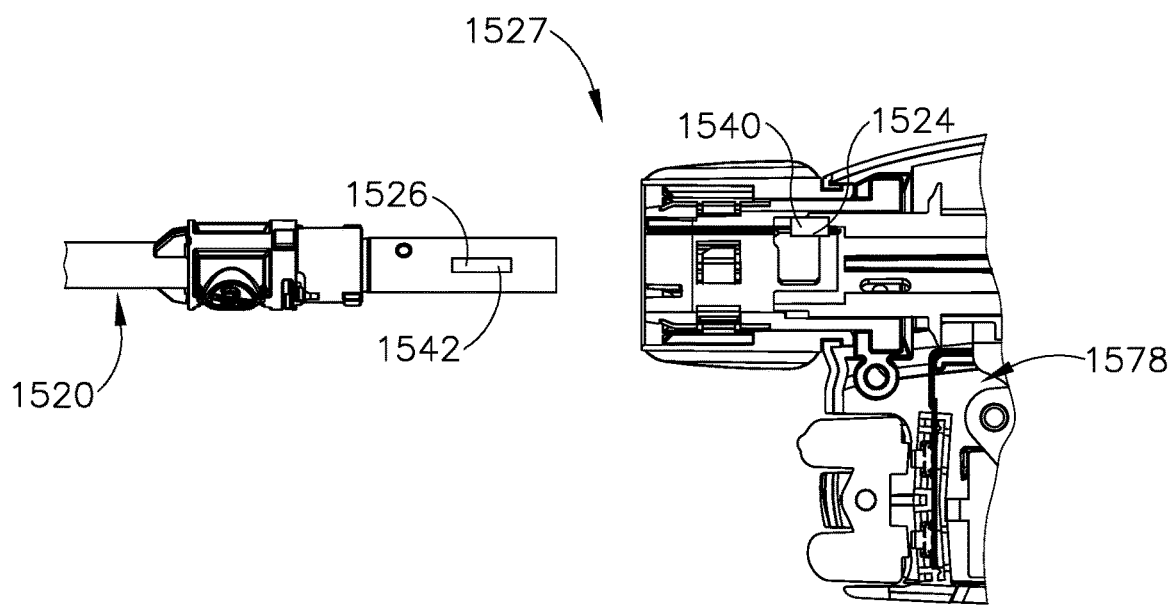
FIG. 40A depicts a schematic, enlarged sectional side view of the shaft assembly of FIG. 39 being inserted into the handle assembly in the locked-out state.
Figure 40B:
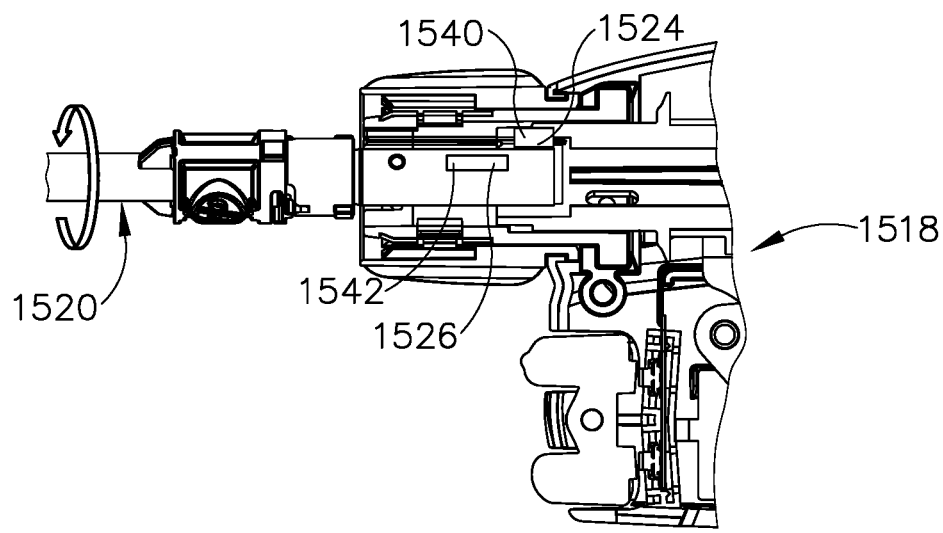
FIG. 40B depicts the schematic, enlarged sectional side view of the shaft assembly and the handle assembly similar to FIG. 40A, but showing the shaft assembly mechanically and electrically connected to the handle assembly such that the surgical instrument is in an operational state.

With respect to FIG. 40A, first lockout portion (1524) includes a position sensor (1540) electronically connected with controller (194). Second lockout portion (1526) includes a trigger element (1542). More particularly, position sensor (1540) is configured to provide information to controller (194) regarding the position of shaft assembly (1520) relative to handle assembly (1518). In some versions of electrical lockout (1516), position sensor (1540) is an optical sensor directed toward shaft assembly (1520) when shaft assembly (1520) is disposed within handle assembly (1518). In these versions of electrical lockout (1516), trigger element (1542) may be an optically identifiable element such as a differently colored, reflective, or otherwise distinct portion of shaft assembly (1520). As shown in FIG. 40B, the identifiable characteristic of trigger element (1542) allows position sensor (1540) to identify when trigger element (1542) is at a desired set location, which indicates both the presence of shaft assembly (1520) within handle assembly (1518) and proper alignment. In other versions of electrical lockout (1516), position sensor (1540) includes a switch and trigger element (1542) includes a fin for depressing the switch when shaft assembly (1520) is disposed and properly aligned within handle assembly (1518). In other versions of electrical lockout (1516), position sensor (1540) includes any sensor style mechanism for coordinating with trigger element (1542) to determine when shaft assembly (1520) is disposed and properly aligned within handle assembly (1518).

Figure 9C:
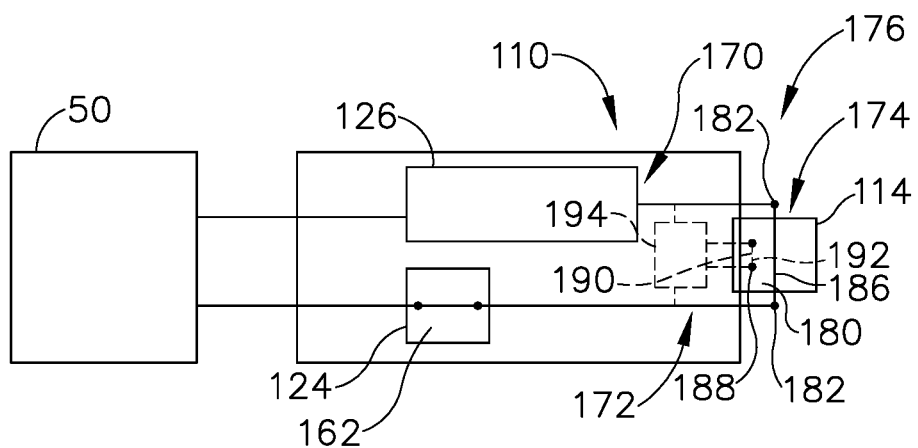
FIG. 9C depicts the diagrammatic view of the transducer power circuit similar to FIG. 9A, but in a selectively closed position and the modular circuit portion aligned such that the modular circuit portion electrically connects to the remainder of the transducer power circuit to allow electrical flow in an operational state.

Once position sensor (1540) indicates to controller (194) that shaft assembly (1520) is disposed and properly aligned within handle assembly (1518), electrical lockout (1516) transitions surgical instrument (1510) from the incomplete and/or misaligned locked-out state to the operational state as discussed above with respect to transducer power circuit (170) of FIGS. 9A-9C.

Figure 41:
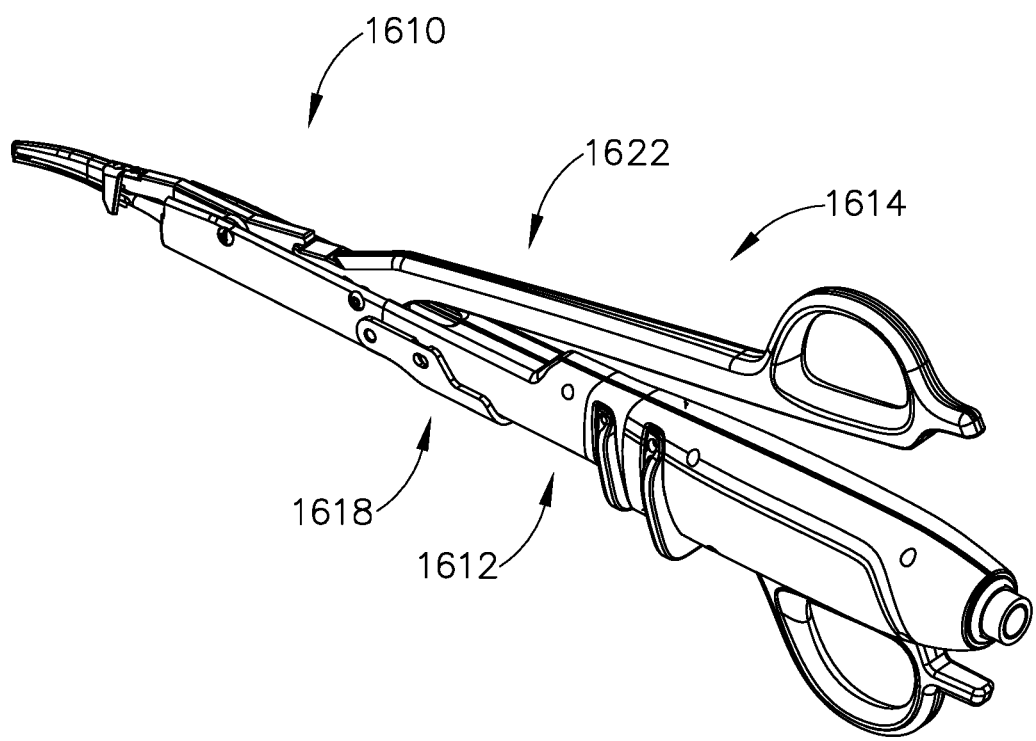
FIG. 41 depicts a schematic, perspective view of a thirteenth exemplary surgical instrument having a fourteenth example of an electrical lockout with a fourteenth modular electrical coupling with a clamp arm assembly mechanically and electrically connected to a remainder of the surgical instrument in an operational state.

N. Thirteenth Exemplary Ultrasonic Surgical Instrument Having a Fourteenth Example of an Electrical Lockout FIGS. 41-42B show a thirteenth exemplary ultrasonic surgical instrument (1610) including a first modular assembly (1612), a second modular assembly (1614), and a fourteenth example of an electrical lockout (1616) for inhibiting misaligned use of surgical instrument (1610) in a locked-out state. In the present example, first modular assembly (1612) has a handle assembly (1618) and a distally extending shaft assembly (1620), whereas second modular assembly (1614) has a clamp arm assembly (1622). Electrical lockout (1616) has a first lockout portion (1624) positioned on a distal portion of handle assembly (1618) and a second lockout portion (1626) positioned on a proximal portion of clamp arm assembly (1622). First and second lockout portions (1624, 1626) collectively define a fourteenth modular electrical coupling (1627) and cooperatively align as clamp arm assembly (1622) mechanically connects to handle assembly (1618) with a predetermined alignment to direct surgical instrument (1610) from the locked-out state to the operational state.

Figure 42A:
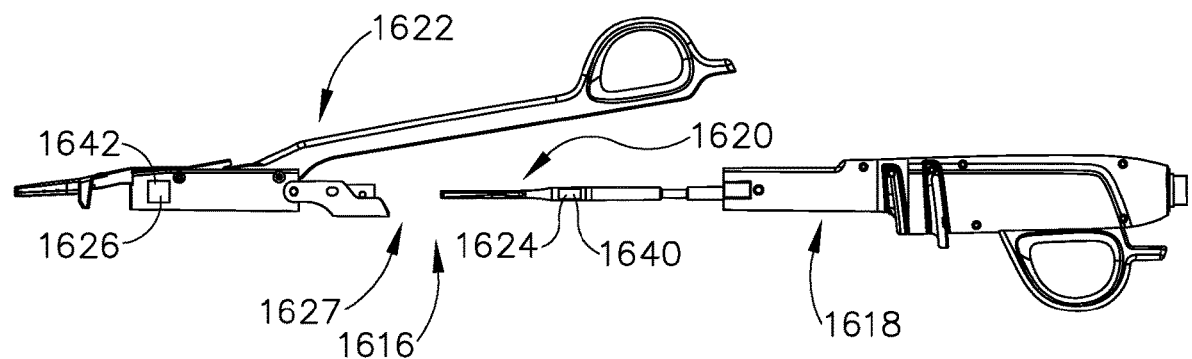
FIG. 42A depicts a schematic, enlarged sectional side view of the shaft assembly being inserted into the remainder of the surgical instrument of FIG. 41 in a locked-out state.
Figure 42B:
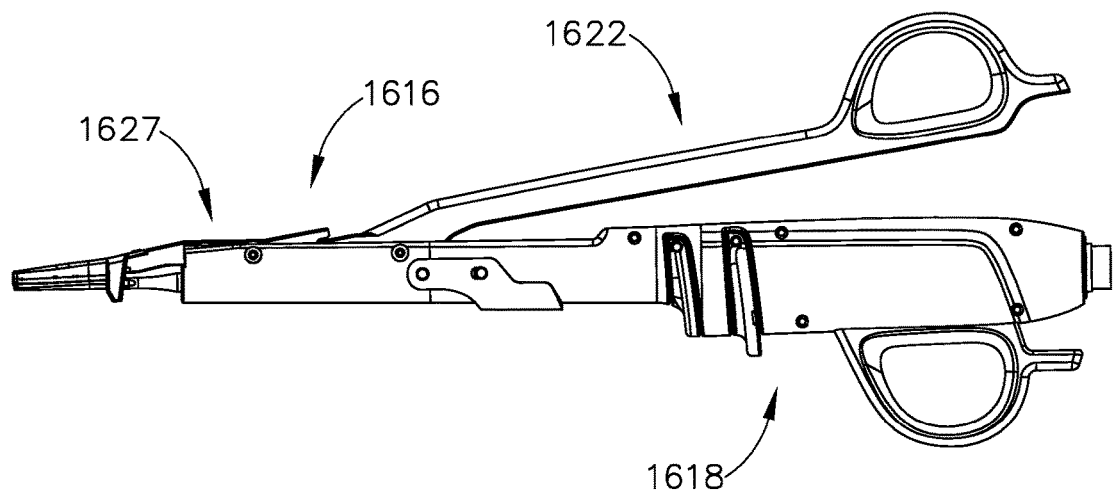
FIG. 42B depicts the schematic, enlarged sectional side view of the shaft assembly and the handle assembly similar to FIG. 42A, but showing the clamp arm assembly mechanically and electrically connected to the remainder of the surgical instrument in the operational state.

With respect to FIG. 42A, first lockout portion (1624) includes a position sensor (1640) electronically connected with controller (194). Second lockout portion (1626) includes a trigger element (1642). More particularly, position sensor (1640) is configured to provide information to controller (194) regarding the position of clamp arm assembly (1622) relative to handle assembly (1618). In some versions of electrical lockout (1616), position sensor (1640) is an optical sensor directed toward clamp arm assembly (1622) when shaft assembly (1620) is properly connected with clamp arm assembly (1622). In these versions of electrical lockout (1616), trigger element (1642) may be an optically identifiable element such as a differently colored, reflective, or otherwise distinct portion of clamp arm assembly (1622). As shown in FIG. 42B, the identifiable characteristic of trigger element (1642) allows position sensor (1640) to identify when trigger element (1642) is at a desired set location, which indicates both the presence of clamp arm assembly (1622) within handle assembly (1618) and proper alignment. In other versions of electrical lockout (1616), position sensor (1640) includes a switch and trigger element (1642) includes a fin for depressing the switch when clamp arm assembly (1622) is disposed and properly aligned within handle assembly (1618). In other versions of electrical lockout (1616), position sensor (1640) includes any sensor style mechanism for coordinating with trigger element (1642) to determine when clamp arm assembly (1622) is disposed and properly aligned within handle assembly (1618).

When position sensor (1640) identifies trigger element (1642), upon mechanical connection of clamp arm assembly (1622) to handle assembly (1618) in the predetermined alignment shown in FIG. 41, electrical lockout (1616) transitions surgical instrument (1610) from the incomplete and/or misaligned locked-out state to the operational state as discussed above with respect to transducer power circuit (170) of FIGS. 9A-9C.

Figure 43:
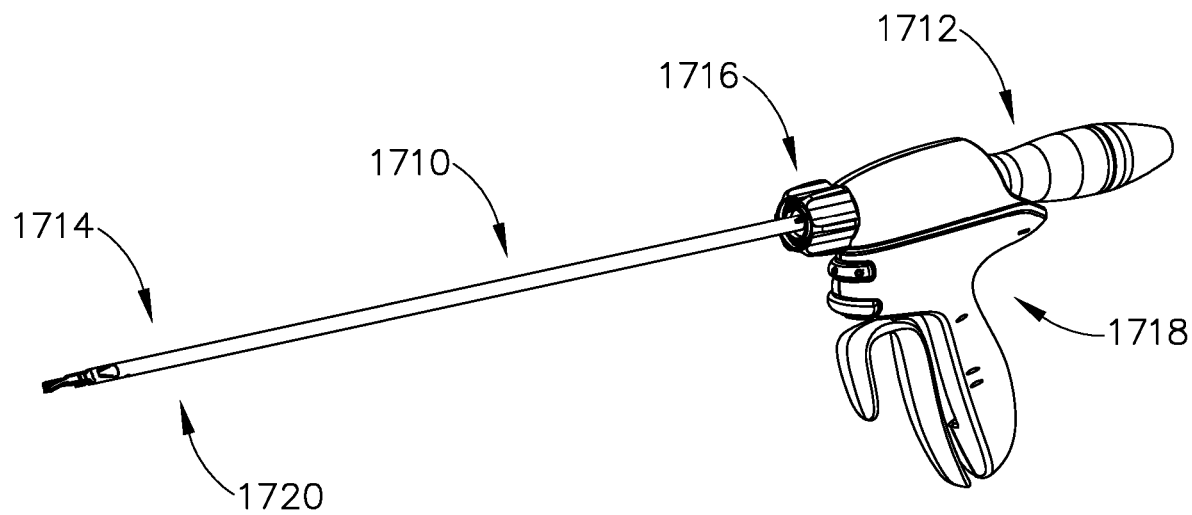
FIG. 43 depicts a schematic, perspective view of a fourteenth exemplary surgical instrument having a fifteenth example of an electrical lockout with a fifteenth modular electrical coupling with a shaft assembly mechanically and electrically connected to a handle assembly of the surgical instrument in an operational state.
Figure 44:
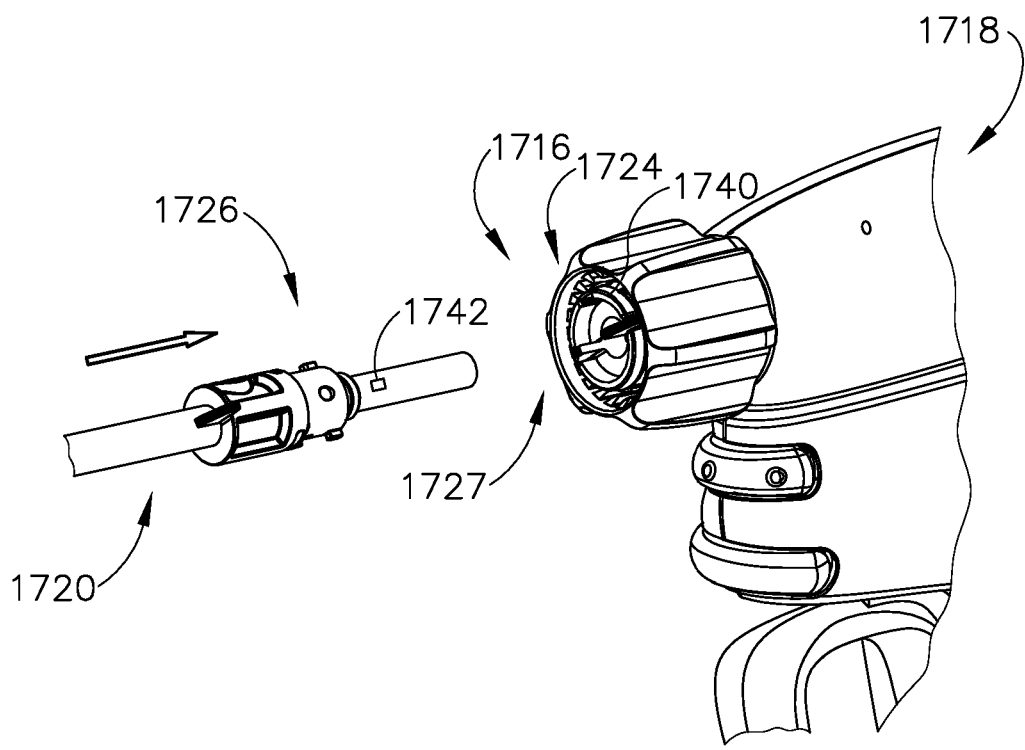
FIG. 44 depicts a schematic, enlarged perspective view of the surgical instrument of FIG. 43 having the shaft assembly being inserted into the handle assembly such that the surgical instrument is in a locked-out state.

O. Fourteenth Exemplary Ultrasonic Surgical Instrument Having a Fifteenth Example of an Electrical Lockout FIGS. 43-44 show a fourteenth exemplary ultrasonic surgical instrument (1710) including a first modular assembly (1712), a second modular assembly (1714), and a fifthteenth example of an electrical lockout (1716) for inhibiting misaligned use of surgical instrument (1710) in a locked-out state. In the present example, first modular assembly (1712) has a handle assembly (1718), whereas second modular assembly (1714) has a shaft assembly (1720) and a distally extending clamp arm assembly (1722). Electrical lockout (1716) has a first lockout portion (1724) positioned on a distal portion of handle assembly (1718) and a second lockout portion (1726) positioned on a proximal portion of shaft assembly (1720). First and second lockout portions (1724, 1726) collectively define a fifthteenth modular electrical coupling (1727) and cooperatively align as shaft assembly (1720) mechanically connects to handle assembly (1718) with a predetermined alignment to direct surgical instrument (1710) from the locked-out state to the operational state.

With respect to FIG. 44, first lockout portion (1724) includes a magnetic sensor (1740) electronically connected with controller (194) and second lockout portion (1726) includes a magnet element (1742). More particularly, magnetic sensor (1740) is configured to sense the proximity of magnet element (1742) and provide information to controller (194) regarding the position of shaft assembly (1720) relative to handle assembly (1718) based on the proximity. In some versions of electrical lockout (1716), magnetic sensor (1740) comprises a circuit board having electromagnetic sensing circuitry directed toward the desired location of magnetic element (1742) when shaft assembly (1720) is disposed within handle assembly (1718). In these versions of electrical lockout (1716), magnet element (1742) emanates an electromagnetic field from a distinct portion of shaft assembly (1720), which is sensed by magnetic sensor (1740). The circuitry of magnetic sensor (1740) may generate a range of voltages produced via the proximity of magnet (1742) to magnetic sensor (1740). One or more of the voltages in the range may be correlated to the proper alignment of handle assembly (1718) within shaft assembly (1720). In turn, magnetic sensor (1740) may be programmed to indicate to controller (194) that shaft assembly (1720) is properly aligned once the desired voltage or range of voltages is realized.

Once position sensor (1740) indicates to controller (194) that shaft assembly (1720) is disposed and properly aligned within handle assembly (1718), electrical lockout (1716) transitions surgical instrument (1710) from the incomplete and/or misaligned locked-out state to the operational state as discussed above with respect to transducer power circuit (170) of FIGS. 9A-9C.

Figure 45:
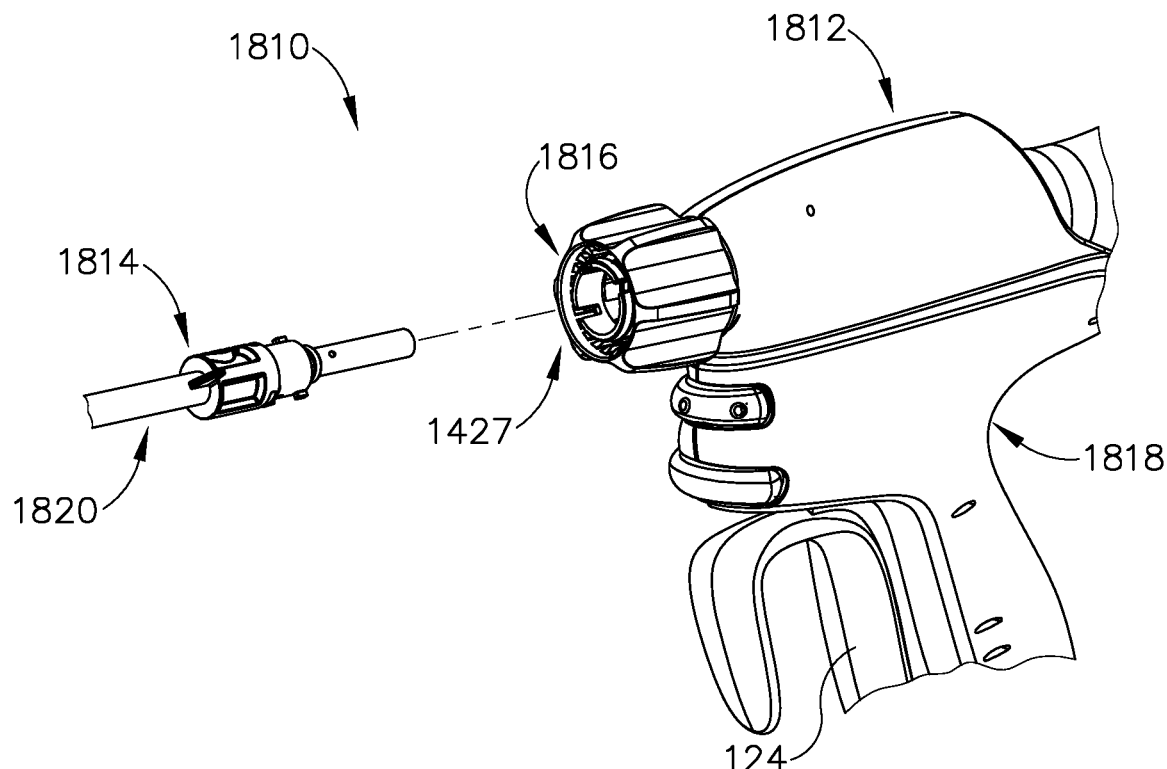
FIG. 45 depicts a schematic, perspective view of a fifteenth exemplary surgical instrument having a sixteenth example of an electrical lockout with a sixteenth modular electrical coupling with a shaft assembly mechanically and electrically disconnected from a handle assembly such that the surgical instrument in a locked-out state.

P. Fifteenth Exemplary Ultrasonic Surgical Instrument Having an Sixteenth Example of an Electrical Lockout FIGS. 45-46B show a fifteenth exemplary ultrasonic surgical instrument (1810) including a first modular assembly (1812), a second modular assembly (1814), and a sixteenth example of an electrical lockout (1816) for inhibiting misaligned use of surgical instrument (1810) in a locked-out state. In the present example, first modular assembly (1812) has a handle assembly (1818), whereas second modular assembly (1814) has a shaft assembly (1820) and a distally extending clamp arm assembly (not shown). Electrical lockout (1816) has a first lockout portion (1824) positioned on a distal portion of handle assembly (1818) and a second lockout portion (1826) positioned on a proximal portion of shaft assembly (1820). First and second lockout portions (1824, 1826) collectively define a sixteenth modular electrical coupling (1827) and cooperatively align as shaft assembly (1820) mechanically connects to handle assembly (1818) with a predetermined alignment to direct surgical instrument (1810) from the locked-out state to the operational state.

Figure 46A:
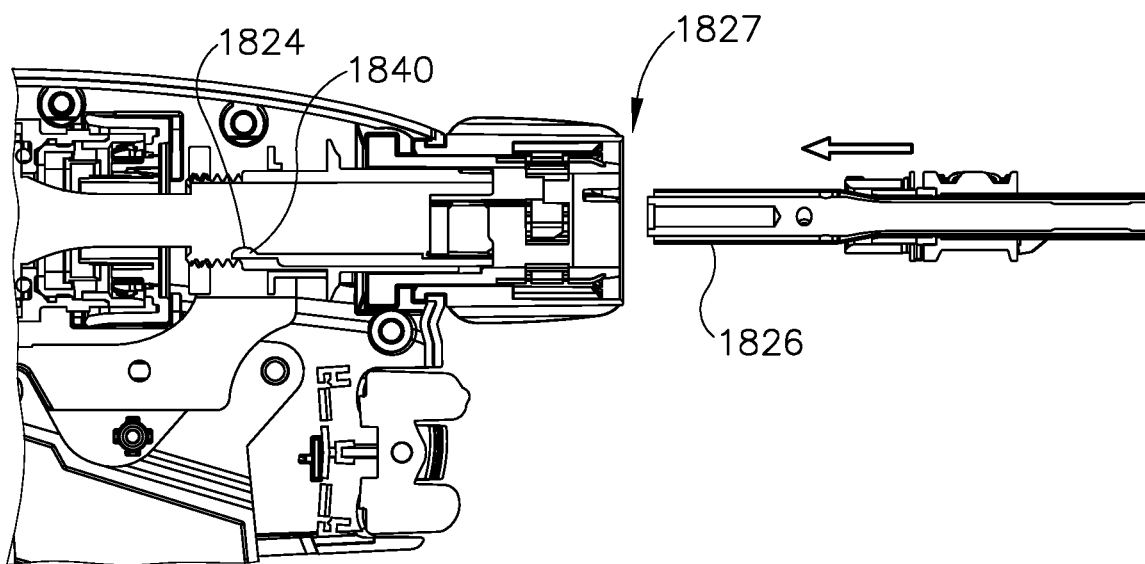
FIG. 46A depicts a schematic, enlarged sectional side view of the shaft assembly of FIG. 45 being inserted into the handle assembly in the locked-out state.
Figure 46B:
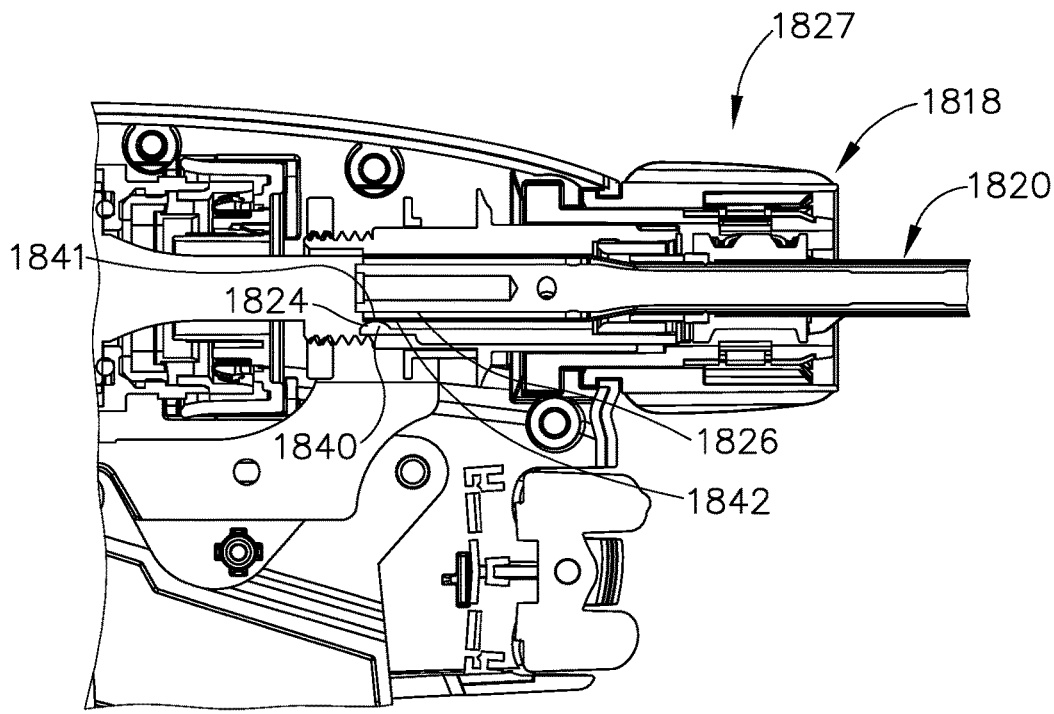
FIG. 46B depicts the schematic, enlarged sectional side view of the shaft assembly and the handle assembly similar to FIG. 46A, but showing the shaft assembly mechanically and electrically connected to the handle assembly such that the surgical instrument is in an operational state.
Figure 47:
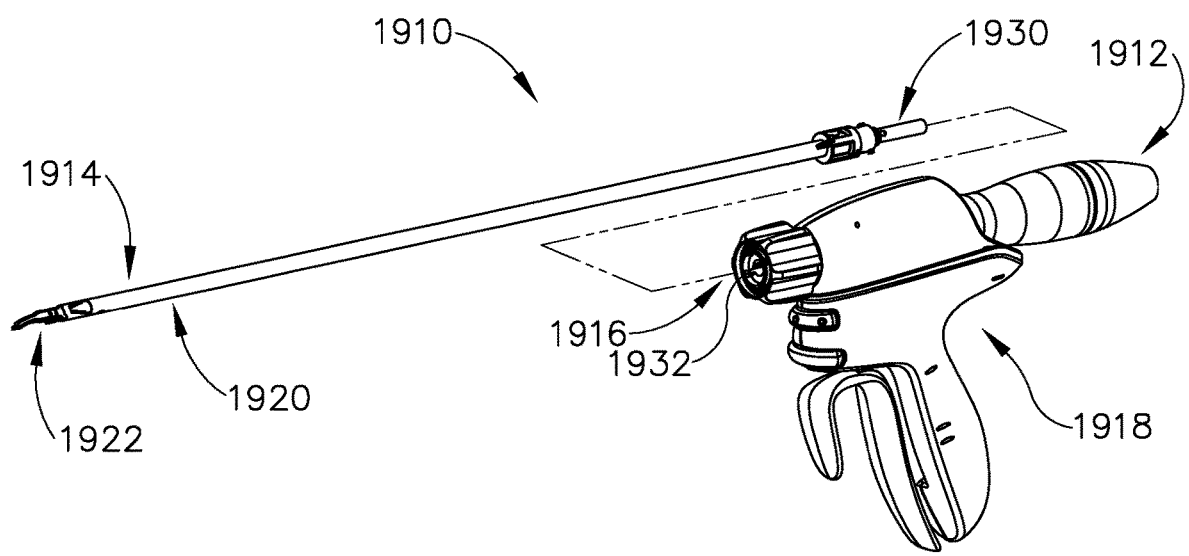
FIG. 47 depicts a schematic, perspective view of a sixteenth exemplary surgical instrument having a seventeenth example of an electrical lockout with a seventeenth modular electrical coupling with a shaft assembly mechanically and electrically disconnected from a handle assembly such that the surgical instrument in a locked-out state.

With respect to FIGS. 46A and 46B, first lockout portion (1824) includes a switch (1840) electronically connected with controller (194) and second lockout portion (1826) includes a switch actuator (1842). More particularly, switch (1840) is configured to move between a first position (FIG. 46A) and a second position (FIG. 46B) to provide information to controller (194) regarding the alignment of shaft assembly (1820) relative to handle assembly (1818). In some versions of electrical lockout (1816), switch (1840) comprises a dome switch having an arcuate surface (1841). In some versions of electrical lockout (1816), switch actuator (1842) comprises a fin, protuberance, or other style of camming surface extending outwardly away from another portion of shaft assembly (1820). In these versions of electrical lockout (1816), switch actuator (1842) is disposed and configured to slide over arcuate surface (1841) to depress switch (1840) from the first position to the second position when shaft assembly (1820) is disposed and properly aligned within handle assembly (1818). Switch (1840) in the second position indicates to controller (194) that shaft assembly (1820) is properly received and aligned within handle assembly (1818). Switch (1840) may be configured to complete a circuit in the second position, whereby the energizing of this circuit indicates to controller (194) that shaft assembly (1820) is properly aligned. In some versions of surgical instrument (1810), an alignment channel (not shown) may be provided on handle assembly (1818) to receive switch actuator (1842) and guide shaft assembly (1820) from external to handle assembly (1818) to the proper alignment therein.

Once switch (1840) indicates to controller (194) that shaft assembly (1820) is disposed and properly aligned within handle assembly (1818), electrical lockout (1816) transitions surgical instrument (1810) from the incomplete and/or misaligned locked-out state to the operational state as discussed above with respect to transducer power circuit (170) of FIGS. 9A-9C.

Figure 48:
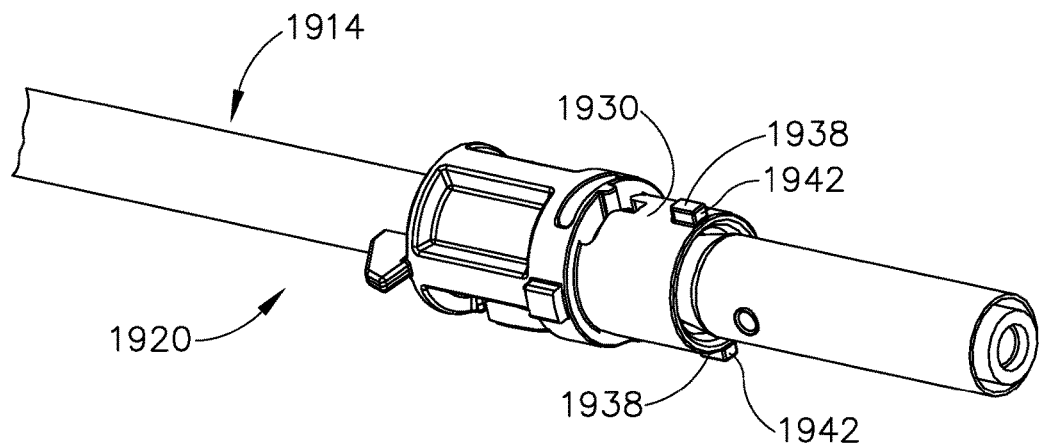
FIG. 48 depicts a schematic, perspective view of a proximal end portion of the shaft assembly of FIG. 47 having a male bayonet coupling including a portion of the modular electrical coupling.
Figure 49:
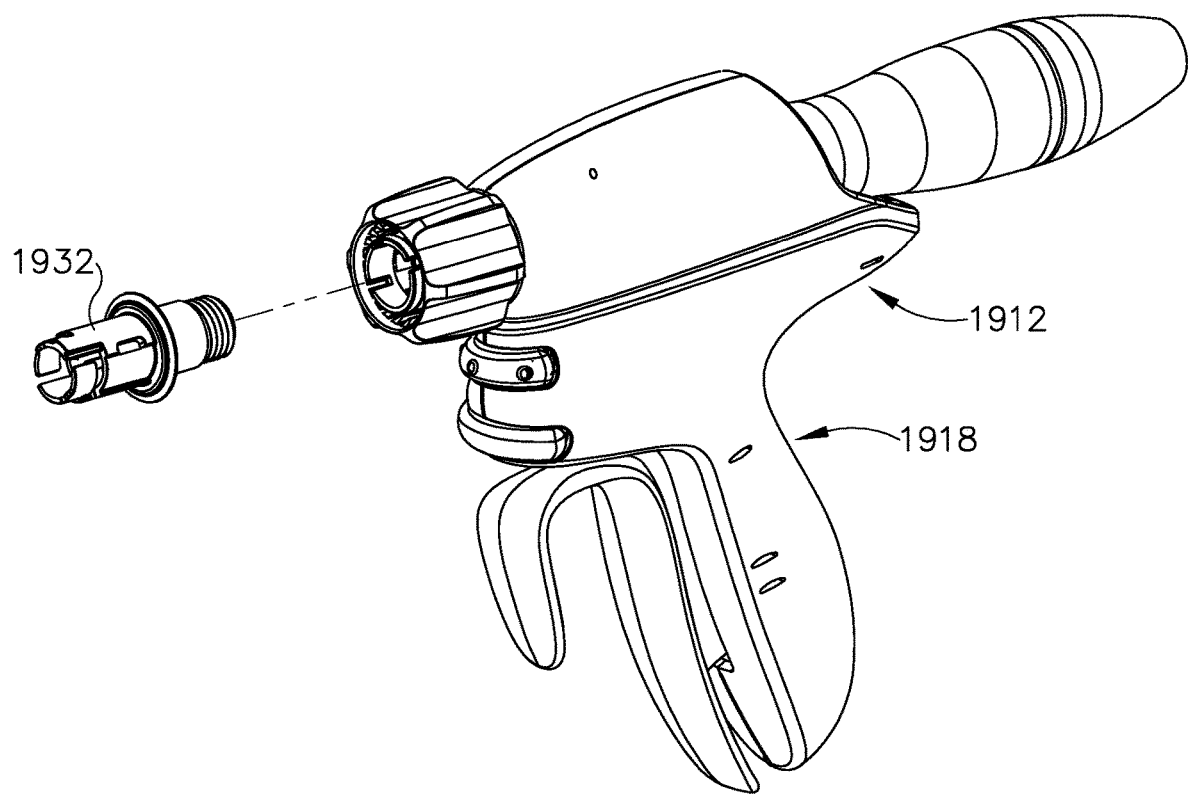
FIG. 49 depicts a schematic, partially exploded perspective view of the handle assembly of FIG. 47 having a female bayonet coupling including another portion of the module electrical coupling.
Figure 50:
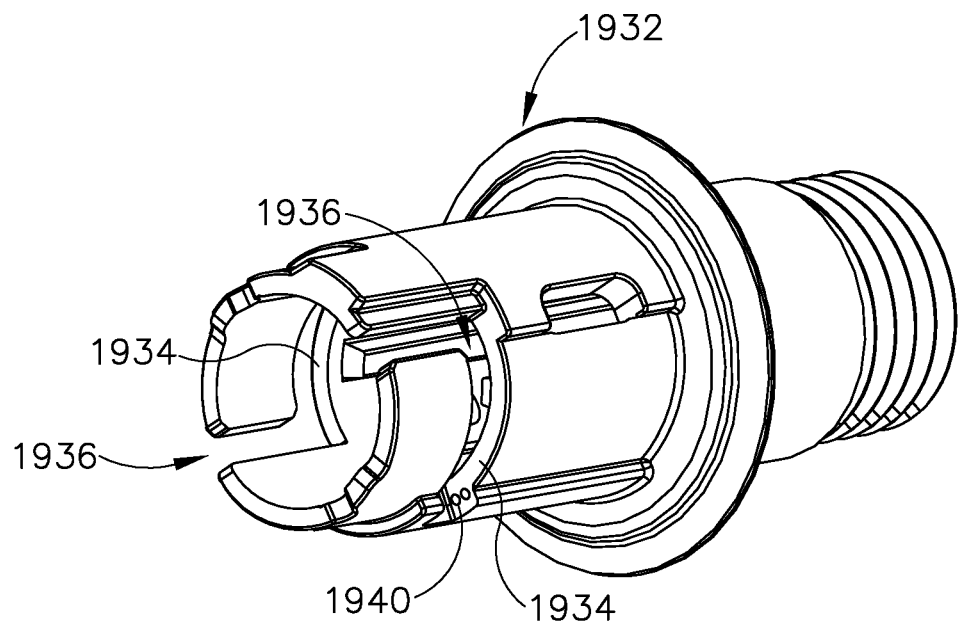
FIG. 50 depicts a schematic, perspective view of the female bayonet coupling of FIG. 49 having the portion of the modular electrical coupling.
Figure 51A:
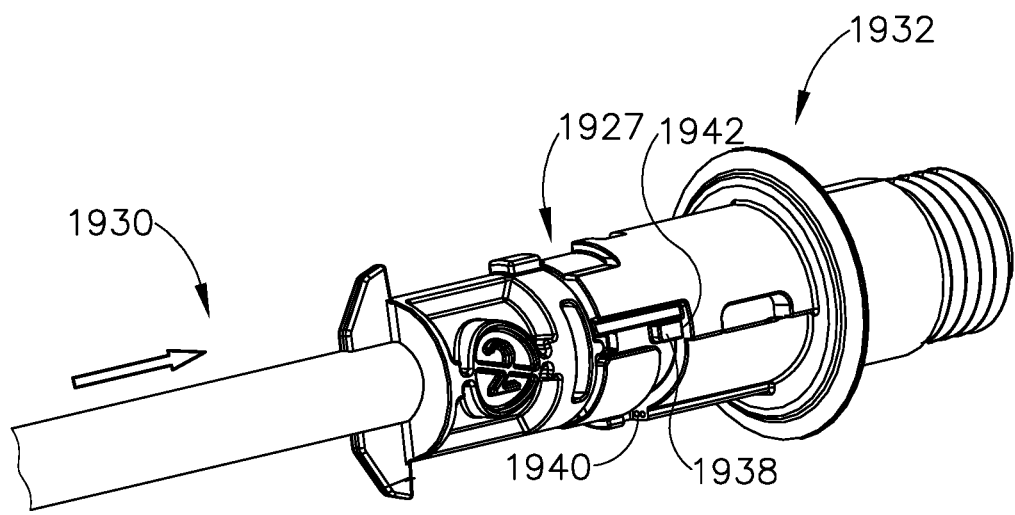
FIG. 51A depicts the male bayonet coupling of the shaft assembly of FIG. 48 being inserted into the female bayonet coupling of the handle assembly of FIG. 49 such that the surgical instrument of FIG. 49 is in a locked-out state.
Figure 51B:
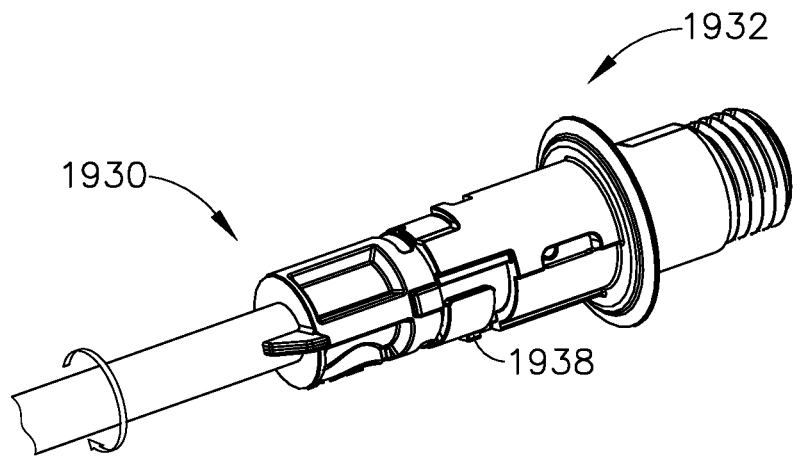
FIG. 51B depicts the male bayonet coupling of the shaft assembly of FIG. 48 being rotatably connected into the female bayonet coupling of the handle assembly of FIG. 49 such that the surgical instrument of FIG. 49 is in an operational state.

Q. Sixteenth Exemplary Ultrasonic Surgical Instrument Having a Seventeenth Example of an Electrical Lockout FIGS. 47-52 show a sixteenth exemplary ultrasonic surgical instrument (1910) including a first modular assembly (1912), a second modular assembly (1914), and a seventeenth example of an electrical lockout (1916) for inhibiting misaligned use of surgical instrument (1910) in a locked-out state. In the present example, first modular assembly (1912) has a handle assembly (1918), whereas second modular assembly (1914) has a shaft assembly (1920) and a distally extending clamp arm assembly (1922). As shown in FIG. 48, shaft assembly (1920) includes a male shaft coupler (1930) disposed at the distal end thereof. As shown in FIGS. 49 and 50, handle assembly (1918) includes a female shaft coupler (1932) for receiving male shaft coupler (1930) therein to connect shaft assembly (1920) with handle assembly (1918).

Electrical lockout (1916) has a first lockout portion (1924) positioned on a distal portion of handle assembly (1918) and a second lockout portion (1926) positioned on a proximal portion of shaft assembly (1920). First and second lockout portions (1924, 1926) collectively define a seventeenth modular electrical coupling (1927) and cooperatively align as shaft assembly (1920) mechanically connects to handle assembly (1918) with a predetermined alignment to direct surgical instrument (1910) from the locked-out state to the operational state. In some versions of electrical lockout (1916), first lockout portion (1924) is disposed on female shaft assembly (1932) and second lockout portion (1926) is disposed on male shaft assembly (1930).

As shown in FIGS. 49-51B, in some versions of electrical lockout (1916), first lockout portion (1924) is incorporated into or disposed on a lock channel surface (1934) which defines a lock channel (1936) of female shaft assembly (1932). First lockout portion (1924) comprises a pair of contacts (1940) positioned proximate one another. Contacts (1940) are terminal ends of a circuit, which is incomplete due to contacts (1940) being spaced apart. Second lockout portion (1926) is disposed on a corresponding locking fin (1938) of male shaft assembly (1930) and comprises a bridge element (1942) formed of electrically conductive material. Bridge element (1942) is sized to overlap both contacts (1940) and complete the circuit by providing an electrical pathway between contacts (1930). Locking fins (1938) are sized to enter lock channel (1936) as shown in FIG. 51A. As the user manually rotates shaft assembly (1920) to the proper alignment within handle assembly (1918), locking fins (1938) move to abut lock channel surface (1934). Once shaft assembly (1920) achieves proper alignment, bridge element (1942) is oriented to overlap both contacts (1940) and complete the circuit. Inasmuch as controller (194) is incorporated into the circuit, controller (194) is configured to sense the completion of the circuit and recognize shaft assembly (1920) is properly aligned within shaft assembly (1918). Upon sensing the completion of the circuit, controller (194) is configured to transition surgical instrument (1910) from the incomplete and/or misaligned locked-out state to the operational state as discussed above with respect to transducer power circuit (170) of FIGS. 9A-9C when the circuit is closed and completed.

Figure 52:
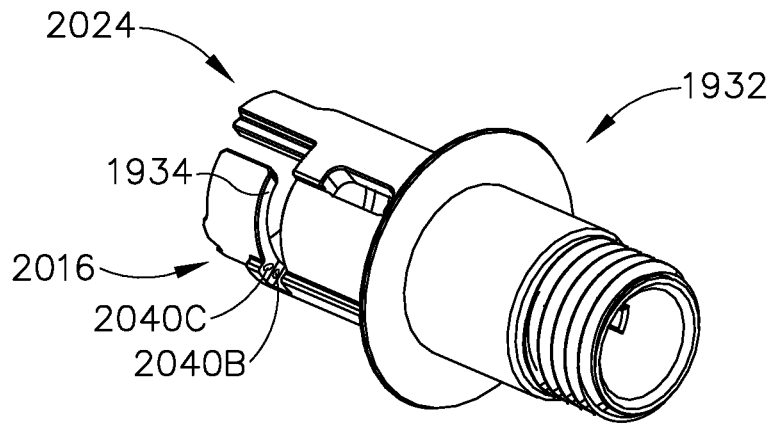
FIG. 52 depicts a schematic, perspective view of another female bayonet coupling having the portion of the modular electrical coupling of FIG. 50.

As shown in FIG. 52, contacts (1936) may be disposed at other locations along lock channel surface (1934), with the location of bridge element (1942) necessarily changing to allow for the completing of the circuit by bridge element (1942) abutting both contacts (1936).

Once electrical lockout (1916) indicates to controller (194) that shaft assembly (1920) is disposed and properly aligned within handle assembly (1918), electrical lockout (1916) transitions surgical instrument (1910) from the incomplete and/or misaligned locked-out state to the operational state as discussed above with respect to transducer power circuit (170) of FIGS. 9A-9C.

Figure 53:
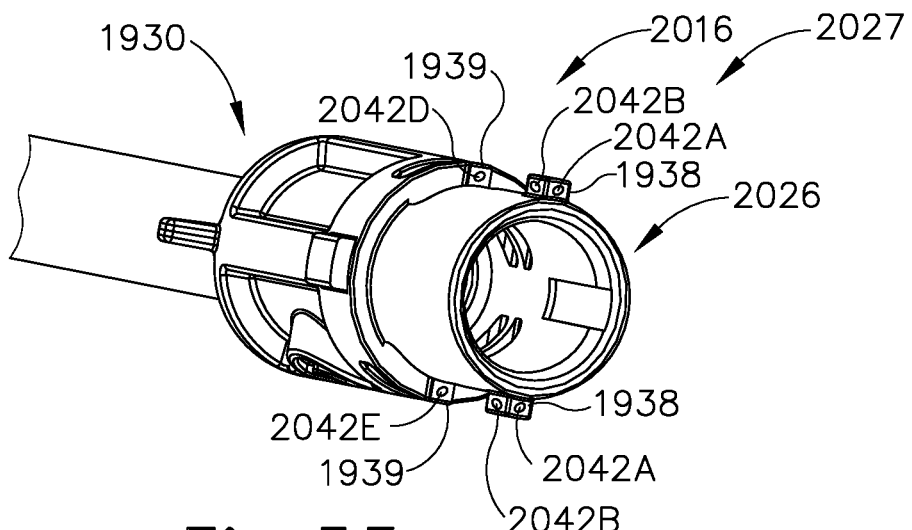
FIG. 53 depicts a schematic, perspective view of a proximal end portion of the shaft assembly of FIG. 47 having a male bayonet coupling including at least a portion of an eighteenth example of an electrical lockout with an eighteenth modular electrical coupling.
Figure 55:
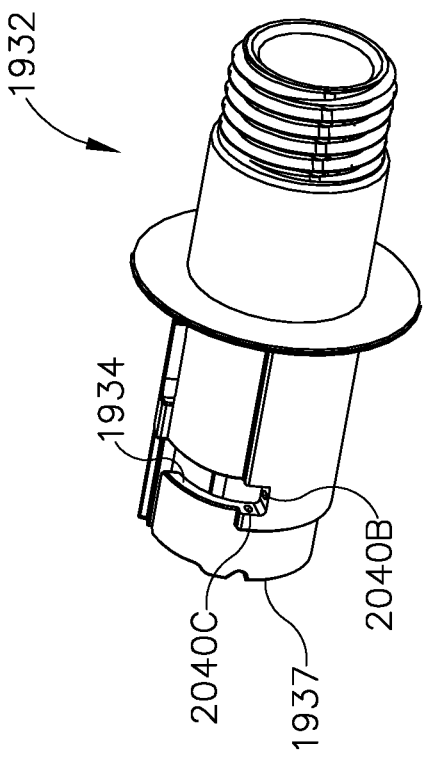
FIG. 55 depicts a schematic, proximal perspective view of the female bayonet coupling of FIG. 54 including at least another portion of the electrical lockout with the modular electrical coupling of FIG. 53.
Figure 54:
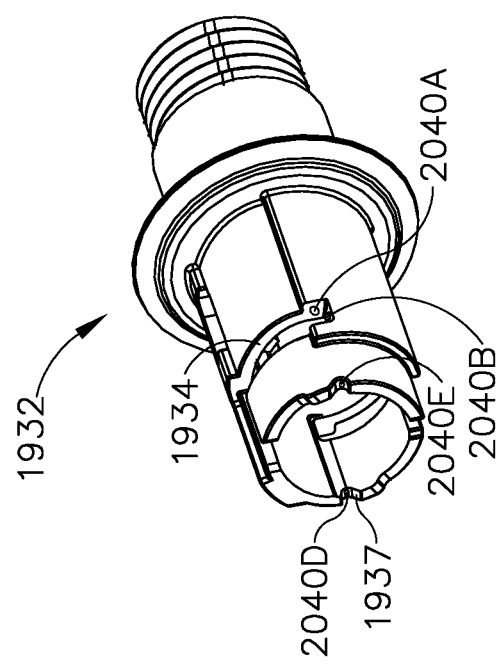
FIG. 54 depicts a schematic, proximal perspective view of a female bayonet coupling of the handle assembly of FIG. 47 including at least another portion of the electrical lockout with the modular electrical coupling of FIG. 53.

R. Sixteenth Exemplary Ultrasonic Surgical Instrument Having a Eighteenth Example of an Electrical Lockout FIGS. 53-55 show the sixteenth exemplary ultrasonic surgical instrument (1910) and an eighteenth example of an electrical lockout (2016) for inhibiting misaligned use of surgical instrument (1910) in a locked-out state. Electrical lockout (2016) has a first lockout portion (2024) positioned on a distal portion of handle assembly (1918) and a second lockout portion (2026) positioned on a proximal portion of shaft assembly (1920). First and second lockout portions (2024, 2026) collectively define an eighteenth modular electrical coupling (2027) and cooperatively align as shaft assembly (1920) mechanically connects to handle assembly (1918) with a predetermined alignment to direct surgical instrument (1910) from the locked-out state to the operational state. In some versions of electrical lockout (2016), first lockout portion (2024) is disposed on female shaft coupler (1932) and second lockout portion (2026) is disposed on male shaft coupler (1930).

As shown in FIGS. 54 and 55, in some versions of electrical lockout (2016), first lockout portion (2024) includes a Hall Effect sensor (2040) for sensing the proximity of a magnet. Hall Effect sensor (2040) is coupled with controller (194) to notify controller (194) of the presence or absence of a magnet proximate Hall Effect sensor (2040). One or more Hall Effect sensors (2040) may be located anywhere along female shaft coupler (1932). For example, as shown in FIG. 54, in some versions, Hall Effect sensor (2040) may be incorporated into or disposed at various locations along lock channel surface (1934), shown as Hall Effect sensors (2040A, 2040B, 2040C). In other versions, Hall Effect sensor (2040) may be incorporated into or disposed at various locations along a notch recess (1937), shown as Hall Effect sensors (2040D, 2040E).

As shown in FIG. 53, in some versions of electrical lockout (2016), second lockout portion (2026) includes a magnet (2042) for actuating Hall Effect sensor (2040) when shaft assembly (1920) is in proper alignment with handle assembly (1918). For example, in some versions, magnet (2042) may be incorporated into or disposed at various locations along locking fin (1938) of male shaft coupler (1930), shown in FIG. 53 as magnets (2042A, 2042B). In other versions, magnet (2042) may be incorporated into or disposed at various locations along a notch (1939) of male shaft coupler (1930), shown in FIG. 53 as magnets (2042C, 2042D). Magnet (2042) is sized and positioned on male shaft coupler (1930) to actuate Hall Effect sensor (2040) when shaft assembly (1920) is disposed and properly aligned within handle assembly (1918). When Hall Effect sensor (2040) is actuated by magnet (2042), Hall Effect sensor (2040) signals to controller (194) surgical instrument (1910) is properly assembled.

Once electrical lockout (2016) indicates to controller (194) that shaft assembly (1920) is disposed and properly aligned within handle assembly (1918), electrical lockout (2016) transitions surgical instrument (1910) from the incomplete and/or misaligned locked-out state to the operational state as discussed above with respect to transducer power circuit (170) of FIGS. 9A-9C.

Figure 56:
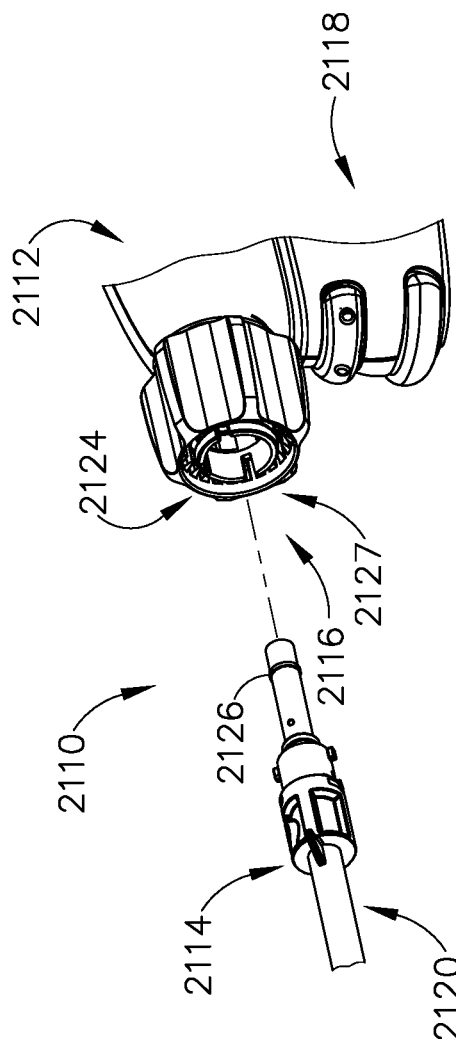
FIG. 56 depicts a schematic, perspective view of a seventeenth exemplary surgical instrument having a nineteenth example of an electrical lockout with a nineteenth modular electrical coupling with a shaft assembly mechanically and electrically disconnected from a handle assembly such that the surgical instrument in a locked-out state.

S. Seventeenth Exemplary Ultrasonic Surgical Instrument Having a Nineteenth Example of an Electrical Lockout FIGS. 56-57B show a seventeenth exemplary ultrasonic surgical instrument (2110) including a first modular assembly (2112), a second modular assembly (2114), and a nineteenth example of an electrical lockout (2116) for inhibiting misaligned use of surgical instrument (2110) in a locked-out state. In the present example, first modular assembly (2112) has a handle assembly (2118), whereas second modular assembly (2114) has a shaft assembly (2120) and a distally extending clamp arm assembly (not shown). Electrical lockout (2116) has a first lockout portion (2124) positioned on a distal portion of handle assembly (2118) and a second lockout portion (2126) positioned on a proximal portion of shaft assembly (2120). First and second lockout portions (2124, 2126) collectively define a nineteenth modular electrical coupling (2127) and cooperatively align as shaft assembly (2120) mechanically connects to handle assembly (2118) with a predetermined alignment to direct surgical instrument (2110) from the locked-out state to the operational state.

Figure 57A:
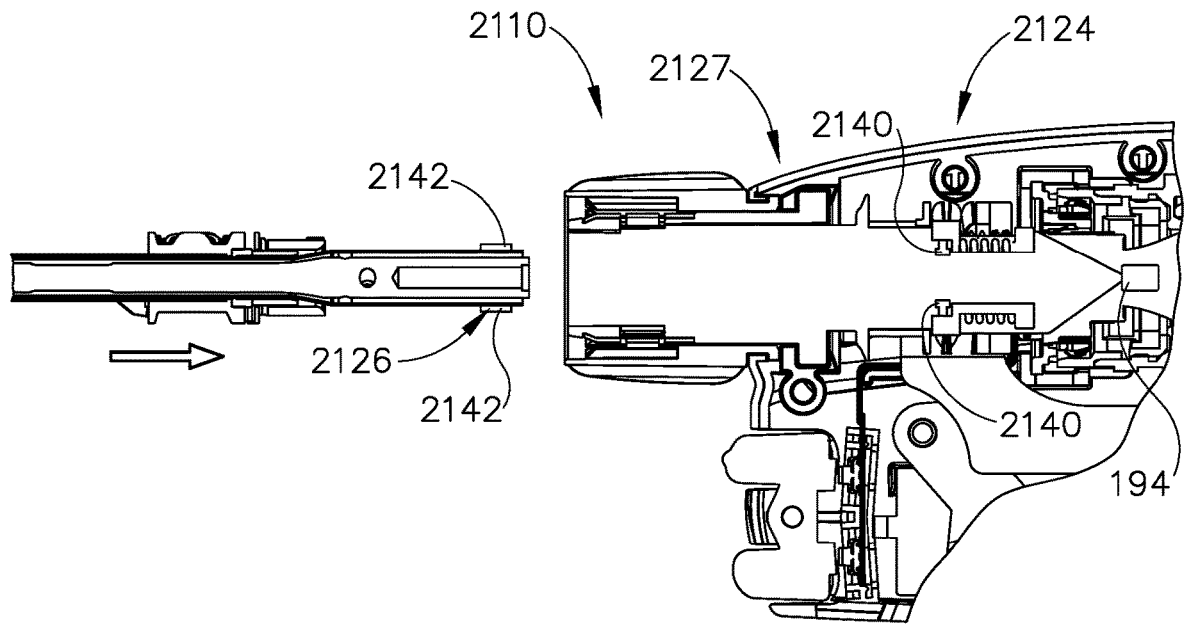
FIG. 57A depicts a schematic, enlarged sectional side view of the shaft assembly of FIG. 56 being inserted into the handle assembly in the locked-out state.
Figure 57B:
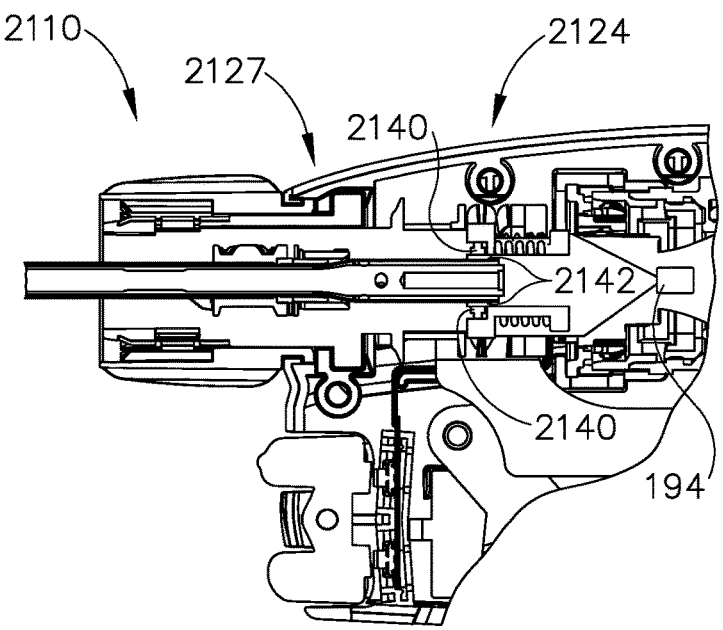
FIG. 57B depicts the schematic, enlarged sectional side view of the shaft assembly and the handle assembly similar to FIG. 57A, but showing the shaft assembly mechanically and electrically connected to the handle assembly such that the surgical instrument is in an operational state.

With respect to FIGS. 57A and 57B, first lockout portion (2124) includes a pair of contacts (2140) electronically connected with controller (194). Each contact (2140) may be independently electronically connected to controller (194). Second lockout portion (2126) includes a contact ring (2142). More particularly, contact ring (2142) is sized and positioned to abut each of the pair of contacts (2140) when shaft assembly (2020) is properly connected with handle assembly (2118). When properly connected, contact ring (2142) of shaft assembly (2120) provides a bridge between the pair of contacts (2140) to complete a closed circuit with controller (194). Controller (194) is configured to sense the completion of the closed circuit and indicate to the user shaft assembly (2020) is properly connected with handle assembly (2018) and surgical instrument (2110) is properly assembled. A display screen (not shown) or other feedback mechanism may be used to indicate to the user the proper or improper assembly of surgical instrument (2110). For example, when contact ring (2142) is not contacting each of the pair of contacts (2140), the controller may be programmed to provide an error screen message to the user.

When contact ring (2142) is moved to proper alignment with respect to the pair of contacts (2140) to complete the circuit, controller (194) may be programmed to provide a message to the user indicating surgical instrument (2110) is properly assembled.

Once the circuit is complete via contact ring (2142) connecting the pair of contacts (2140) to indicate to controller (194) that shaft assembly (2120) is disposed and properly aligned within handle assembly (2118), electrical lockout (2116) transitions surgical instrument (2110) from the incomplete and/or misaligned locked-out state to the operational state as discussed above with respect to transducer power circuit (170) of FIGS. 9A-9C.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) a first modular assembly, including: (i) at least a portion of an end effector configured to manipulate a tissue; (b) a second modular assembly configured to mechanically couple with the first modular assembly in a predetermined alignment relative to each other, wherein the second modular assembly includes: (i) a body assembly configured to support an ultrasonic transducer; (ii) a transducer power circuit configured to electrically connect to the ultrasonic transducer and a generator, and (iii) an activation switch electrically connected to the transducer power circuit, wherein the activation switch is configured to selectively power the ultrasonic transducer by directing electrical power from the generator to the ultrasonic transducer with the first and second modular assemblies in the predetermined alignment, and (c) an electrical lockout electrically connected to the transducer power circuit, wherein the electrical lockout is configured to inhibit the activation switch from powering the ultrasonic transducer with the first and second modular assemblies misaligned from the predetermined alignment such that the first and second modular assemblies are in a locked-out state, and wherein the electrical lockout is further configured to allow the activation switch to power the ultrasonic transducer with the first and second modular assemblies in the predetermined alignment such that the first and second modular assemblies are in an operational state.

Example 2

The ultrasonic surgical instrument of Example 1, wherein the first modular assembly further includes a shaft assembly, wherein the shaft assembly includes an acoustic waveguide extending therealong and the end effector projecting distally therefrom, and wherein the at least the portion of the end effector further includes an ultrasonic blade extending from the acoustic waveguide.

Example 3

The ultrasonic surgical instrument of any one or more of Examples 1 through 2, wherein the at least the portion of the end effector further includes a clamp arm assembly movably connected relative to the ultrasonic blade and configured to compress the tissue against the ultrasonic blade.

Example 4

The ultrasonic surgical instrument of Example 1, wherein the second modular assembly further includes an acoustic waveguide extending to an ultrasonic blade, wherein the at least the portion of the end effector of the first modular assembly further includes a clamp arm assembly, wherein the clamp arm assembly is configured to be movably connected relative to the ultrasonic blade to compress the tissue against the ultrasonic blade.

Example 5

The ultrasonic surgical instrument of any one or more of Examples 1 through 4, wherein the body assembly second modular assembly further includes an ultrasonic transducer supported therein.

Example 6

The ultrasonic surgical instrument of any one or more of Examples 1 through 5, wherein the electrical lockout further includes a first lockout portion positioned on the first modular assembly and a second lockout portion electrically connected to the transducer power circuit and positioned on the body, wherein the second lockout portion is configured to inhibit the transducer power circuit from powering the ultrasonic transducer in the locked-out state, and wherein the first and second lockout portion in the predetermined alignment are collectively configured to allow the activation switch to power the ultrasonic transducer in the operational state.

Example 7

The ultrasonic surgical instrument of Example 6, wherein the first lockout portion includes a first electrical shut, wherein the second lockout portion includes a first pair of electrical contacts, wherein the first pair of electrical contacts define a first electrical gap in the locked-out state to inhibit electrical flow between the first pair of electrical contacts, wherein the first electrical shunt in the predetermined alignment electrically connects the first pair of electrical contacts for the operational state.

Example 8

The ultrasonic surgical instrument of Example 7, wherein the first lockout portion includes a second electrical shut, wherein the second lockout portion includes a second pair of electrical contacts, wherein the second pair of electrical contacts defines a second electrical gap in the locked-out state to inhibit electrical flow between the second pair of electrical contacts, wherein the second electrical shunt in the predetermined alignment electrically connects the second pair of electrical contacts for the operational state.

Example 9

The surgical instrument of Example 6, wherein the first lockout portion includes a first metallic member, wherein the second lockout portion includes a second metallic member, wherein the first metallic member and the second metallic member in the predetermined alignment collectively define an electrical capacitor, and wherein the electrical capacitor is configured to generate a capacitance in the predetermined alignment for the operational state.

Example 10

The surgical instrument of Example 6 wherein the first lockout portion includes a first metallic member, wherein the second lockout portion includes an electrical coil, wherein the electrical coil receives the metallic member in the predetermined alignment to collectively define an electrical inductor, wherein the electrical inductor is configured to generator an inductance in the predetermined alignment for the operational state.

Example 11

The surgical instrument of Example 6, wherein the first lockout portion includes a reflective surface, wherein the second lockout portion includes an infrared light source and an infrared receiver, wherein the infrared light source is configured to direct infrared light to reflect from the reflective surface and into the infrared receiver in the predetermined alignment for the operational state.

Example 12

The surgical instrument of Example 6, wherein the first lockout portion includes a ramp surface, wherein the second lockout portion includes a movable member connected to a potentiometer, wherein the movable member is configured to be moved by the ramp surface from a disconnected position, through an intermediate position, and to a connected position as the first modular assembly is being mechanically connected to the second modular assembly with the predetermined alignment, wherein the movable member in the disconnected position directs the potentiometer to generate a disconnected voltage for indicating that the first modular assembly is completely disconnected from the second modular assembly and in the locked-out state, wherein the movable member in the intermediate position directs the potentiometer to generate an intermediate voltage for indicating that the first modular assembly is partially connected to the second modular assembly and in the locked-out state, and wherein the movable member in the connected position directs the potentiometer to generate a connected voltage for indicating that the first modular assembly is connected to the second modular assembly with the predetermined alignment in the operational state.

Example 13

The ultrasonic surgical instrument of Example 6, wherein the first lockout portion includes an abutment surface on the first modular assembly, wherein the second lockout portion includes a pair of electrical contacts and a movable member having an electrical shunt positioned thereon configured to move from a first position to a second position, wherein the pair of electrical contacts define an electrical gap in the locked-out state to inhibit electrical flow between the pair of electrical contacts with the movable member in the first position, wherein the abutment surface is configured to urge the movable member from the first position to the second position as the first modular assembly is mechanically connected to the second modular assembly with the predetermined alignment, and wherein the electrical shunt in the second position with the predetermined alignment electrically connects the pair of electrical contacts for the operational state.

Example 14

The ultrasonic surgical instrument of Example 6, wherein the first lockout portion includes a magnet on the first modular assembly, wherein the second lockout portion includes a pair of electrical contacts and a movable member having an electrical shunt positioned thereon configured to move from a first position to a second position, wherein the pair of electrical contacts define an electrical gap in the locked-out state to inhibit electrical flow between the pair of electrical contacts with the movable member in the first position, wherein the magnet is configured to urge the movable member from the first position to the second position as the first modular assembly is mechanically connected to the second modular assembly with the predetermined alignment, and wherein the electrical shunt in the second position with the predetermined alignment electrically connects the pair of electrical contacts for the operational state.

Example 15

The ultrasonic surgical instrument of Example 6, wherein the first lockout portion includes an abutment surface on the first modular assembly, wherein the second lockout portion includes a resiliently mounted movable member operatively connected to a force sensor and configured to move from a first position to a second position, wherein the force sensor in a first position is configured to measure an inoperable force in the locked-out state, wherein the abutment surface is configured to urge the movable member from the first position to the second position as the first modular assembly is mechanically connected to the second modular assembly with the predetermined alignment, and wherein the force sensor in the second position with the predetermined alignment is configured to measure an operable force for the operational state.

Example 16

An ultrasonic surgical instrument, comprising: (a) a first modular assembly, including: (i) a shaft assembly having an acoustic waveguide extending therealong, (ii) an end effector projecting distally from the shaft assembly, wherein the end effector further includes configured to manipulate a tissue, wherein the end effector includes an ultrasonic blade extending from the acoustic waveguide and a clamp arm assembly movably connected relative to the ultrasonic blade and configured to compress the tissue against the ultrasonic blade; (b) a second modular assembly configured to mechanically couple with the first modular assembly in a predetermined alignment relative to each other, wherein the second modular assembly includes: (i) a body assembly configured to support an ultrasonic transducer; (ii) a transducer power circuit configured to electrically connect to the ultrasonic transducer and a generator, and (iii) an activation switch electrically connected to the transducer power circuit, wherein the activation switch is configured to selectively power the ultrasonic transducer by directing electrical power from the generator to the ultrasonic transducer with the first and second modular assemblies in the predetermined alignment, and (c) an electrical lockout configured to inhibit the activation switch from powering the ultrasonic transducer with the first and second modular assemblies misaligned from the predetermined alignment such that the first and second modular assemblies are in a locked-out state, wherein the electrical lockout is further configured to allow the activation switch to power the ultrasonic transducer with the first and second modular assemblies in the predetermined alignment such that the first and second modular assemblies are in an operational state, wherein the electrical lockout includes: (i) a first lockout portion positioned on the first modular assembly, and (ii) a second lockout portion electrically connected to the transducer power circuit and positioned on the body, wherein the second lockout portion is configured to inhibit the transducer power circuit from powering the ultrasonic transducer in the locked-out state, and wherein the first and second lockout portion in the predetermined alignment are collectively configured to allow the activation switch to power the ultrasonic transducer in the operational state.

Example 17

The ultrasonic surgical instrument of Example 16, wherein the second modular assembly further includes an ultrasonic transducer supported therein.

Example 18

The ultrasonic surgical instrument of any one or more of Examples 16 through 17, wherein the first lockout portion includes a first electrical shut, wherein the second lockout portion includes a first pair of electrical contacts, wherein the first pair of electrical contacts define a first electrical gap in the locked-out state to inhibit electrical flow between the first pair of electrical contacts, wherein the first electrical shunt in the predetermined alignment electrically connects the first pair of electrical contacts for the operational state.

Example 19

A method of aligning an ultrasonic surgical instrument during assembly with a predetermined alignment, wherein the ultrasonic surgical instrument includes (a) a first modular assembly, including: (i) at least a portion of an end effector configured to manipulate a tissue; (b) a second modular assembly configured to mechanically couple with the first modular assembly in the predetermined alignment relative to each other, wherein the second modular assembly includes: (i) a body assembly configured to support an ultrasonic transducer; (ii) a transducer power circuit configured to electrically connect to the ultrasonic transducer and a generator, and (iii) an activation switch electrically connected to the transducer power circuit, wherein the activation switch is configured to selectively power the ultrasonic transducer by directing electrical power from the generator to the ultrasonic transducer with the first and second modular assemblies in the predetermined alignment, and (c) an electrical lockout electrically connected to the transducer power circuit, the method comprising: (a) inhibiting the activation switch from powering the ultrasonic transducer via the electrical lockout with the first and second modular assemblies misaligned from the predetermined alignment such that the first and second modular assemblies are in a locked-out state.

Example 20

The method of Example 19, further comprising: mechanically coupling the first modular assembly to the second modular assembly with the predetermined alignment such that the electrical lockout allows the activation switch to power the ultrasonic transducer in an operational state.

VI. Miscellaneous

It should be understood that the various teachings herein may be readily combined with the various teachings of U.S. Patent application. Ser. No. 15/284,819, entitled "Surgical Instrument with Dual Mode End Effector and Side-Loaded Clamp Arm Assembly," filed on Oct. 4, 2016, published as U.S. Pub. No. 2017/0105754 on Apr. 20, 2017, the disclosure of which is incorporated by reference herein. Various suitable ways in which the teachings herein may be combined with the teachings of U.S. patent application Ser. No. 15/284,819, published as U.S. Pub. No. 2017/0105754 on Apr. 20, 2017, will be apparent to those of ordinary skill in the art.

It should be understood that the various teachings herein may be readily combined with the various teachings of U.S. Patent application. Ser. No. 15/284,837, entitled "Surgical Instrument with Dual Mode End Effector and Compound Lever with Detents," filed on Oct. 4, 2016, published as U.S. Pub. No. 2017/0105755 on Apr. 20, 2017, the disclosure of which is incorporated by reference herein. Various suitable ways in which the teachings herein may be combined with the teachings of U.S. patent application Ser. No. 15/284,837, published as U.S. Pub. No. 2017/0105755 on Apr. 20, 2017, will be apparent to those of ordinary skill in the art.

It should be understood that the various teachings herein may be readily combined with the various teachings of U.S. patent application Ser. No. 15/284,855, entitled "Surgical Instrument with Dual Mode End Effector and Modular Clamp Arm Assembly," filed on Oct. 4, 2016, issued as U.S. Pat. No. 10,893,914 on Jan. 19, 2021, the disclosure of which is incorporated by reference herein. Various suitable ways in which the teachings herein may be combined with the teachings of U.S. patent application Ser. No. 15/284,855, issued as U.S. Pat. No. 10,893,914 on Jan. 19, 2021, will be apparent to those of ordinary skill in the art.

The various instruments described above may be used in a variety of kinds of surgical procedures. By way of example only, the instruments described above may be used to perform liver resection, colorectal surgical procedures, gynecological surgical procedures, and/or various other kinds of surgical procedures. Various other kinds of procedures and ways in which the instruments described above may be used will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
   (a) a first modular assembly, including:
      (i) at least a portion of an end effector configured to manipulate a tissue;
   (b) a second modular assembly configured to mechanically couple with the first modular assembly at a mechanical coupling in a predetermined alignment relative to each other such that the first and second modular assemblies are radially fixed relative to each other at the mechanical coupling, wherein the second modular assembly includes:
      (i) a body assembly configured to support an ultrasonic transducer,
      (ii) a transducer power circuit configured to electrically connect to the ultrasonic transducer and a generator, and
      (iii) an activation switch electrically connected to the transducer power circuit, wherein the activation switch is configured to selectively power the ultrasonic transducer by directing electrical power from the generator to the ultrasonic transducer with the first and second modular assemblies in the predetermined alignment; and
   (c) an electrical lockout electrically connected to the transducer power circuit,
   wherein the electrical lockout is configured to inhibit the activation switch from powering the ultrasonic transducer with the first and second modular assemblies misaligned from the predetermined alignment such that the first and second modular assemblies are in a locked-out state, and
   wherein the electrical lockout is further configured to allow the activation switch to power the ultrasonic transducer with the first and second modular assemblies in the predetermined alignment such that the first and second modular assemblies are in an operational state,
   wherein the electrical lockout further includes a first lockout portion positioned on the first modular assembly and a second lockout portion electrically connected to the transducer power circuit and positioned on the body, wherein the second lockout portion is not electrically connected to the first lockout portion in the locked-out state and thereby configured to inhibit the transducer power circuit from powering the ultrasonic transducer in the locked-out state, and wherein the first and second lockout portion in the predetermined alignment are electrically connected in the operational state and collectively configured to allow the activation switch to power the ultrasonic transducer in the operational state.

2. The ultrasonic surgical instrument of claim 1, wherein the first modular assembly further includes a shaft assembly, wherein the shaft assembly includes an acoustic waveguide extending therealong and the at least the portion of the end effector projecting distally therefrom, and wherein the at least the portion of the end effector further includes an ultrasonic blade extending from the acoustic waveguide.

3. The ultrasonic surgical instrument of claim 2, wherein the at least the portion of the end effector further includes a clamp arm assembly movably connected relative to the ultrasonic blade and configured to compress the tissue against the ultrasonic blade.

4. The ultrasonic surgical instrument of claim 1, wherein the second modular assembly further includes an acoustic waveguide extending to an ultrasonic blade, wherein the at least the portion of the end effector of the first modular assembly further includes a clamp arm assembly, wherein the clamp arm assembly is configured to be movably connected relative to the ultrasonic blade to compress the tissue against the ultrasonic blade.

5. The ultrasonic surgical instrument of claim 1, wherein the body assembly of the second modular assembly further includes an ultrasonic transducer supported therein.

6. The ultrasonic surgical instrument of claim 1, wherein the electrical lockout further includes a first lockout portion positioned on the first modular assembly and a second lockout portion electrically connected to the transducer power circuit and positioned on the body, wherein the second lockout portion is configured to inhibit the transducer power circuit from powering the ultrasonic transducer in the locked-out state, and wherein the first and second lockout portion in the predetermined alignment are collectively configured to allow the activation switch to power the ultrasonic transducer in the operational state.

7. The ultrasonic surgical instrument of claim 6, wherein the first lockout portion includes a first electrical shunt, wherein the second lockout portion includes a first pair of electrical contacts, wherein the first pair of electrical contacts define a first electrical gap in the locked-out state to inhibit electrical flow between the first pair of electrical contacts, wherein the first electrical shunt in the predetermined alignment electrically connects the first pair of electrical contacts for the operational state.

8. The ultrasonic surgical instrument of claim 7, wherein the first lockout portion includes a second electrical shunt, wherein the second lockout portion includes a second pair of electrical contacts, wherein the second pair of electrical contacts defines a second electrical gap in the locked-out state to inhibit electrical flow between the second pair of electrical contacts, wherein the second electrical shunt in the predetermined alignment electrically connects the second pair of electrical contacts for the operational state.

9. The surgical instrument of claim 6, wherein the first lockout portion includes a first metallic member, wherein the second lockout portion includes a second metallic member, wherein the first metallic member and the second metallic member in the predetermined alignment collectively define an electrical capacitor, and wherein the electrical capacitor is configured to generate a capacitance in the predetermined alignment for the operational state.

10. The surgical instrument of claim 6 wherein the first lockout portion includes a first metallic member, wherein the second lockout portion includes an electrical coil, wherein the electrical coil receives the metallic member in the predetermined alignment to collectively define an electrical inductor, wherein the electrical inductor is configured to generator an inductance in the predetermined alignment for the operational state.

11. The surgical instrument of claim 6, wherein the first lockout portion includes a reflective surface, wherein the second lockout portion includes an infrared light source and an infrared receiver, wherein the infrared light source is configured to direct infrared light to reflect from the reflective surface and into the infrared receiver in the predetermined alignment for the operational state.

12. The surgical instrument of claim 6, wherein the first lockout portion includes a ramp surface, wherein the second lockout portion includes a movable member connected to a potentiometer, wherein the movable member is configured to be moved by the ramp surface from a disconnected position, through an intermediate position, and to a connected position as the first modular assembly is being mechanically connected to the second modular assembly with the predetermined alignment, wherein the movable member in the disconnected position directs the potentiometer to generate a disconnected voltage for indicating that the first modular assembly is completely disconnected from the second modular assembly and in the locked-out state, wherein the movable member in the intermediate position directs the potentiometer to generate an intermediate voltage for indicating that the first modular assembly is partially connected to the second modular assembly and in the locked-out state, and wherein the movable member in the connected position directs the potentiometer to generate a connected voltage for indicating that the first modular assembly is connected to the second modular assembly with the predetermined alignment in the operational state.

13. The ultrasonic surgical instrument of claim 6, wherein the first lockout portion includes an abutment surface on the first modular assembly, wherein the second lockout portion includes a pair of electrical contacts and a movable member having an electrical shunt positioned thereon configured to move from a first position to a second position, wherein the pair of electrical contacts define an electrical gap in the locked-out state to inhibit electrical flow between the pair of electrical contacts with the movable member in the first position, wherein the abutment surface is configured to urge the movable member from the first position to the second position as the first modular assembly is mechanically connected to the second modular assembly with the predetermined alignment, and wherein the electrical shunt in the second position with the predetermined alignment electrically connects the pair of electrical contacts for the operational state.

14. The ultrasonic surgical instrument of claim 6, wherein the first lockout portion includes a magnet on the first modular assembly, wherein the second lockout portion includes a pair of electrical contacts and a movable member having an electrical shunt positioned thereon configured to move from a first position to a second position, wherein the pair of electrical contacts define an electrical gap in the locked-out state to inhibit electrical flow between the pair of electrical contacts with the movable member in the first position, wherein the magnet is configured to urge the movable member from the first position to the second position as the first modular assembly is mechanically connected to the second modular assembly with the predetermined alignment, and wherein the electrical shunt in the second position with the predetermined alignment electrically connects the pair of electrical contacts for the operational state.

15. An ultrasonic surgical instrument, comprising:
(a) a first modular assembly, including:
(i) a shaft assembly having an acoustic waveguide extending therealong,
(ii) an end effector projecting distally from the shaft assembly, wherein the end effector is further configured to manipulate a tissue, wherein the end effector includes an ultrasonic blade extending from the acoustic waveguide and a clamp arm assembly movably connected relative to the ultrasonic blade and configured to compress the tissue against the ultrasonic blade;

(b) a second modular assembly configured to mechanically couple with the first modular assembly in a predetermined alignment relative to each other, wherein the second modular assembly includes:
   (i) a body assembly configured to support an ultrasonic transducer;
   (ii) a transducer power circuit configured to electrically connect to the ultrasonic transducer and a generator, and
   (iii) an activation switch electrically connected to the transducer power circuit, wherein the activation switch is configured to selectively power the ultrasonic transducer by directing electrical power from the generator to the ultrasonic transducer with the first and second modular assemblies in the predetermined alignment, and (c) an electrical lockout configured to inhibit the activation switch from powering the ultrasonic transducer with the first and second modular assemblies misaligned from the predetermined alignment such that the first and second modular assemblies are in a locked-out state, wherein the electrical lockout is further configured to allow the activation switch to power the ultrasonic transducer with the first and second modular assemblies in the predetermined alignment such that the first and second modular assemblies are in an operational state, wherein the electrical lockout includes:
   (i) a first lockout portion positioned on the first modular assembly, and
   (ii) a second lockout portion electrically connected to the transducer power circuit and positioned on the body,
   wherein the second lockout portion is configured to inhibit the transducer power circuit from powering the ultrasonic transducer in the locked-out state, and wherein the first and second lockout portion in the predetermined alignment are collectively configured to allow the activation switch to power the ultrasonic transducer in the operational state,
   wherein the first lockout portion includes a first electrical shunt, wherein the second lockout portion includes a first pair of electrical contacts, wherein the first pair of electrical contacts define a first electrical gap in the locked-out state to inhibit electrical flow between the first pair of electrical contacts, wherein the first electrical shunt in the predetermined alignment electrically connects the first pair of electrical contacts for the operational state.

16. The ultrasonic surgical instrument of claim 15, wherein the second modular assembly further includes an ultrasonic transducer supported therein.

17. An ultrasonic surgical instrument, comprising:
(a) a first modular assembly, including:
   (i) at least a portion of an end effector configured to manipulate a tissue;

(b) a second modular assembly configured to mechanically couple with the first modular assembly in a predetermined alignment relative to each other, wherein the second modular assembly includes:
   (i) a body assembly configured to support an ultrasonic transducer,
   (ii) a transducer power circuit configured to electrically connect to the ultrasonic transducer and a generator, and
   (iii) an activation switch electrically connected to the transducer power circuit, wherein the activation switch is configured to selectively power the ultrasonic transducer by directing electrical power from the generator to the ultrasonic transducer with the first and second modular assemblies in the predetermined alignment; and (c) an electrical lockout electrically connected to the transducer power circuit, wherein the electrical lockout includes:
   wherein the electrical lockout is configured to inhibit the activation switch from powering the ultrasonic transducer with the first and second modular assemblies misaligned from the predetermined alignment such that the first and second modular assemblies are in a locked-out state,
   wherein the electrical lockout is further configured to allow the activation switch to power the ultrasonic transducer with the first and second modular assemblies in the predetermined alignment such that the first and second modular assemblies are in an operational state, and
   wherein the electrical lockout further includes:
      (i) a first lockout portion positioned on the first modular assembly, and
      (ii) a second lockout portion positioned on the second modular assembly,
      wherein the first lockout portion includes one of an electrical shunt or a pair of electrical contacts, and wherein the second lockout includes the other of the electrical shunt or the pair of electrical contacts.

18. The ultrasonic surgical instrument of claim 17, wherein the pair of electrical contacts define an electrical gap in the locked-out state to inhibit electrical flow between the pair of electrical contacts, wherein the first electrical shunt in the predetermined alignment electrically connects the pair of electrical contacts for the operational state.

19. The ultrasonic surgical instrument of claim 18, wherein the first lockout portion includes the electrical shunt, and wherein the second lockout portion includes the pair of electrical contacts.

20. The ultrasonic surgical instrument of claim 19, wherein the second lockout portion is electrically connected to the transducer power circuit and positioned on the body, wherein the second lockout portion is configured to inhibit the transducer power circuit from powering the ultrasonic transducer in the locked-out state, and wherein the first and second lockout portion in the predetermined alignment are collectively configured to allow the activation switch to power the ultrasonic transducer in the operational state.

* * * * *